US012617791B2

(12) United States Patent
Liu et al.

(10) Patent No.: US 12,617,791 B2
(45) Date of Patent: May 5, 2026

(54) TRIHETEROCYCLIC DERIVATIVE, AND PHARMACEUTICAL COMPOSITION AND APPLICATION THEREOF

(71) Applicant: SHANGHAI DE NOVO PHARMATECH CO., LTD., Shanghai (CN)

(72) Inventors: Xiaohui Liu, Shanghai (CN); Fengtao Liu, Shanghai (CN); Daxin Gao, Shanghai (CN)

(73) Assignee: SHANGHAI DE NOVO PHARMATECH CO., LTD., Shanghai (CN)

( * ) Notice: Subject to any disclaimer, the term of this patent is extended or adjusted under 35 U.S.C. 154(b) by 371 days.

(21) Appl. No.: 18/247,742

(22) PCT Filed: Oct. 15, 2021

(86) PCT No.: PCT/CN2021/123992
§ 371 (c)(1),
(2) Date: Apr. 3, 2023

(87) PCT Pub. No.: WO2022/078480
PCT Pub. Date: Apr. 21, 2022

(65) Prior Publication Data

US 2024/0025899 A1 Jan. 25, 2024

(30) Foreign Application Priority Data

Oct. 16, 2020 (CN) ......................... 202011107416.5
Jan. 25, 2021 (CN) ......................... 202110097827.9
Aug. 13, 2021 (CN) ......................... 202110929213.2

(51) Int. Cl.
*C07D 471/14* (2006.01)
*A61P 35/00* (2006.01)

(52) U.S. Cl.
CPC ............ *C07D 471/14* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 6,518,265 B1 | 2/2003 | Kato et al. | |
| 6,951,865 B2 * | 10/2005 | Hibi | A61P 25/06 544/251 |
| 7,329,668 B2 | 2/2008 | Qiu et al. | |
| 2010/0048923 A1 | 2/2010 | Nishida | |
| 2012/0208792 A1 | 8/2012 | Chua et al. | |
| 2013/0065881 A1 | 3/2013 | Pastor Fernandez et al. | |
| 2017/0216304 A1 | 8/2017 | Wortmann et al. | |
| 2019/0300547 A1 | 10/2019 | Burgdorf et al. | |

FOREIGN PATENT DOCUMENTS

| | | | |
|---|---|---|---|
| CN | 102036561 | A | 4/2011 |
| CN | 102791715 | A | 11/2012 |
| CN | 109071565 | A | 12/2018 |
| CN | 111205310 | A | 5/2020 |
| WO | 9313103 | A1 | 7/1993 |
| WO | 2007015632 | A1 | 2/2007 |
| WO | 2007046426 | A1 | 4/2007 |
| WO | 2010037765 | A2 | 4/2010 |
| WO | 2012027240 | A1 | 3/2012 |
| WO | 2014140644 | A1 | 9/2014 |
| WO | 2015084384 | A1 | 6/2015 |
| WO | 2016061097 | A1 | 4/2016 |
| WO | 2017123588 | A1 | 7/2017 |
| WO | 2017180723 | A1 | 10/2017 |
| WO | 2019036641 | A1 | 2/2019 |
| WO | 2020049017 | A1 | 3/2020 |

OTHER PUBLICATIONS

Golub et al., Science, vol. 286, Oct. 15, 1999, pp. 531-537 (Year: 1999).*
Jul. 1, 30, 2024 extended European Search Report issued in European Patent Application No. 21879521.9.
Jan. 14, 2022 International Search Report issued in International Patent Application No. PCT/CN2021/123992.
Jan. 14, 2022 Written Opinion of the International Searching Authority issued in International Patent Application No. PCT/CN2021/123992.

(Continued)

*Primary Examiner* — Sarah Pihonak
*Assistant Examiner* — Donna M Nestor
(74) *Attorney, Agent, or Firm* — Houston Beshining Law Office PLLC; Liangang Ye

(57) ABSTRACT

A triheterocyclic derivative, and a pharmaceutical composition and an application thereof. The triheterocyclic derivative (I), and a stereoisomer or a pharmacologically acceptable salt thereof have the following structure. The triheterocyclic derivative has good effects of inhibiting ATR levels in vivo and in vitro, and furthermore, the triheterocyclic derivative can also effectively treat diseases caused by abnormal ATR levels, such as cancers.

(I)

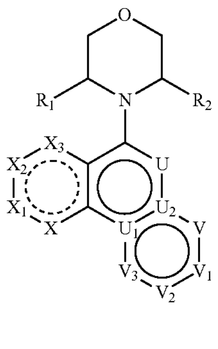

20 Claims, 1 Drawing Sheet

(56) References Cited

OTHER PUBLICATIONS

Foote Kevin M. et.al Discovery and Characterization of AZD6738, a Potent Inhibitor of Ataxia Telangiectasia Mutated and Rad3 Related (ATR) Kinase with Application as an Anticancer Agent; Journal of Medicinal Chemistry vol. 61, Oct. 22, 2018 (Oct. 22, 2018), pp. 9889-9907.

Stephen P. Jackson & Jiri Bartek, The DNA-damage response in human biology and disease Nature, Oct. 22, 2009, vol. 461(7267), 1071-1078.

Cimprich K.A., ATR: an essential regulator of genome integrity Nature Rev. Mol. Cell Biol., 2008, 9:616-627.

Reaper, p. M., Selective killing of ATM—or p53-deficient cancer cells through inhibition of ATR Nat. Chem. Biol., 2011, 7, 428-430.

Sultana R, Ataxia Telangiectasia Mutated and Rad3 Related (ATR) Protein Kinase Inhibition Is Synthetically Lethal in XRCC1 Deficient Ovarian Cancer Cells PLoS One, 2013, 8(2): e57098.

Lecona E, Replication stress and cancer:Itt akes two to tango Exp Cell Res, 2014, 329(1): 26-34.

Berge et al., "Pharmaceutically acceptable salts" J. Pharm. Sci., 66, 1-19(1977).

RN: 2130473-15-1, Registry(STN), STN on the WEB, Sep. 25, 2017.

Jul. 8, 2025, First Examination Report issued for a corresponding Japanese Patent Application No. JP2023-523141.

Sep. 12, 2025, First Examination Report issued for a corresponding Chinese Patent Application No. CN2021112012103.

Mar. 3, 2026 First Office Action issued in Korean Patent Application No. 10-2023-7012298.

* cited by examiner

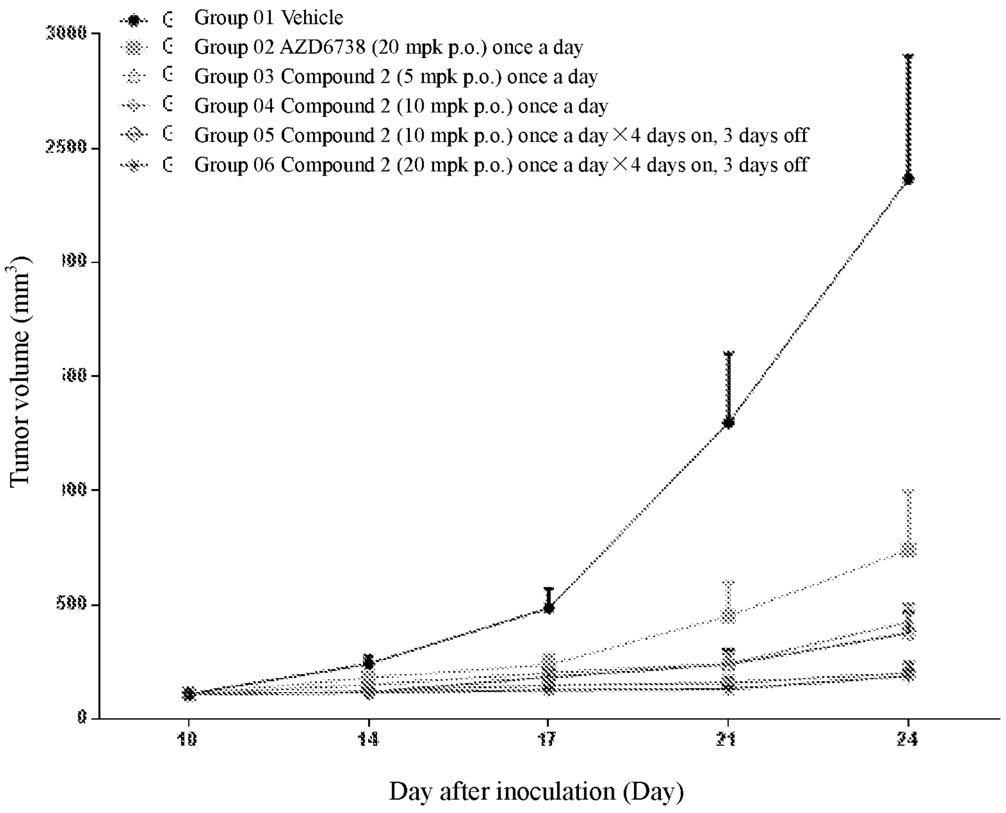
Group 01 Vehicle
Group 02 AZD6738 (20 mpk p.o.) once a day
Group 03 Compound 2 (5 mpk p.o.) once a day
Group 04 Compound 2 (10 mpk p.o.) once a day
Group 05 Compound 2 (10 mpk p.o.) once a day ×4 days on, 3 days off
Group 06 Compound 2 (20 mpk p.o.) once a day ×4 days on, 3 days off
Tumor volume (mm3)
3000
2500
500
0
10
14
17
21
24
Day after inoculation (Day)

TRIHETEROCYCLIC DERIVATIVE, AND PHARMACEUTICAL COMPOSITION AND APPLICATION THEREOF

The present application is a National Stage of International Application No. PCT/CN2021/123992, filed on Oct. 15, 2021, which claims the priorities of the Chinese Patent Application NO. CN202011107416.5 filed on Oct. 16, 2020, the Chinese Patent Application NO. CN202110097827.9 filed on Jan. 25, 2021, and the Chinese Patent Application NO. CN202110929213.2 filed on Aug. 13, 2021. The contents of the above Chinese patent applications are incorporated herein by reference in their entireties.

TECHNICAL FIELD

The present disclosure relates to a triheterocyclic derivative, a pharmaceutical composition thereof and a use thereof as a therapeutic agent, especially as a cancer therapeutic agent.

BACKGROUND

Human cells suffer from hundreds of DNA damages every day. The causes of DNA damage include normal cell functions (such as oxidative metabolites), DNA metabolites (such as spontaneous errors during DNA transcription and replication), and environmental factors (such as ultraviolet light, ionizing radiation, genotoxins), etc. If the above-mentioned damages can not be repaired correctly, it will lead the loss of the activity of cells or organisms. The accumulation of DNA damages can also affect the stability and integrity of the genome and promote the formation of cancer. DNA damages may occur through oxidation or alkylation of DNA bases, DNA base mismatches and dimerization, breaks and discontinuities in the DNA backbone, intra-strand/inter-strand DNA cross-links, and general changes in DNA structure. To ensure the stability and integrity of the cellular genome, cells have a complex set of DNA damage response (DDR) mechanisms that can recognize and deal with these specific types of DNA damage in specific parts of the cell cycle to maintain genomic integrity and cell viability. It was found that multiple DDR mechanisms exist in healthy cells and these repair mechanisms can compensate each other during DNA repair. (Jackson S P, Nature, 2009, 461(7267), 1071-1078). However, many cancer cells have defects in multiple DNA repair pathways and therefore exhibit a greater dependence on undamaged DNA repair pathways.

Ataxia telangiectasia mutated and $Rad_3$-related kinase (ATR, also known as FRAP-Related Protein 1; FRP1; MEC1; SCK1; SECKL1) is a member of the phosphatidylinositol-3 kinase (PIKK) protein family, it is an important kinase that can activate cell responses after DNA damage, thereby arresting cell cycle progression, stabilizing replication forks and repairing DNA, thereby avoiding apoptosis (Cimprich K. A., Nature Rev. Mol. Cell Biol., 2008, 9:616-627). ATR acts by stabilizing stalled replication forks, regulating activation of cell cycle checkpoints and DNA damage repair. After ATR is activated, it will activate three signal transduction pathways to block cell cycle progression, promote DNA repair, and stabilize replication forks by regulating its downstream regulatory factors (mainly including Chk1, WRN, and FANCI). Although the presence of RPA-coated single-stranded DNA is a common feature of ATR activation, in some cases ATR can also be activated without uncoupling of DNA helicase and DNA polymerase, e.g., by UV radiation, platinum chemotherapy or alkylating agent, etc.

Since DNA repair in tumor cells may be defective due to the presence of multiple mutations, resulting in a greater dependence on undamaged DNA repair pathways. Therefore, the theory of synthetic lethality can be used to kill specific tumor cells while preserving healthy cells. Current cancer treatments, including chemotherapy and ionizing radiation, can induce DNA damage and replication fork arrest, thereby activating cell cycle checkpoints and leading to cell cycle arrest. This response mechanism is an important mechanism that helps cancer cells survive during treatment. Broken double-strand DNA or replication stress can rapidly activate ATR, and the corresponding ATR can initiate a series of downstream targets such as Chk1 (ATR substrate), p53, DNA topoisomerase 2 binding protein (TopBP1), thereby leading to DNA repair and cell cycle arrest. Because the ATR gene rarely mutates, it is easily activated during cancer chemotherapy. In addition, several synthetic lethal interactions can be produced by inhibiting ATR, especially interactions with the ATM/p53 pathway. p53 is the most common tumor suppressor gene mutation, DNA repair of cells with ATM/p53 gene deficiency or mutation are more dependent on the activation of ATR (Reaper, P. M., Nat. Chem. Biol., 2011, 7, 428-430).

Studies have shown that the loss of specific DNA repair proteins, such as X-ray cross-complementary repair gene 1, mismatch excision cross-complementary repair gene 1, can also lead to tumor cells being more sensitive to ATR inhibition (Sultana R, PLoS One, 2013, 8(2): e57098). In addition, hypoxic tumor cells may cause replication stress, making them more sensitive to ATR inhibition, and by inhibiting ATR, the sensitivity of tumor cells to ionizing radiation and chemotherapy can be selectively increased, and the sensitivity of tumor cells to replication stress can be increased, and the increased level is many times higher than that of normal cells (Lecona E, Exp Cell Res, 2014, 329(1): 26-34). Moreover, since ATR is essential for maintaining telomere homologous recombination, tumor cells that rely on the alternative elongation pathway of telomere for DNA damage repair are also more sensitive to ATR inhibition.

As a DNA damage response mechanism, the ATR pathway plays an important role in the survival of tumor cells. Inhibition of key factor ATR can induce the death of ATR pathway-dependent malignant tumor cells and has little effect on normal cells, which is an ideal target for the development of low-toxicity and high-efficiency targeted drugs. Currently, there are two small molecular entities, VX970 and AZD6738 have entered clinical phase II trials, and there are also many patent publications on the ATR pathway: WO2015/084384, WO2017/180723, WO2016/061097, WO2014/140644, WO2007/015632, WO2017/123588, WO2007/046426, but there is no corresponding drug on the market, and the triheterocyclic derivative of the present disclosure provides a new idea for the development of ATR inhibitors.

CONTENT OF THE PRESENT INVENTION

The technical problem to be solved by the present disclosure is to provide a novel triheterocyclic derivative, a pharmaceutical composition thereof and a use thereof. The triheterocyclic derivative of the present disclosure has good ATR inhibitory effect, and can effectively treat and/or alleviate ATR-mediated diseases, such as malignant tumors.

The present disclosure provides a compound of formula (I), a stereoisomer or a pharmaceutically acceptable salt thereof, (I)

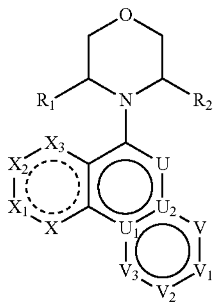

wherein,

X is $CR_3$ or $NR_5$; $X_1$ is $CR_{3a}$, $CR_{3a}R_{4a}$ or $NR_{5a}$; $X_2$ is $CR_{3b}$, $CR_{3b}R_{4b}$ or $NR_{5b}$; $X_3$ is a bond, $CR_{3c}$, $CR_{3c}R_{4c}$ or $NR_{5c}$;

U is N or CH;

$U_1$ and $U_2$ are each independently N or C; and $U_1$ and $U_2$ are not N at the same time;

V is $NR_6$ or $CR_7$; $V_1$ is N, $NR_6$a or $CR_7$a; $V_2$ is N, $NR_{6b}$ or $CR_{7b}$; $V_3$ is a bond, N, $NR_{6c}$ or $CR_{7c}$;

$R_1$ is hydrogen or $C_{1-6}$ alkyl;

$R_2$ is methyl;

$R_3$, $R_{3a}$, $R_{3b}$ and $R_{3c}$ are each independently hydrogen, halogen, cyano, nitro, $C_{1-6}$ alkyl, $C_{2-6}$ alkynyl, $C_{2-6}$ alkenyl, $C_{6-10}$ aryl, $C_{3-8}$ cycloalkyl, 3- to 8-membered heterocycloalkyl, 5- to 6-membered heteroaryl, $C_{6-10}$ aryl-$C_{1-6}$ alkyl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, —$SR_a$, —$OR_a$, —$OC(O)R_a$, —$OC(O)OR_a$, —$OC(O)NR_aR_b$, —$C(O)OR_a$, —$C(O)R_a$, —$C(O)NR_aR_b$, —$C(O)N(R_b)OR_a$, —$C(O)NR_bS(O)_2R_a$, —$C(=NH)R_a$, —$NR_aR_b$, —$NR_bC(O)R_a$, —$N(R_b)C(O)OR_a$, —$N(R_b)C(O)NR_aR_b$, —$NR_bS(O)_2R_a$, —$NR_bC(=NH)R_a$, —$NR_bC(=NH)NR_bR_a$, —$S(O)_{1-2}R_a$, —$S(O)_2NR_aR_b$, —$S(O)(=NCN)R_a$, —$S(O)(=NR_b)R_a$ or —$NR_bS(O)_2NR_aR_b$; wherein, the $C_{1-6}$ alkyl, $C_{2-6}$ alkynyl, $C_{2-6}$ alkenyl, $C_{6-10}$ aryl, $C_{3-8}$ cycloalkyl, 3- to 8-membered heterocycloalkyl, 5- to 6-membered heteroaryl, $C_{6-10}$ aryl-$C_{1-6}$ alkyl, $C_{3-8}$ cycloalkyl-$C_{1-6}$ alkyl, 3- to 8-membered heterocycloalkyl-$C_{1-6}$ alkyl, or 5- to 6-membered heteroaryl-$C_{1-6}$ alkyl is unsubstituted or optionally substituted at any position by 1 to 3 of the following substituents selected from halogen, cyano, nitro, —$SR_a$, —$OR_a$, —$OC(O)R_a$, —$OC(O)OR_a$, —$OC(O)NR_aR_b$, —$C(O)OR_a$, —$C(O)R_a$, —$C(O)NR_aR_b$, —$C(O)NR_bS(O)_2R_a$, —$NR_aR_b$, —$NR_bC(O)R_a$, —$N(R_b)C(O)OR_a$, —$N(R_b)C(O)NR_aR_b$, —$NR_bC(=NH)R_a$, —$NR_bC(=NH)NR_aR_b$, —$NR_bS(O)_2R_a$, —$NR_bS(O)_2NR_aR_b$, —$S(O)_{1-2}R_a$, —$S(O)_2NR_aR_b$, —$S(O)(=NCN)R_a$ and —$S(O)(=NR_b)R_a$;

$R_{4a}$, $R_{4b}$ and $R_{4c}$ are each independently hydrogen, halogen, $C_{1-6}$ alkyl, $C_{1-6}$ alkoxy, halo $C_{1-6}$ alkyl or halo $C_{1-6}$ alkoxy;

$R_5$, $R_{5a}$, $R_{5b}$ and $R_{5c}$ are each independently hydrogen, $C_{1-6}$ alkyl, $C_{2-6}$ alkynyl, $C_{2-6}$ alkenyl, $C_{6-10}$ aryl, $C_{3-8}$ cycloalkyl, 3- to 8-membered heterocycloalkyl, 5- to 6-membered heteroaryl, $C_{6-10}$ aryl-$C_{1-6}$ alkyl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, —$SR_a$, —$OR_a$, —$C(O)OR_a$, —$C(O)R_a$, —$C(O)NR_aR_b$, —$C(O)N(R_b)OR_a$, —$C(O)NR_bS(O)_2R_a$, —$C(=NH)R_a$, —$S(O)_{1-2}R_a$, —$S(O)_2NR_aR_b$, —$S(O)(=NCN)R_a$ or —$S(O)(=NR_b)R_a$; wherein, the $C_{1-6}$ alkyl, $C_{2-6}$ alkynyl, $C_{2-6}$ alkenyl, $C_{6-10}$ aryl, $C_{3-8}$ cycloalkyl, 3- to 8-membered heterocycloalkyl, 5- to 6-membered heteroaryl, $C_{6-10}$ aryl-$C_{1-6}$ alkyl, $C_{3-8}$ cycloalkyl-$C_{1-6}$ alkyl, 3- to 8-membered heterocycloalkyl-$C_{1-6}$ alkyl, or 5- to 6-membered heteroaryl-$C_{1-6}$ alkyl is unsubstituted or optionally substituted at any position by 1 to 3 of the following substituents selected from halogen, cyano, nitro, —$SR_a$, —$OR_a$, —$OC(O)R_a$, —$OC(O)OR_a$, —$OC(O)NR_aR_b$, —$C(O)OR_a$, —$C(O)R_a$, —$C(O)NR_aR_b$, —$C(O)NR_bS(O)_2R_a$, —$NR_aR_b$, —$NR_bC(O)R_a$, —$N(R_b)C(O)OR_a$, —$N(R_b)C(O)NR_aR_b$, —$NR_bC(=NH)R_a$, —$NR_bC(=NH)NR_aR_b$, —$NR_bS(O)_2R_a$, —$NR_bS(O)_2NR_aR_b$, —$S(O)_{1-2}R_a$, —$S(O)_2NR_aR_b$, —$S(O)(=NCN)R_a$ and —$S(O)(=NR_b)R_a$;

$R_6$, $R_{6a}$, $R_{6b}$ and $R_{6c}$ are each independently hydrogen, $C_{1-6}$ alkyl, $C_{1-6}$ alkoxy, halo $C_{1-6}$ alkyl, halo $C_{1-6}$ alkoxy, $C_{3-8}$ cycloalkyl, 3- to 8-membered heterocycloalkyl, $C_{6-10}$ aryl, 5- to 10-membered heteroaryl, $C_{3-8}$ cycloalkyl-$C_{1-6}$ alkyl, or 3- to 8-membered heterocycloalkyl-$C_{1-6}$ alkyl, wherein, the $C_{6-10}$ aryl or 5- to 10-membered heteroaryl is unsubstituted or optionally substituted at any position by 1 to 3 of the following substituents selected from halogen, cyano, —$R_c$, —$OR_c$, —$NR_cR_d$, —$N(CN)R_c$, —$N(OR_d)R_c$, —$S(O)_{0-2}R_c$, —$C(O)R_c$, —$C(O)OR_c$, —$C(O)NR_cR_d$, —$C(NH)NR_cR_d$, —$NR_dC(O)R_c$, —$NR_dC(O)NR_cR_d$, —$NR_dS(O)_2R_c$ and —$OC(O)R_c$;

$R_7$, $R_{7a}$, $R_{7b}$ and $R_{7c}$ are each independently hydrogen, halogen, cyano, $C_{1-6}$ alkyl, $C_{1-6}$ alkoxy, halo $C_{1-6}$ alkyl, halo $C_{1-6}$ alkoxy, $C_{3-8}$ cycloalkyl, 3- to 8-membered heterocycloalkyl, $C_{6-10}$ aryl, 5- to 10-membered heteroaryl, $C_{3-8}$ cycloalkyl-$C_{1-6}$ alkyl or 3- to 8-membered heterocycloalkyl-$C_{1-6}$ alkyl, wherein, the $C_{6-10}$ aryl or 5- to 10-membered heteroaryl is unsubstituted or optionally substituted at any position by 1 to 3 of the following substituents selected from halogen, cyano, —$R_c$, —$OR_c$, —$NR_cR_d$, —$N(CN)R_c$, —$N(OR_d)R_c$, —$S(O)_{0-2}R_c$, —$C(O)R_c$, —$C(O)OR_c$, —$C(O)NR_cR_d$, —$C(NH)NR_cR_d$, —$NR_dC(O)R_c$, —$NR_dC(O)NR_cR_d$, —$NR_dS(O)_2R_c$ and —$OC(O)R_c$;

each of $R_a$, $R_b$, $R_c$ and $R_d$ is independently hydrogen, $C_{1-6}$ alkyl, $C_{2-6}$ alkenyl, $C_{2-6}$ alkynyl, $C_{3-8}$ cycloalkyl, 3- to 8-membered heterocycloalkyl, $C_{6-10}$ aryl, 5- to 6-membered heteroaryl, $C_{3-8}$ cycloalkyl-$C_{1-6}$ alkyl, 3- to 8-membered heterocycloalkyl-$C_{1-6}$ alkyl, phenyl-$C_{1-6}$ alkyl, or 5- to 6-membered heteroaryl-$C_{1-6}$ alkyl; the $R_a$, $R_b$, $R_c$ and $R_d$ are unsubstituted or optionally substituted at any position by 1 to 3 of the following substituents selected from halogen, hydroxyl, amino, carboxyl, $C_{1-6}$ alkyl, $C_{1-6}$ alkoxy, $C_{1-6}$ alkylamino, halo $C_{1-6}$ alkyl, halo $C_{1-6}$ alkoxy, $C_{2-6}$ alkenyl and $C_{2-6}$ alkynyl.

All the embodiments described below as described for formula (I), and combinations of any embodiments as described for formula (I) are within the scope of formula (I) in the present disclosure.

In some embodiments, $R_1$ is hydrogen or methyl.

In some embodiments, $R_2$ is hydrogen or methyl.

In some embodiments, $R_1$ is hydrogen, $R_2$ is methyl.

In some embodiments, each of $R_a$, $R_b$, $R_c$ and $R_d$ is independently hydrogen, $C_{1-6}$ alkyl, $C_{2-6}$ alkenyl, $C_{2-6}$ alkynyl, $C_{3-8}$ cycloalkyl, 3- to 8-membered heterocycloalkyl, $C_{6-10}$ aryl, 5- to 6-membered heteroaryl, $C_{3-8}$ cycloalkyl-$C_{1-6}$ alkyl, 3- to 8-membered heterocycloalkyl-$C_{1-6}$ alkyl, phenyl-$C_{1-6}$ alkyl, or 5- to 6-membered heteroaryl-$C_{1-6}$ alkyl; the $R_a$, $R_b$, $R_c$ and $R_d$ are unsubstituted or optionally substituted at any position by one or more of the following substituent(s) selected from halogen, hydroxyl, amino, carboxyl, $C_{1-6}$ alkyl, $C_{1-6}$ alkoxy, $C_{1-6}$ alkylamino, halo $C_{1-6}$ alkyl, halo $C_{1-6}$ alkoxy, $C_{2-6}$ alkenyl and $C_{2-6}$ alkynyl.

In some embodiments, $R_a$ and $R_b$ together with the N atom to which they are attached form 3- to 8-membered heterocycloalkyl.

In some embodiments, $R_c$ and $R_d$ together with the N atom to which they are attached form 3- to 8-membered heterocycloalkyl.

In some embodiments, each $R_a$ is independently hydrogen, $C_{1-6}$ alkyl, $C_{3-8}$ cycloalkyl or 3- to 8-membered heterocycloalkyl; the $R_a$ is unsubstituted or optionally substituted at any position by 1 to 3 of the following substituents selected from halogen, hydroxyl, amino, $C_{1-6}$ alkoxy, $C_{1-6}$ alkylamino, halo $C_{1-6}$ alkyl and halo $C_{1-6}$ alkoxy.

In some embodiments, each $R_a$ is independently hydrogen or $C_{1-6}$ alkyl; the $C_{1-6}$ alkyl is unsubstituted or optionally substituted at any position by 1 to 3 of the following substituents selected from halogen, hydroxyl, amino, $C_{1-6}$ alkoxy, $C_{1-6}$ alkylamino, halo $C_{1-6}$ alkyl and halo $C_{1-6}$ alkoxy.

In some embodiments, each $R_b$ is independently hydrogen or $C_{1-6}$ alkyl.

In some embodiments, each $R_c$ is independently hydrogen or $C_{1-6}$ alkyl; the $C_{1-6}$ alkyl is unsubstituted or optionally substituted at any position by 1 to 3 of the following substituents selected from halogen, hydroxyl, amino, $C_{1-6}$ alkoxy, $C_{1-6}$ alkylamino, halo $C_{1-6}$ alkyl and halo $C_{1-6}$ alkoxy.

In some embodiments, each $R_d$ is independently hydrogen or $C_{1-6}$ alkyl.

In some embodiments, $R_3$ is $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, $-NR_bS(O)_2R_a$, $-S(O)_{1-2}R_a$, $-S(O)_2NR_aR_b$, $-S(O)(=NCN)R_a$ or $-S(O)(=NR_b)R_a$; wherein, the $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, or 3- to 8-membered heterocycloalkyl-$C_{1-6}$ alkyl is unsubstituted or optionally substituted at any position by 1 to 3 of the following substituents selected from halogen, $-CN$, $-SR_a$, $-OR_a$, $-C(O)OR_a$, $-C(O)R_a$, $-C(O)NR_aR_b$, $-NR_aR_b$, $-NR_bC(O)R_a$, $-NR_bS(O)_2R_a$, $-S(O)_{1-2}R_a$, $-S(O)_2NR_aR_b$, $-S(O)(=NCN)R_a$ and $-S(O)(=NR_b)R_a$.

In some embodiments, $R_{3a}$, $R_{3b}$ and $R_{3c}$ are each independently hydrogen, halogen, cyano, $C_{1-6}$ alkyl, halo $C_{1-6}$ alkyl or halo $C_{1-6}$ alkoxy.

In some embodiments, $R_{3a}$, $R_{3b}$ and $R_{3c}$ are each independently hydrogen.

In some embodiments, $R_{4a}$, $R_{4b}$ and $R_{4c}$ are each independently hydrogen or $C_{1-6}$ alkyl.

In some embodiments, $R_{4a}$, $R_{4b}$ and $R_{4c}$ are each independently hydrogen.

In some embodiments, $R_5$ is $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, $-S(O)_{1-2}R_a$, $-S(O)_2NR_aR_b$, $-S(O)(=NCN)R_a$ or $-S(O)(=NR_b)R_a$; wherein, the $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, or 3- to 8-membered heterocycloalkyl-$C_{1-6}$ alkyl is unsubstituted or optionally substituted at any position by 1 to 3 of the following substituents selected from halogen, $-CN$, $-SR_a$, $-OR_a$, $-C(O)OR_a$, $-C(O)R_a$, $-C(O)NR_aR_b$, $-NR_aR_b$, $-NR_bC(O)R_a$, $-NR_bS(O)_2R_a$, $-S(O)_{1-2}R_a$, $-S(O)_2NR_aR_b$, $-S(O)(=NCN)R_a$ and $-S(O)(=NR_b)R_a$.

In some embodiments, $R_{5a}$, $R_{5b}$ and $R_{5c}$ are each independently hydrogen, $C_{1-6}$ alkyl, halo $C_{1-6}$ alkyl or $C_{3-8}$ cycloalkyl.

In some embodiments, $R_{5a}$, $R_{5b}$ and $R_{5c}$ are each independently hydrogen.

In some embodiments, the $R_6$ and $R_7$ are each independently 5- to 6-membered heteroaryl; the 5- to 6-membered heteroaryl is unsubstituted or optionally substituted at any position by 1 to 3 of the following substituents selected from halogen, cyano, $-R_c$, $-OR_c$, $-NR_cR_d$, $-N(CN)R_c$, $-N(OR_d)R_c$, $-S(O)_{0-2}R_c$, $-C(O)R_c$, $-C(O)OR_c$, $-C(O)NR_cR_d$, $-C(NH)NR_cR_d$, $-NR_dC(O)R_c$, $-NR_dC(O)NR_cR_d$, $-NR_dS(O)_2R_c$ and $-OC(O)R_c$.

In some embodiments, the $R_6$ and $R_7$ are each independently pyrrolyl, pyrazolyl or isoxazolyl; the pyrrolyl, pyrazolyl or isoxazolyl is unsubstituted or optionally substituted at any position by 1 to 3 of the following substituents selected from halogen, cyano, $-R_c$, $-OR_c$, $-NR_cR_d$, $-N(CN)R_c$, $-N(OR_d)R_c$, $-S(O)_{0-2}R_c$, $-C(O)R_c$, $-C(O)OR_c$, $-C(O)NR_cR_d$, $-C(NH)NR_cR_d$, $-NR_dC(O)R_c$, $-NR_dC(O)NR_cR_d$, $-NR_dS(O)_2R_c$ and $-OC(O)R_c$.

In some embodiments, the $R_6$ and $R_7$ are each independently pyrrolyl, pyrazolyl or isoxazolyl.

In some embodiments, the $R_6$ and $R_7$ are each independently pyrazolyl.

In some embodiments, the $R_{6a}$, $R_{6b}$ and $R_{6c}$ are each independently hydrogen, $C_{1-6}$ alkyl or halo $C_{1-6}$ alkyl.

In some embodiments, the $R_{6a}$, $R_{6b}$ and $R_{6c}$ are each independently hydrogen.

In some embodiments, the $R_{7a}$, $R_{7b}$ and $R_{7c}$ are each independently hydrogen, halogen, cyano, $C_{1-6}$ alkyl, $C_{1-6}$ alkoxy, halo $C_{1-6}$ alkyl or halo $C_{1-6}$ alkoxy.

In some embodiments, the $R_{7a}$, $R_{7b}$ and $R_{7c}$ are each independently hydrogen.

In some embodiments, X is $CR_3$, N, O, S, $SO_2$, S(O)(NH), $CR_3R_4$ or $NR_5$; $X_1$ is $CR_{3a}$, N, O, S, $SO_2$, S(O)(NH), $CR_{3a}R_{4a}$ or $NR_{5a}$; $X_2$ is $CR_{3b}$, N, O, S, $SO_2$, S(O)(NH), $CR_{3b}R_{4b}$ or $NR_{5b}$; $X_3$ is a bond, $CR_{3c}$, N, O, S, $SO_2$, S(O)(NH), $CR_3$, $R_4$, or $NR_{5c}$; $R_4$ is hydrogen, halogen, $C_{1-6}$ alkyl, $C_{1-6}$ alkoxy, halo $C_{1-6}$ alkyl or halo $C_{1-6}$ alkoxy.

In some embodiments, X is $CR_3$, N, O, S, $CR_3R_4$ or $NR_5$; $X_1$ is $CR_3$a, N, O, S, $CR_{3a}R_{4a}$ or $NR_{5a}$; $X_2$ is $CR_{3b}$, N, O, S, $CR_{3b}R_{4b}$ or $NR_{5b}$; $X_3$ is a bond, $CR_{3c}$, N, O, S, $CR_{3c}R_{4c}$ or $NR_{5c}$; $R_4$ is hydrogen, halogen, $C_{1-6}$ alkyl, $C_{1-6}$ alkoxy, halo $C_{1-6}$ alkyl or halo $C_{1-6}$ alkoxy.

In some embodiments, X is $NR_5$; $X_1$ is $CR_{3a}$, $CR_{3a}R_{4a}$ or $NR_5$a; $X_2$ is $CR_{3b}$, $CR_{3b}R_{4b}$ or $NR_{5b}$; $X_3$ is a bond.

In some embodiments, V is N, $NR_6$ or $CR_7$; $V_1$ is N, $NR_{6a}$ or $CR_{7a}$; $V_2$ is N, $NR_{6b}$ or $CR_{7b}$; $V_3$ is a bond, N, $NR_{6c}$ or $CR_{7c}$.

In some embodiments, V is NRS or $CR_7$; $V_1$ is N or $CR_{7a}$; $V_2$ is N or $CR_{7b}$; $V_3$ is a bond, N or $CR_{7c}$.

In some embodiments, U is N.

In some embodiments, $U_1$ and $U_2$ are C.

In some embodiments, the definitions of some groups in the compound of formula (I), the stereoisomer or the pharmaceutically acceptable salt thereof can be described as follows, and the undescribed groups can be described as any one of the above embodiments:

wherein, the group
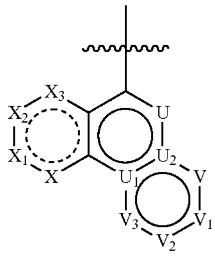
is any one of the following structures:
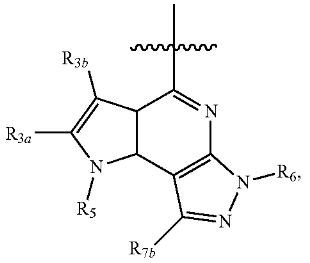
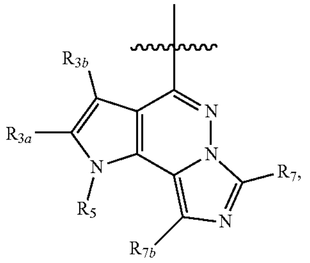
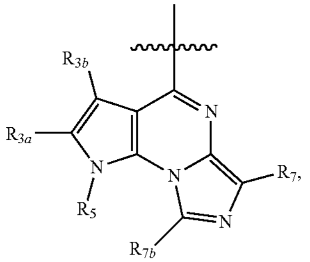
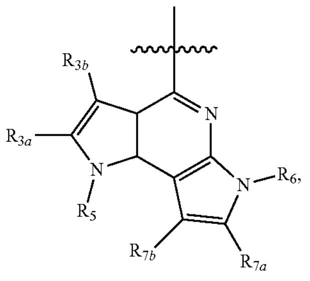
-continued
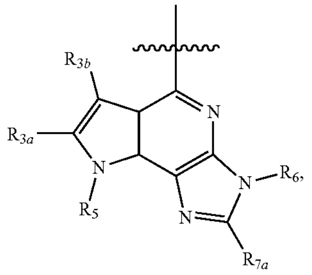
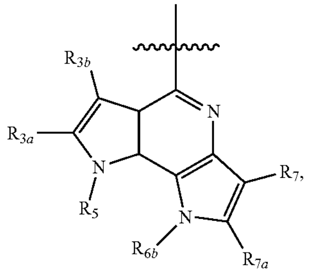
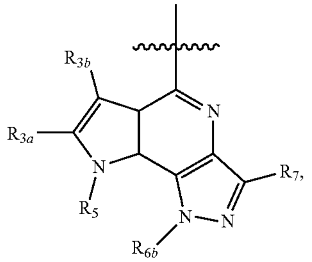
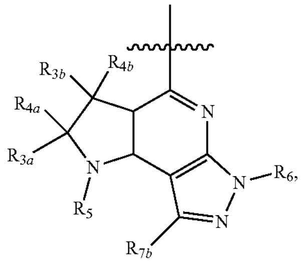
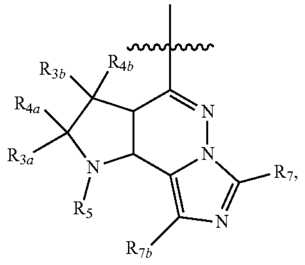
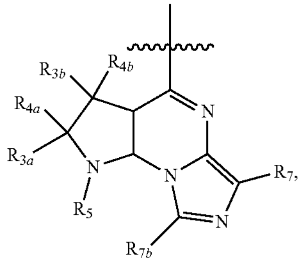

-continued

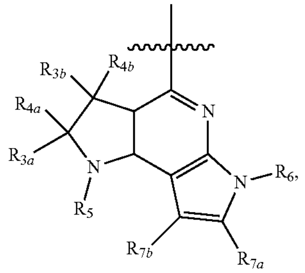

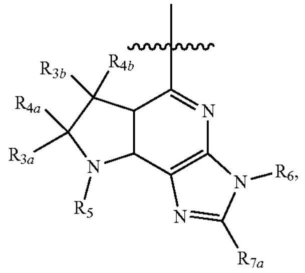

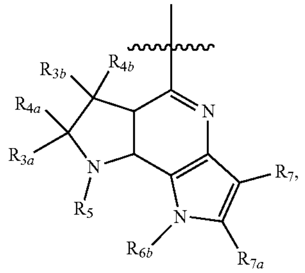

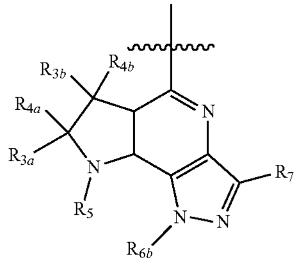

or

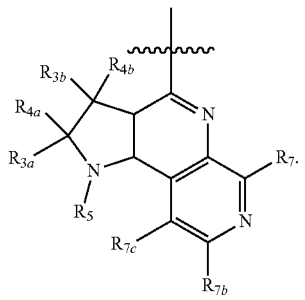

In some embodiments, the compound of formula (I), the stereoisomer or the pharmaceutically acceptable salt thereof is a compound of formula (II), a stereoisomer or a pharmaceutically acceptable salt thereof:

(II)

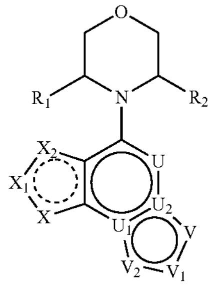

wherein, $U_1$ and $U_2$ are C respectively; V is $NR_6$; $V_1$ is N or $CR_{7a}$; $V_2$ is N or $CR_{7b}$;

or, $U_1$ is C; $U_2$ is N; V is $CR_7$; $V_1$ is N or $CR_{7a}$; $V_2$ is N or $CR_{7b}$;

or, $U_1$ is N; $U_2$ is C; V is $CR_7$; $V_1$ is N or $CR_{7a}$; $V_2$ is N or $CR_{7b}$;

$R_1$, $R_2$, U, X, $X_1$, $X_2$, $R_6$, $R_7$, $R_{7a}$ and $R_{7b}$ are as defined above.

In some embodiments, $U_1$ and $U_2$ are C respectively; V is $NR_6$; $V_1$ is N or $CR_{7a}$; $V_2$ is N or $CR_{7b}$.

U is N; $R_6$ is pyrrolyl, pyrazolyl or isoxazolyl; the pyrrolyl, pyrazolyl or isoxazolyl is unsubstituted or optionally substituted at any position by 1 to 3 of the following substituents selected from halogen, cyano, $—R_c$, $—OR_c$, $—NR_cR_d$, $—N(CN)R_c$, $—N(OR_d)R_c$, $—S(O)_{0-2}R_c$, $—C(O)R_c$, $—C(O)OR_c$, $—C(O)NR_cR_d$, $—C(NH)NR_cR_d$, $—NR_dC(O)R_c$, $—NR_dC(O)NR_cR_d$, $—NR_dS(O)_2R_c$ and $—OC(O)R_c$;

$R_{7a}$ and $R_{7b}$ are each independently hydrogen;

$R_c$ and $R_d$ are each independently hydrogen or $C_{1-6}$ alkyl.

In some embodiments, the compound of formula (I), the stereoisomer or the pharmaceutically acceptable salt thereof is a compound of formula (IIA), a stereoisomer or a pharmaceutically acceptable salt thereof:

(IIA)

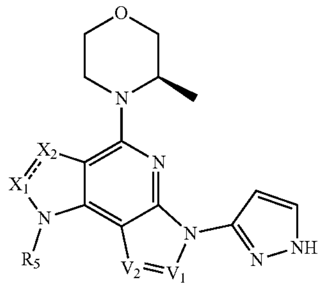

wherein, ⎓ is a double bond or a single bond;

$X_1$, $X_2$, $V_1$, $V_2$ and $R_5$ are defined as above.

In some embodiments, $X_1$ and $X_2$ are each independently N or CH.

In some embodiments, $X_1$ and $X_2$ are each independently $CH_2$.

In some embodiments, $V_1$ and $V_2$ are each independently N or CH.

In some embodiments, $R_5$ is $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, $—S(O)_{1-2}R_a$, $—S(O)_2NR_aR_b$, $—S(O)(═NCN)R_a$ or $—S(O)(═NR_b)R_a$; wherein, the $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, or 3- to 8-membered heterocycloalkyl-$C_{1-6}$ alkyl is unsubstituted or optionally substituted at any position by 1 to 3 of the following substituents selected from halogen, —CN, —$SR_a$, —$OR_a$, —C(O)$OR_a$, —C(O)$R_a$, —C(O)$NR_aR_b$, —$NR_aR_b$, —$NR_bC(O)R_a$, —$NR_bS(O)_2R_a$, —$S(O)_{1-2}R_a$, —$S(O)_2NR_aR_b$, —S(O)(═NCN)$R_a$ and —S(O)(═$NR_b$)$R_a$;

each $R_a$ is independently hydrogen or $C_{1-6}$ alkyl; the $C_{1-6}$ alkyl is unsubstituted or optionally substituted at any position by 1 to 3 of the following substituents selected from halogen, hydroxyl, amino, $C_{1-6}$ alkoxy, $C_{1-6}$ alkylamino, halo $C_{1-6}$ alkyl and halo $C_{1-6}$ alkoxy;

each $R_b$ is independently hydrogen or $C_{1-6}$ alkyl.

In some embodiments, the compound of formula (I), the stereoisomer or the pharmaceutically acceptable salt thereof is a compound of formula (III), a stereoisomer or a pharmaceutically acceptable salt thereof:

(III)

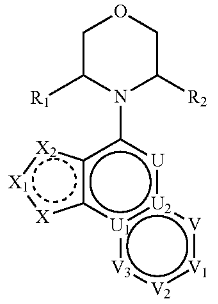

wherein, $U_1$ and $U_2$ are each independently C; V is $CR_7$; $V_1$ is N or $CR_{7a}$; $V_2$ is N or $CR_{7b}$; $V_3$ is N or $CR_{7c}$; $R_1$, $R_2$, U, X, $X_1$, $X_2$, $R_7$, $R_{7a}$, $R_{7b}$ and $R_{7c}$ are as defined above.

In some embodiments, U is N; $R_7$ is pyrrolyl, pyrazolyl or isoxazolyl; the pyrrolyl, pyrazolyl or isoxazolyl is unsubstituted or optionally substituted at any position by 1 to 3 of the following substituents selected from halogen, cyano, —$R_c$, —$OR_c$, —$NR_eR_d$, —N(CN)$R_c$, —N($OR_d$)$R_1$, —$S(O)_{0-2}R_c$, —C(O)$R_c$, —C(O)$OR_c$, —C(O)$NR_cR_d$, —C(NH)$NR_cR_d$, —$NR_dC(O)R_c$, —$NR_dC(O)NR_cR_d$, —$NR_dS(O)_2R_c$ and —OC(O)$R_c$;

$R_{7a}$, $R_{7b}$ and $R_{7c}$ are each independently hydrogen;

$R_c$ and $R_d$ are each independently hydrogen or $C_{1-6}$ alkyl.

In some embodiments, the compound of formula (I), the stereoisomer or the pharmaceutically acceptable salt thereof is a compound of formula (IIIA), a stereoisomer or a pharmaceutically acceptable salt thereof:

(IIIA)

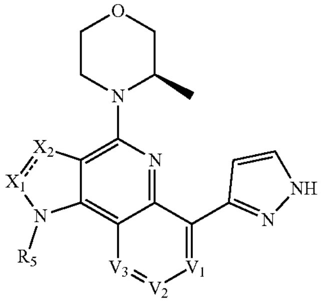

wherein, ⎓ is a double bond or a single bond;

$X_1$, $X_2$, $V_1$, $V_2$, $V_3$ and $R_5$ are as defined above.

In some embodiments, $X_1$ and $X_2$ are each independently N or CH.

In some embodiments, $X_1$ and $X_2$ are each independently $CH_2$.

In some embodiments, $V_1$, $V_2$ and $V_3$ are each independently N or CH.

In some embodiments, $V_1$ is N; $V_2$ and $V_3$ are each independently CH.

In some embodiments, $R_5$ is $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, —$S(O)_{1-2}R_a$, —$S(O)_2NR_aR_b$, —S(O)(═NCN)$R_a$ or —S(O)(═$NR_b$)$R_a$; wherein, the $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, or 3- to 8-membered heterocycloalkyl-$C_{1-6}$ alkyl is unsubstituted or optionally substituted at any position by 1 to 3 of the following substituents selected from halogen, —CN, —$SR_a$, —$OR_a$, —C(O)$OR_a$, —C(O)$R_a$, —C(O)$NR_aR_b$, —$NR_aR_b$, —$NR_bC(O)R_a$, —$NR_bS(O)_2R_a$, —$S(O)_{1-2}R_a$, —$S(O)_2NR_aR_b$, —S(O)(═NCN)$R_a$ and —S(O)(═$NR_b$)$R_a$;

each $R_a$ is independently hydrogen or $C_{1-6}$ alkyl; the $C_{1-6}$ alkyl is unsubstituted or optionally substituted at any position by 1 to 3 of the following substituents selected from halogen, hydroxyl, amino, $C_{1-6}$ alkoxy, $C_{1-6}$ alkylamino, halo $C_{1-6}$ alkyl and halo $C_{1-6}$ alkoxy;

each $R_b$ is independently hydrogen or $C_{1-6}$ alkyl.

In some embodiments, the compound of formula (I), the stereoisomer or the pharmaceutically acceptable salt thereof is optionally the following compound:

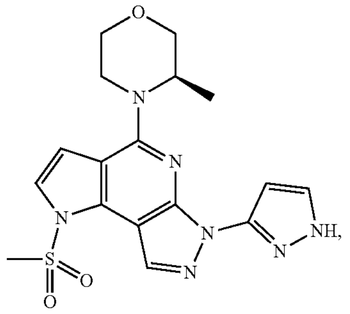

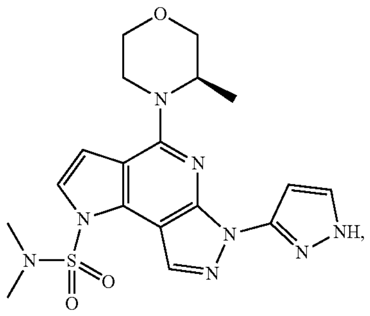

-continued
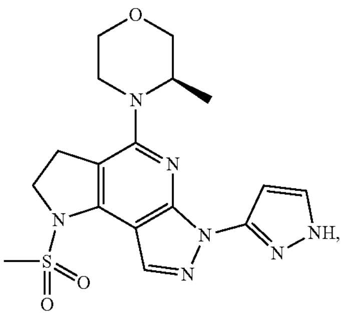
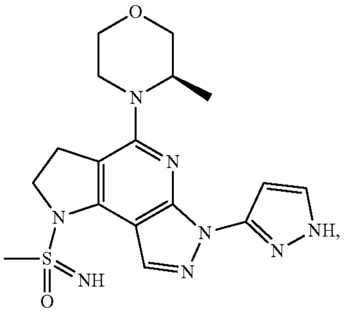
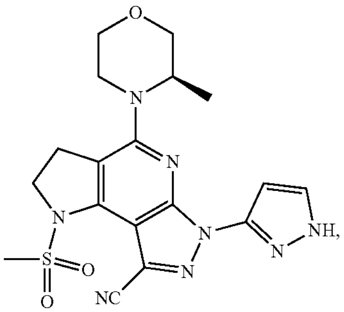
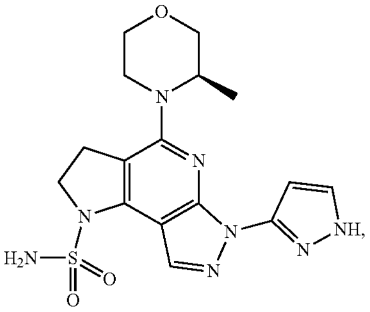
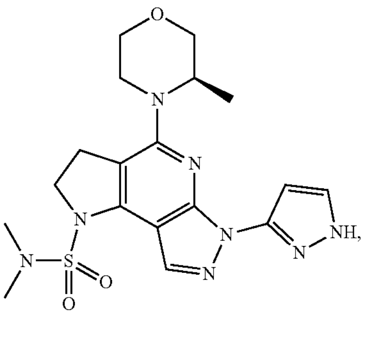
-continued
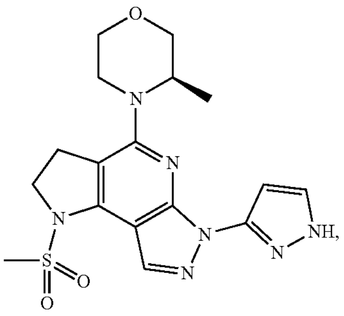
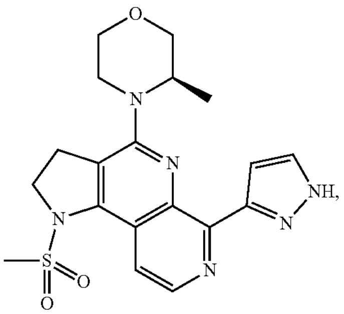
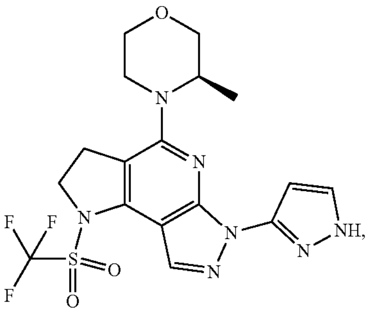
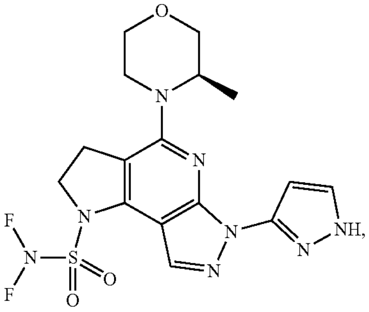
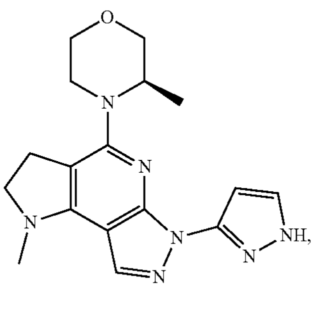

-continued
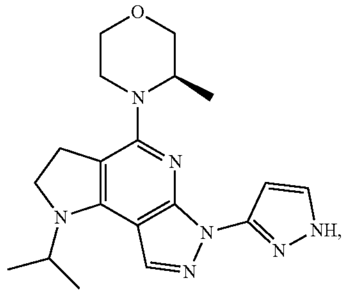
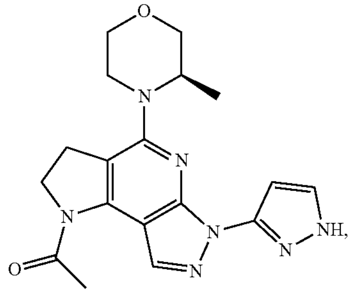
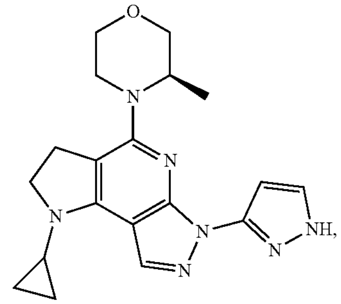
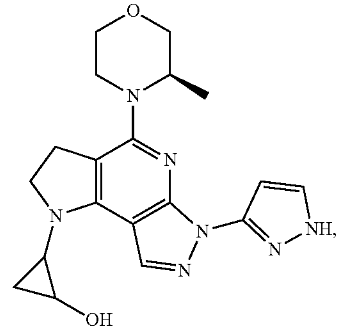
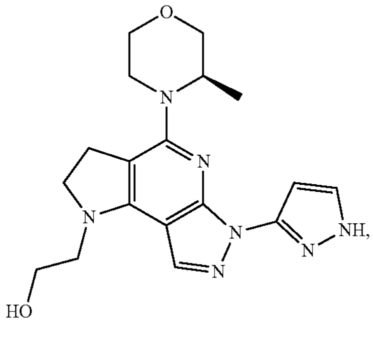
-continued
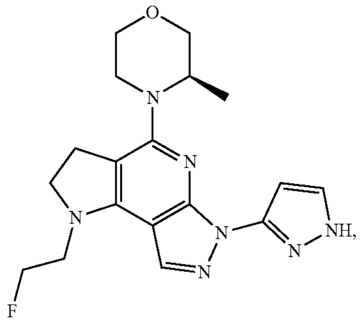
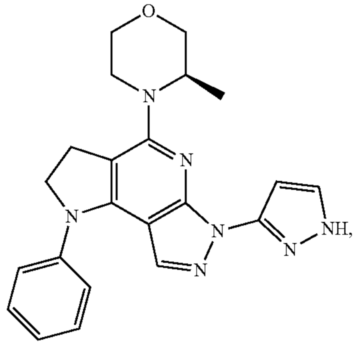
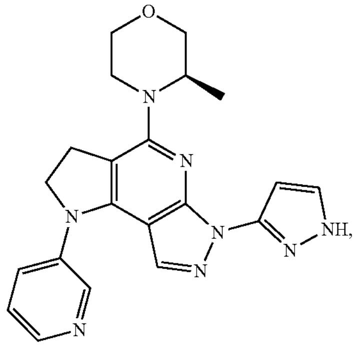
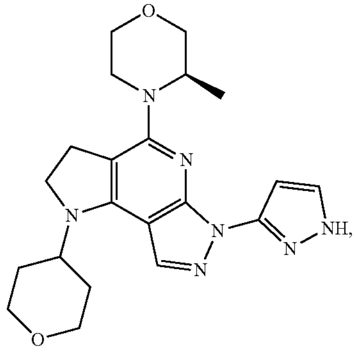

-continued
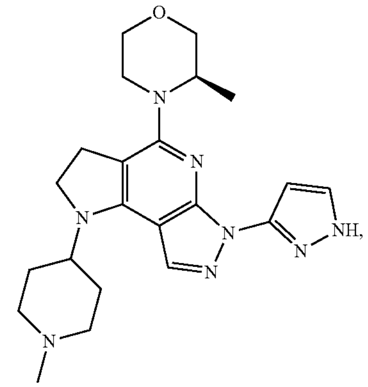
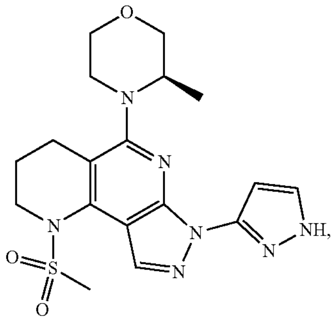
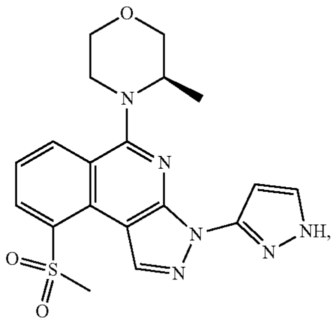
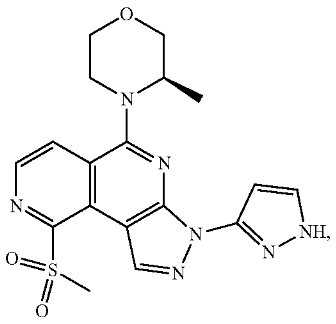
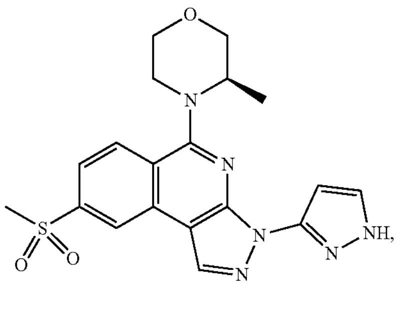
-continued
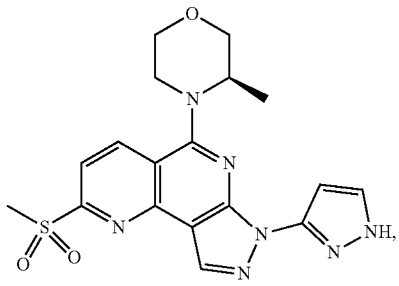
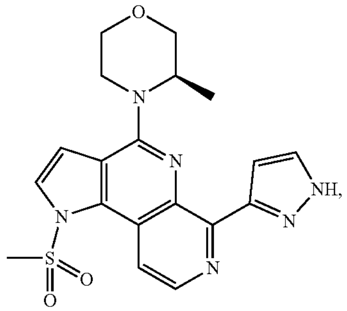
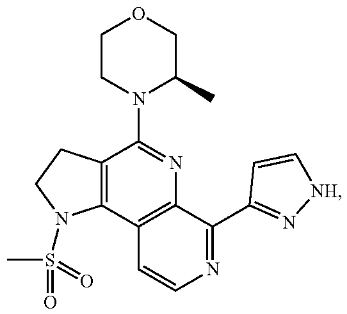
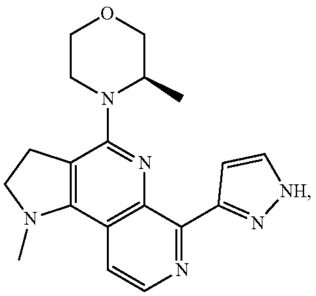
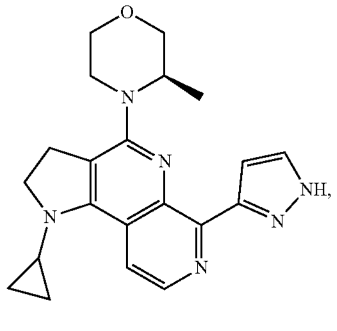

-continued

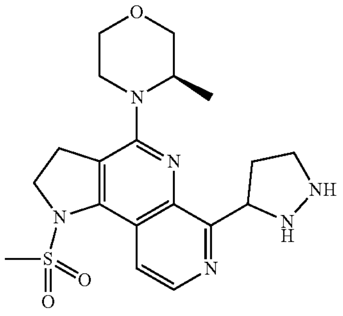

or

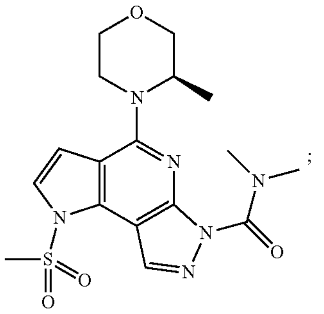

or a pharmaceutically acceptable salt thereof.

The present disclosure also provides a preparation method for the compound of formula (I), the stereoisomer or the pharmaceutically acceptable salt thereof, which is any one of the following methods:

Method 1:

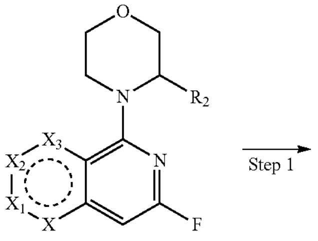

IV-1

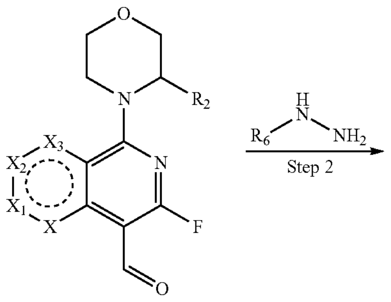

IV-2

-continued

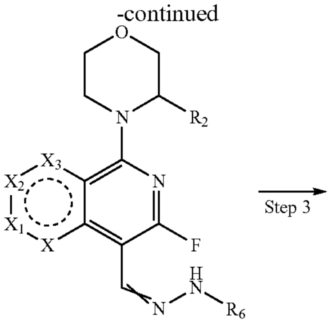

IV-3

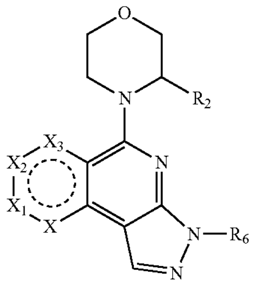

IV

In method 1, the definitions of X, $X_1$, $X_2$, $X_3$, $R_2$ and $R_6$ are as defined above. Step 1: In a solvent (e.g.: N,N-dimethylformamide), reacting IV-1 under the action of phosphorus oxychloride to obtain IV-2; or reacting IV-1 under a system of urotropine/trifluoroacetic acid to obtain IV-2. Step 2: In a solvent (e.g.: ethanol), reacting IV-2 with a suitable organic hydrazine (e.g.: heteroarylhydrazine) to obtain IV-3. Step 3: In a solvent (e.g.: N-methylpyrrolidone), carrying out a ring-closure reaction by IV-3 under high temperature conditions to obtain a compound of formula IV.

Method 2:

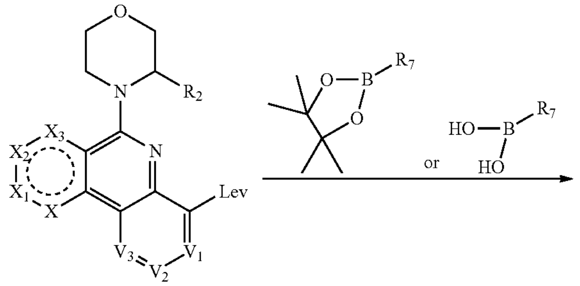

V-1

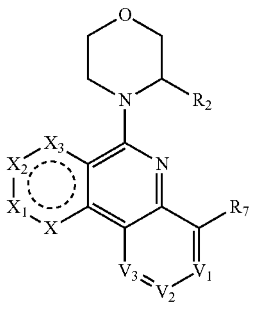

V

In method 2, Lev is a leaving group, preferably halogen, more preferably chlorine and bromine; the definitions of X, $X_1$, $X_2$, $X_3$, $V_1$, $V_2$, $V_3$, $R_2$ and $R_7$ are as defined above. In a solvent (e.g.: 1,4-dioxane/water), under alkaline conditions (e.g.: potassium carbonate, sodium carbonate or cesium carbonate), in the presence of a catalyst (e.g.: [1,1'-bis(diphenylphosphino)ferrocene]dichloropalladium), carrying out a coupling reaction by V-1 to obtain a compound of formula V.

Method 3:

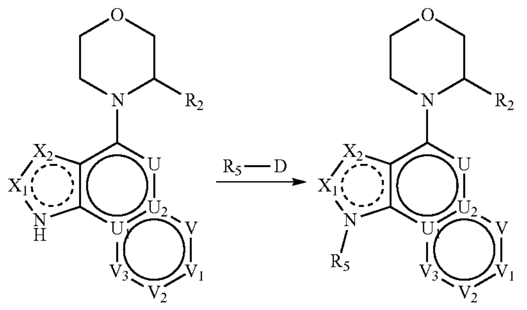

VI-1 VI

In method 3, the definitions of $X_1$, $X_2$, V, $V_1$, $V_2$, $V_3$, U, $U_1$, $U_2$, $R_2$ and $R_5$ are as defined above.

1) When $R_5$ is substituted or unsubstituted $C_{1-6}$ alkyl, substituted or unsubstituted $C_{3-8}$ cycloalkyl-$C_{1-6}$ alkyl, substituted or unsubstituted 3- to 8-membered heterocycloalkyl-$C_{1-6}$ alkyl, substituted or unsubstituted 5- to 6-membered heteroaryl-$C_{1-6}$ alkyl, —$S(O)_{1-2}R_a$ or —$S(O)_2NR_aR_b$, D is halogen (preferably chlorine, bromine or iodine); the compound of formula VI is obtained from VI-1 and $R_5$-D through a nucleophilic substitution reaction under alkaline conditions.

2) When $R_5$ is substituted or unsubstituted phenyl or substituted or unsubstituted 5- to 6-membered heteroaryl, D is halogen (preferably chlorine or bromine); in the presence of a catalyst (e.g.: methanesulfonato(2-dicyclohexylphosphino-2',6'-di-i-propoxy-1,1'-biphenyl) (2'-amino-1,1'-biphenyl-2-yl)palladium(II)), the compound of formula VI is obtained from VI-1 and $R_5$-D through a coupling reaction.

3) When $R_5$ is substituted or unsubstituted $C_{3-8}$ cycloalkyl or substituted or unsubstituted 3- to 8-membered heterocycloalkyl, D is a boronic acid group or a borate ester group; under alkaline conditions (e.g.: sodium carbonate or potassium carbonate), in the presence of a catalyst (e.g.: copper acetate), the compound of formula VI is obtained from VI-1 and $R_5$-D through a coupling reaction.

In the above method 1, 2 or 3, when there is an amino group, a hydroxyl group or a carboxyl group in X, $X_1$, $X_2$, $X_3$, V, $V_1$, $V_2$, $V_3$, —$R_5$, —$R_6$ or —$R_7$, the amino group, hydroxyl group or carboxyl group can be protected by protecting groups to avoid any side reactions. If the above-mentioned amino protecting group, hydroxyl protecting group or carboxyl protecting group exists, a subsequent deprotection step is required to obtain the compound of formula IV, V or VI. Any suitable amino protecting group, such as tert-butoxycarbonyl (Boc) group or benzyloxycarbonyl (Cbz) group, can be used to protect the amino group. If Boc is used as a protecting group, the subsequent deprotection reaction can be carried out under standard conditions, for example, p-toluenesulfonic acid/methanol system, dichloromethane/trifluoroacetic acid system, organic solution system of hydrogen chloride (organic solution includes, but is not limited to: ether solution, 1,4-dioxane solution, methanol solution, ethanol solution, isopropanol solution) or trimethylsilyl trifluoromethanesulfonate/2,6-lutidine/dichloromethane system; the Cbz protecting group can be deprotected using palladium on carbon/hydrogen system. Any suitable hydroxyl protecting group, for example: benzyl, methoxymethyl (MOM), 2-tetrahydropyranyl (THP), (trimethylsilyl)ethoxymethyl (SEM), organosilicon groups (including but not limited to: tert-butyldimethylsilyl, trimethylsilyl) can be used as hydroxyl protecting groups, and the subsequent deprotection reaction can be carried out under standard conditions. For example, benzyl can be treated with palladium on carbon/hydrogen system for deprotection; MOM protecting group can be treated with hydrogen chloride organic solution system (organic solution includes, but is not limited to: ether solution, 1,4-dioxane solution, methanol solution, ethanol solution, isopropanol solution) for deprotection; THP protecting group and SEM protecting group can be treated with trifluoroacetic acid/dichloromethane system for deprotection; organosilicon group can be treated with tetrabutylammonium fluoride/tetrahydrofuran system for deprotection. Any suitable carboxyl protecting group, for example: forming a carboxylate group (e.g., methyl carboxylate, ethyl carboxylate), can be used to protect the carboxyl group, and subsequent deprotection can be performed under standard conditions, for example, NaOH, KOH, LiOH in tetrahydrofuran, water and/or methanol solvents for deprotection. The above deprotection reaction is preferably carried out in the last step.

The pharmaceutically acceptable salt of the triheterocyclic derivative (I) can be synthesized by general chemical methods.

In general, salts can be prepared by reacting free bases or acids with equivalent or excess amounts of acids (inorganic or organic) or bases (inorganic or organic) in a suitable solvent or solvent composition.

The present disclosure also provides a pharmaceutical composition, comprising a therapeutically effective amount of an active component and a pharmaceutically acceptable excipient; the active component comprises one or more of the triheterocyclic derivatives (I), the stereoisomers or the pharmaceutical salts thereof.

In the pharmaceutical composition, the active component may also comprise other therapeutic agents for related diseases caused by abnormal ATR levels.

In the pharmaceutical composition, the pharmaceutically acceptable excipient may comprise a pharmaceutically acceptable carrier, diluent and/or excipient.

According to the purpose of treatment, the pharmaceutical composition can be made into various types of administration unit dosage forms, such as tablets, pills, powders, liquids, suspensions, emulsions, granules, capsules, suppositories and injections (solutions and suspensions), preferably liquids, suspensions, emulsions, suppositories and injections (solutions and suspensions).

To shape the pharmaceutical composition in the form of the tablet, any excipient known and widely used in the art may be used. For example, carriers such as lactose, white sugar, sodium chloride, glucose, urea, starch, calcium carbonate, kaolin, crystalline cellulose and silicic acid; binders such as water, ethanol, propanol, common syrup, glucose solution, starch solution, gelatin solution, carboxymethylcellulose, shellac, methylcellulose, potassium phosphate and polyvinylpyrrolidone; disintegrants, such as dry starch, sodium alginate, agar powder and kelp powder, sodium bicarbonate, calcium carbonate, fatty acid ester of polyethylene dehydrated sorbitol, dodecyl $Na_2SO_4$, glycerol monostearate, starch and lactose; disintegration inhibitors, such as white sugar, glycerol tristearate, coconut oil and hydrogenated oil; adsorption promoters, such as quaternary amine base and dodecyl $Na_2SO_4$; wetting agents, such as glycerin, starch; adsorbents, such as starch, lactose, kaolin, bentonite and colloidal silicic acid; and lubricants, such as pure talc, stearate, boric acid powder and polyethylene glycol. Common coating materials can also be selected to make sugar-coated tablets, gelatin-coated film tablets, enteric-coated tablets, film-coated tablets, double-layer film tablets and multi-layer tablets according to needs.

To shape the pharmaceutical composition in the form of the pill, any known and widely used excipients in the art may be used, for example, carriers such as lactose, starch, coconut oil, hardened vegetable oil, kaolin and talc; binders, such as gum arabic powder, tragacanth powder, gelatin and ethanol; disintegrants, such as agar and kelp powder.

To shape the pharmaceutical composition in form of the suppository, any known and widely used excipients in the art may be used, for example, polyethylene glycol, coconut oil, higher alcohol, esters of high alcohol, gelatin and semi-synthetic glyceride.

To prepare the pharmaceutical composition in the form of the injection, the solution or suspension can be sterilized (preferably adding an appropriate amount of sodium chloride, glucose or glycerol, etc.) to make an injection with isotonic pressure with blood. When preparing injections, any carrier commonly used in the art can also be used. For example, water, ethanol, propylene glycol, ethoxylated isostearyl alcohol, polyoxylated isostearyl alcohol, fatty acid ester of polyethylene dehydrated sorbitol. In addition, common dissolving agents, buffers, analgesics and the like can also be added.

In the present disclosure, the content of the composition in the pharmaceutical composition is not particularly limited, and can be selected in a wide range, usually 5-95% by mass, preferably 30-80% by mass.

In the present disclosure, the administration method of the pharmaceutical composition is not particularly limited. According to the patient's age, gender and other conditions and symptoms, various dosage forms of preparations can be selected for administration. For example, tablets, pills, solutions, suspensions, emulsions, granules or capsules are administered orally; injections can be administered alone, or mixed with injection delivery liquids (such as glucose solution and amino acid solution) for intravenous injection; suppositories are administered to the rectum.

The present disclosure also provides a use of the triheterocyclic derivative (I), the stereoisomer or the pharmaceutically acceptable salt thereof, or the pharmaceutical composition in the manufacture of an ATR inhibitor. The ATR inhibitor is capable of inhibiting the activity or expression of ATR (including the abnormal activity or overexpression of ATR).

The triheterocyclic derivative (I), the stereoisomer or the pharmaceutically acceptable salt thereof, or the pharmaceutical composition provided by the present disclosure has the effects of resisting tumor cell proliferation, promoting tumor cell apoptosis and/or resisting tumor cell invasion. The effect of promoting tumor cell apoptosis is realized by inhibiting ATR activity.

The present disclosure also provides a use of the triheterocyclic derivative (I), the stereoisomer or the pharmaceutically acceptable salt thereof, or the pharmaceutical composition in the manufacture of a medicament for treating, alleviating and/or preventing a related disease mediated by ATR.

The present disclosure also provides a use of the triheterocyclic derivative (I), the stereoisomer or the pharmaceutically acceptable salt thereof, or the pharmaceutical composition in the manufacture of a medicament for treating and/or alleviating cancer.

The present disclosure also provides a use of the triheterocyclic derivative (I), the stereoisomer or the pharmaceutically acceptable salt thereof, or the pharmaceutical composition in the manufacture of a medicament with antiproliferative effect in mammals.

The present disclosure also provides a use of the triheterocyclic derivative (I), the stereoisomer or the pharmaceutically acceptable salt thereof, or the pharmaceutical composition in the manufacture of a medicament with pro-apoptotic effects in mammals.

The present disclosure also provides a use of the triheterocyclic derivative (I), the stereoisomer or the pharmaceutically acceptable salt thereof, or the pharmaceutical composition in the manufacture of a medicament with resisting cancer cell invasion effects in mammals.

The present disclosure also provides a use of the triheterocyclic derivative (I), the stereoisomer thereof or the pharmaceutically acceptable salt thereof, or the pharmaceutical composition in treating and/or alleviating cancer, comprising administering to a mammal a therapeutically effective amount of the compound of formula (I), the stereoisomer or the pharmaceutically acceptable salt thereof, or the pharmaceutical composition comprising the compound of formula (I), the stereoisomer or the pharmaceutically acceptable salt thereof.

The present disclosure also provides the triheterocyclic derivative (I), the stereoisomer or the pharmaceutically acceptable salt thereof, or the pharmaceutical composition for use in combination with one or more other kinds of therapeutic agents and/or treatment methods for treating, alleviating and/or preventing a related disease mediated by ATR.

In the present disclosure, the related disease mediated by ATR is a related disease caused by abnormal ATR levels, preferably a proliferation disease, more preferably cancer.

In the present disclosure, the other kinds therapeutic agents for the related disease mediated by ATR are preferably other kinds of therapeutic agents for treating cancer.

In the present disclosure, the other kinds of therapeutic agents for treating cancer can be formulated with the triheterocyclic derivative (I) in a single administration dosage form, or in a sequential administration dosage form.

In the present disclosure, the other kinds of therapeutic agents for treating cancer may include, but are not limited to, one or more of: alkylating agents, topoisomerase I/II inhibitors, anti-mitotic agents, anti-metabolite drugs, hormones and hormone analogs, anti-tumor antibiotics, small molecule kinase inhibitors, small molecule immunomodulators, interferons, aromatase inhibitors, PARP inhibitors, anti-tumor vaccines, cytokines, chimeric antigen receptor T cells (CAR-T), monoclonal antibodies and radiotherapy.

In the present disclosure, the alkylating agent may be selected from but not limited to one or more of: cisplatin, carboplatin, oxaliplatin, nedaplatin, nitrogen mustard, N-oxide-nitrogen mustard hydrochloride, cyclobutyric acid nitrogen mustard, uracil nitrogen mustard, cyclophosphamide, isocyclophosphamide, thiotepa, carboquone, triaziquone, improsulfan tosylate, mannosulfan, treosulfan, busulfan, nimustine hydrochloride, dibromomannitol, melphalan, dacarbazine, ranimustine, carmustine, lomustine, streptozocin, temozolomide, procarbazine, ethyleneimine derivatives, methanesulfonates, nitrosoureas, triazenes.

In the present disclosure, the topoisomerase I/II inhibitor can be selected from but not limited to one or more of doxorubicin, daunorubicin, epirubicin, idarubicin, irinotecan, topotecan, rubitecan, belotecan, etoposide, teniposide, adriamycin, dexrazoxane, camptothecin.

In the present disclosure, the anti-mitotic agent includes, but is not limited to, one or more of paclitaxel, docetaxel, paclitaxel poliglumex, leurosidine, vincristine, vinblastine, vindesine, vinzolidine, etoposide, teniposide, ixabepilone, larotaxel, ortataxel, tesetaxel, tocosal and ispinesib.

In the present disclosure, the anti-metabolite drug may be selected from but not limited to one or more of folic acid antagonists, pyrimidine analogs, purine analogs, adenosine deaminase inhibitors, for example: methotrexate, 5-fluorouracil, floxuridine, cytarabine, 6-mercaptopurine, 6-thioguanine, fludarabine phosphate, pentostatin and gemcitabine.

In the present disclosure, the hormone therapy agent can be selected from but not limited to one or more of fosfestrol, diethylstilbestrol, chlorotrisin, medroxyprogesterone acetate, megestrol acetate, chlormadinone acetate, cyproterone acetate, danazol, dienogest, allylestrenol, gestrinone, nomegestrol, tadenan, mepartricin, raloxifene, ormeloxifene, levormeloxifene, aminoglutethimide, testolactone, anti-estrogens, LH-RH derivatives, aromatase inhibitors, anti-androgens, adrenal corticosteroids, androgen synthesis inhibitors, retinoic acid and drugs that delay retinoic acid metabolism.

In the present disclosure, the anti-tumor antibiotic includes, but is not limited to, one or more of actinomycin D, doxorubicin, daunorubicin, bleomycin, peplomycin, mitomycin C, aclarubicin, pirarubicin, epirubicin, zinostatin stimalamer, idarubicin, sirolimus and valrubicin.

In the present disclosure, the small molecule kinase inhibitor includes, but is not limited to, one or more of erlotinib, imatinib, apatinib, nilotinib, crizotinib, dasatinib, pazopanib, regorafenib, ruxolitinib, sorafenib, sunitinib, vandetanib, vemurafenib, bosutinib, gefitinib, afatinib, axitinib, dabrafenib, dacomitinib, nintedanib, lenvatinib, masitinib, midostaurin, neratinib, ponatinib, radotinib, trametinib, brivanib alaninate, cediranib, cabozantinib malate, ibrutinib, icotinib, cipatinib, cobimetinib, idelalisib, ponatinib, alisertib, dinaciclib, linsitinib, orantinib, rigosertib, tipifarnib, tivozanib, pimasertib, buparlisib, and fedratinib.

In the present disclosure, the anti-tumor vaccine includes, but is not limited to, one or more of synthetic peptides, DNA vaccines and recombinant viruses.

In the present disclosure, the cytokine therapy includes, but is not limited to: IL2 and GM-CSF.

In the present disclosure, the monoclonal antibody includes, but are not limited to, one or more of: alemtuzumab, brentuximab, cetuximab, rituximab, denosumab, ipilimumab, ofatumumab, panitumumab, tositumomab, trastuzumab, bevacizumab, pertuzumab, catumaxomab, elotuzumab, epratuzumab, necitumumab, nimotuzumab, tocilizumab, matuzumab, zalutumumab, atezolizumab, ramucirumab, nivolumab, mogamulizumab, ocaratuzumab, oregovomab, dalotuzumab, onartuzumab.

In the present disclosure, the small molecule immunomodulator includes, but is not limited to, one or more of: TLR7 agonists, TLR8 agonists, TLR9 agonists, IDO inhibitors, CD73 inhibitors, STING inhibitors, and A2AR antagonists.

In the present disclosure, the interferon used for treating cancer includes, but is not limited to, one or more of: interferon $\alpha$, interferon $\alpha$-2a, interferon $\alpha$-2b, interferon $\beta$, interferon $\gamma$-1a or interferon $\gamma$-n1, etc.

In the present disclosure, the aromatase inhibitor includes, but is not limited to, one or more of: anastrozole, aminoglutethimide, exemestane, fadrozole and letrozole.

In the present disclosure, the PARP inhibitor includes, but is not limited to, one or more of: olaparib, niraparib, rucaparib, veliparib and SC10914.

In the present disclosure, the cancer includes metastatic and non-metastatic cancers, hereditary and sporadic cancers, solid tumors and non-solid tumors.

In the present disclosure, specific examples of the solid tumor may include, but are not limited to: eye, bone, lung, stomach, pancreas, breast, prostate, brain (including glioblastoma and medulloblastoma), ovary (including those stromal cells arising from epithelial cells, germ cells and stromal cells), bladder, testis, spinal cord, kidney (including adenocarcinoma, nephroblastoma), mouth, lip, throat, oral cavity (including squamous cell carcinoma), nasal cavity, small intestine, colon, rectum, parathyroid gland, gallbladder, bile duct, cervix, heart, hypopharyngeal gland, bronchi, liver, ureter, vagina, anus, laryngeal gland, thyroid gland (including thyroid and medullary carcinoma), esophagus, nasopharyngeal adenohypophysis, salivary gland, adrenal gland, head and neck intraepithelial neoplasia (including Bowen's disease and Paget's disease), sarcoma (including leiomyosarcoma, rhabdomyosarcoma, liposarcoma, fibrosarcoma, osteosarcoma), skin (including melanoma, Kaposi's sarcoma, basocellular carcinoma and squamous cell carcinoma) and other related tumors.

In the present disclosure, the solid tumor is preferably human eye cancer, bone cancer, gastric cancer, pancreatic cancer, breast cancer, prostate cancer, brain cancer (including but not limited to malignant glioma, medulloblastoma), ovarian cancer, bladder cancer, cervical cancer, testicular cancer, kidney cancer (including but not limited to adenocarcinoma, nephroblastoma), oral cancer (including squamous cell carcinoma), tongue cancer, laryngeal cancer, nasopharyngeal cancer, head and neck cancer, colon cancer, intestinal carcinoma, rectal cancer, parathyroid cancer, thyroid cancer, esophageal cancer, gallbladder cancer, bile duct cancer, cervical cancer, liver cancer, lung cancer (including but not limited to small cell lung cancer, non-small cell lung cancer), chorionic epithelioma, osteosarcoma, Ewing's tumor, soft tissue sarcoma and skin cancer.

In the present disclosure, specific examples of the non-solid tumor (including hematological tumors) include, but are not limited to, one or more of: lymphoid leukemia (including lymphoblastic leukemia, lymphoma, myeloma, chronic lymphocytic leukemia (T-cell chronic lymphocytic leukemia, B-cell chronic lymphocytic leukemia), Hodgkin's lymphoma, non-Hodgkin's lymphoma), myeloid-related leukemia (including acute myeloid leukemia, chronic myeloid leukemia) and AIDs-related leukemia.

In the present disclosure, the cancer is preferably one or more of the following: non-small cell lung cancer, small cell lung cancer, gastric cancer, esophageal cancer, melanoma, colon cancer, pancreatic cancer, breast cancer, uterine cancer, ovarian cancer, prostate cancer, brain cancer, bladder cancer, kidney cancer, myeloma, liver cancer, acute myeloid leukemia, chronic myeloid leukemia, lymphoblastic leukemia, chronic lymphocytic leukemia and lymphoma.

In the present disclosure, the mammal is preferably a human.

In the present disclosure, the "tumor" and "cancer" have the same meaning.

In the present disclosure, unless otherwise stated, the term "substituted at any position by one or more groups" means that any one or more hydrogen atoms of one or more atoms specified on the group are substituted by the specified group, provided that the normal valence of the specified atom is not exceeded, and the substitutions are all reasonable substitutions common in the art. For example: $R_a$ is optionally substituted at any position by 1 to 3 groups, which means that $R_a$ can be reasonably substituted at any position by 1, 2 or 3 identical or different substituents.

In the present disclosure, any combination of variables is allowed only if such combination results in a stable compound; for example, V is $NR_6$ or $CR_7$; $V_1$ is N, $NR_{6a}$ or $CR_{7a}$; $V_2$ is N, $NR_{6b}$ or $CR_{7b}$; when $V_3$ is a bond, N, $NR_{6b}$ or $CR_{7b}$, V, $V_1$, $V_2$ and $V_3$ include any of the following stable combinations: 1) V is $NR_6$, $V_1$ is N or $CR_{7a}$, $V_2$ is N or $CR_{7b}$, $V_3$ is a bond; 2) V is $CR_7$, $V_1$ is N or $CR_{7a}$, $V_2$ is N or $CR_{7b}$, $V_3$ is a bond; 3) V is $CR_7$, $V_1$ is N or $CR_{7a}$, $V_2$ is N or $CR_{7b}$, $V_3$ is N or $CR_{7c}$; 4) V is $CR_7$, $V_1$ is N or $CR_7$a, $V_2$ is $NR_{6b}$, and $V_3$ is a bond; or 5) V is $CR_7$, $V_1$ is $NR_{6a}$, $V_2$ is N or $CR_{7b}$, and $V_3$ is a bond.

In the present disclosure, when any variable occurs more than once in the composition or structure of a compound, its definition is independent in each case.

In the present disclosure, unless otherwise stated,

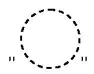

is included in the cyclic group, indicating that the cyclic group is an aromatic ring or a non-aromatic ring;

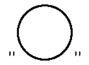

is included in the cyclic group, indicating that the cyclic group is an aromatic ring. For example: the group

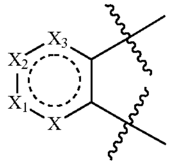

is a 5- to 6-membered aromatic ring or a 5- to 6-membered non-aromatic ring; the definitions of X, $X_1$, $X_2$ and $X_3$ are as described above. The group

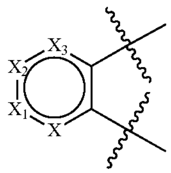

is a 5- to 6-membered aromatic ring; the definitions of X, $X_1$, $X_2$ and $X_3$ are as described above.

Unless otherwise stated, the following terms appearing in the present specification and claims have the following meanings:

The term "alkyl" refers to a saturated straight-chain or branched-chain hydrocarbon group comprising 1-20 carbon atoms, preferably 1-10 carbon atoms, more preferably 1-8, 1-6 or 1-4 carbon atoms, representative alkyl examples include, but are not limited to: methyl, ethyl, n-propyl, isopropyl, n-butyl, sec-butyl, tert-butyl, isobutyl, n-pentyl, n-hexyl, n-heptyl, octyl, nonyl, decyl, 1,1-dimethylpropyl, 1,2-dimethylpropyl, 2,2-dimethylpropyl, 1-ethylpropyl, 2-methylbutyl, 3-methylbutyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2,3-dimethylbutyl, 2-ethylbutyl, 2-methylpentyl, 3-methylpentyl, 4-methylpentyl, 4,4-dimethylpentyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, 2,2,4-trimethylpentyl, undecyl, dodecyl, and their various isomers, etc.

The term "cycloalkyl" refers to a saturated or partially unsaturated (containing 1 or 2 double bonds) monocyclic or fused ring group containing 3-20 carbon atoms. "Monocycloalkyl" is preferably a 3- to 10-membered monocycloalkyl group, more preferably a 3- to 8- or 3- to 6-membered monocycloalkyl group. Examples of the cycloalkyl group include, but are not limited to: cyclopropyl, cyclobutyl, cyclopentyl, cyclohexyl, cycloheptyl, cyclooctyl, cyclodecyl, cyclododecyl, cyclohexenyl, 2,3-dihydro-1-H-indene, decahydronaphthalene, etc. The cycloalkyl group may be linked to the parent molecule through any carbon atom in the ring.

The term "heterocycloalkyl" refers to a saturated or partially unsaturated (containing 1 or 2 double bonds) 3- to 20-membered non-aromatic cyclic group composed of carbon atoms and heteroatoms selected from nitrogen, oxygen or sulfur, this cyclic group can be a single ring or a fused ring group. In the present disclosure, the number of heteroatoms in the heterocycloalkyl group is preferably 1, 2, 3 or 4, and the nitrogen, carbon or sulfur atom in the heterocycloalkyl group may optionally be oxidized. The nitrogen atom can optionally be further substituted with other groups to form tertiary amines or quaternary ammonium salts. The heterocycloalkyl group is preferably a 3- to 10-membered monocyclic heterocycloalkyl group, more preferably a 3- to 6-membered monocyclic heterocycloalkyl group. Examples of the heterocycloalkyl group include, but are not limited to: aziridinyl, tetrahydrofuran-2-yl, morpholin-4-yl, thiomorpholin-4-yl, thiomorpholin-S-oxide-4-yl, piperidin-1-yl, N-alkylpiperidin-4-yl, pyrrolidin-1-yl, N-alkylpyrrolidin-2-yl, piperazin-1-yl, 4-alkylpiperazin-1-yl, etc. The heterocycloalkyl group may be linked to the parent molecule through any ring atom in the ring. The aforementioned ring atoms specifically refer to carbon atoms and/or nitrogen atoms constituting the ring skeleton.

The term "non-aromatic group" or "non-aromatic ring" refers to "cycloalkyl" and/or "heterocycloalkyl", including the above definitions of cycloalkyl and/or heterocycloalkyl.

The term "cycloalkylalkyl" refers to a cycloalkyl group connected to a mother nucleus structure through an alkyl group. Thus, "cycloalkylalkyl" includes the above definitions of alkyl and cycloalkyl.

The term "heterocycloalkylalkyl" refers to a heterocycloalkyl group connected to a mother nucleus structure through an alkyl group. Thus, "heterocycloalkylalkyl" includes the above definitions of alkyl and heterocycloalkyl.

The term "alkoxy" refers to a cyclic or acyclic alkyl group having the stated number of carbon atoms linked through an oxygen bridge, including alkyloxy, cycloalkyloxy and heterocycloalkyloxy. Thus, "alkoxy" includes the above definitions of alkyl, heterocycloalkyl and cycloalkyl.

The term "alkenyl" refers to a straight-chain, branched-chain or cyclic non-aromatic hydrocarbon group comprising at least one carbon-carbon double bond. Where, there may be 1-3 carbon-carbon double bonds, preferably 1 carbon-carbon double bond. The term "$C_{2-4}$ alkenyl" refers to an alkenyl group with 2-4 carbon atoms, and the term "$C_{2-6}$ alkenyl" refers to an alkenyl group with 2-6 carbon atoms, including vinyl, propenyl, butenyl, 2-methylbutenyl and cyclohexenyl.

The term "alkynyl" refers to a straight-chain, branched-chain or cyclic hydrocarbon group comprising at least one carbon-carbon triple bond. Where, there may be 1-3 carbon-carbon triple bonds, preferably 1 carbon-carbon triple bond. The term "$C_{2-6}$ alkynyl" refers to an alkynyl group having 2 to 6 carbon atoms, including ethynyl, propynyl, butynyl and 3-methylbutynyl.

The term "aryl" refers to any stable 6- to 10-membered monocyclic or fused aromatic group, wherein at least one ring in the fused aromatic group is a benzene ring, and the remaining rings may be benzene ring, monocyclic cycloalkyl or monocyclic heterocycloalkyl. The aryl group includes, but is not limited to: phenyl, naphthyl, tetrahydronaphthyl, 2,3-dihydroindene, biphenyl, benzo[d][1,3]dioxolyl, indolinyl, isoindolinyl, 2,3-dihydrobenzofuranyl, 2,3-dihydrobenzo[b]thienyl, benzopyranyl, 1,2,3,4-tetrahydroquinolyl, 1,2,3,4-tetrahydroisoquinolyl, 2,2-dioxo-1,3-dihydrobenzo[c]isothiazolyl, 1,1-dioxo-dihydrobenzothiopyranyl, 1,1-dioxo-2,3-dihydrobenzo[b]thiophene, 1-imino-1-oxo-2,3-dihydrobenzo[b]thienyl, 2-oxo-2,3-dihydro-1H-benzo[d]imidazolyl.

The term "heteroaryl" refers to an aromatic ring group formed by replacing at least one ring's carbon atom with a heteroatom selected from nitrogen, oxygen or sulfur, which can be a 5- to 7-membered monocyclic structure or a 7- to 12-membered fused ring structure, wherein at least one ring in the fused ring structure is a heteroaryl group, and the remaining rings may optionally be aromatic ring, heteroaryl ring, cycloalkyl or heterocycloalkyl. In the present disclosure, the number of heteroatoms is preferably 1, 2, 3 or 4, and the nitrogen atom in the heteroaryl group can be optionally oxidized. The heteroaryl group is preferably a 5- to 10-membered heteroaryl group, including but not limited to: pyridyl, pyrimidinyl, pyrazinyl, pyridazin-3(2H)-keto, furyl, thienyl, thiazolyl, pyrrolyl, imidazolyl, pyrazolyl, oxazolyl, isoxazolyl, 1,2,5-oxadiazolyl, 1,2,4-oxadiazolyl, 1H-1,2,4-triazolyl, 4H-1,2,4-triazolyl, 1H-1,2,3-triazolyl, 1H-tetrazolyl, 1H-indazolyl, 1H-pyrazolo[3,4-b]pyridyl, 1H-pyrazolo[3,4-c]pyridyl, 1H-pyrazolo[4,3-c]pyridyl, 1H-indolyl, 1H-benzimidazolyl, 1H-benzofuryl, benzothienyl, benzothiazolyl, benzoxazolyl, quinolinyl, isoquinolyl, quinazolinyl, 1H-pyrrolo[3,2-c]pyridyl, 1H-pyrrolo[2,3-c]pyridyl, 1H-pyrrolo[2,3-b]pyridyl, 2,3-dihydro-1H-pyrrolo[2,3-c]pyridyl, 2,3-dihydro-1H-pyrrolo[2,3-b]pyridyl, 7H-pyrrolo[2,3-d]pyrimidinyl or 7-oxo-6,7-dihydro-1H-pyrrolo[2,3-c]pyridyl.

The term "aromatic group" or "aromatic ring" refers to "aryl" and/or "heteroaryl", including the above definitions of aryl and/or heteroaryl.

The term "arylalkyl" refers to an aryl group connected to a mother nucleus structure through an alkyl group. Thus, "arylalkyl" includes the above definitions of alkyl and aryl.

The term "heteroarylalkyl" refers to a heteroaryl group connected to a mother nucleus structure through an alkyl group. Thus, "heteroarylalkyl" includes the above definitions for alkyl and heteroaryl.

The term "halogen" refers to fluorine, chlorine, bromine or iodine.

The term "haloalkyl" refers to an alkyl group optionally substituted with halogen.

Thus, "haloalkyl" includes the above definitions of halogen and alkyl.

The term "haloalkoxy" refers to an alkoxy group optionally substituted with halogen.

Thus, "haloalkoxy" includes the above definitions of halogen and alkoxy.

The term "amino" refers to $—NH_2$, and the term "alkylamino" refers to an amino group wherein at least one hydrogen atom is substituted with an alkyl group, including but not limited to: $—NHCH_3$, $—N(CH_3)_2$, $—NHCH_2CH_3$, $—N(CH_2CH_3)_2$, $—N(CH_3)(CH_2CH_3)$. Thus, "alkylamino" includes the above definitions of alkyl and amino.

The term "nitro" refers to $—NO_2$.

The term "cyano" refers to —CN.

The term "carboxyl" refers to —C(O)OH.

The symbol "=" refers to a double bond.

The "room temperature" in the present disclosure refers to 15 to 30° C.

The "pharmaceutically acceptable salts" in the present disclosure are discussed in Berge, et al., "Pharmaceutically acceptable salts", J. Pharm. Sci., 66, 1-19 (1977), and it is obvious to medicinal chemists, such salts are substantially non-toxic and provide the desired pharmacokinetic properties, palatability, absorption, distribution, metabolism or excretion, etc. The compound of the present disclosure may have an acidic group, a basic group or an amphoteric group, and typical pharmaceutically acceptable salts include salts prepared by reacting the compound of the present disclosure with an acid, for example: hydrochloride, hydrobromide, sulfate, pyrosulfate, bisulfate, sulfite, bisulfite, phosphate, monohydric phosphate, dihydric phosphate, metaphosphate, pyrophosphate, nitrate, acetate, propionate, caprate, caprylate, formate, acrylate, isobutyrate, hexanoate, heptanoate, oxalate, malonate, succinate, suberate, benzoate, methylbenzoate, phthalate, maleate, mesylate, p-toluenesulfonate, (D, L)-tartaric acid, citric acid, maleic acid, (D, L)-malic acid, fumaric acid, succinic acid, succinate, lactate, triflate, naphthalene-1-sulfonate, mandelate, pyruvate, stearate, ascorbate, salicylate. When the compound of the present disclosure contains an acidic group, its pharmaceutically acceptable salts may also include: alkali metal salts, such as sodium or potassium salts; alkaline earth metal salts, such as calcium or magnesium salts; organic base salts, such as salts formed with ammonia, alkyl ammonia, hydroxyl alkyl ammonia, amino acids (lysine, arginine), N-methylglucamine, etc.

The "isomer" in the present disclosure means that the compound of formula (I) in the present disclosure may have asymmetric centers and racemates, racemic mixtures and individual diastereoisomers, all of these isomers, including stereoisomers, geometric isomers, and atropisomers are all included in the present disclosure. In the present disclosure, when the compound of formula (I) or the salt thereof exists in a stereoisomeric form (for example, it contains one or more asymmetric carbon atoms), the individual stereoisomers (enantiomers and diastereoisomers) and the mixture thereof are included within the scope of the present disclosure. The present disclosure also includes individual isomers of the compound of formula (I) or the salt thereof, and the mixture with isomers in which one or more chiral centers are inverted. The scope of the present disclosure includes: mixtures of stereoisomers, and purified enantiomers or enantiomerically/diastereomerically enriched mixtures. The present disclosure includes all stereoisomeric mixtures of all possible different combinations of enantiomers and diastereoisomers. The present disclosure includes all combinations and subsets of stereoisomers of all specific groups as defined above. The present disclosure also includes geometric isomers of the compound of formula (I) or the salt thereof, and the geometric isomers include cis-trans isomers.

Without violating common knowledge in the art, the above preferred conditions can be combined arbitrarily to obtain preferred examples of the present disclosure.

The reagents and raw materials used in the present disclosure are all commercially available.

BRIEF DESCRIPTION OF THE DRAWINGS

FIG. 1 is the tumor volume change curve of compound 2 (5 mg/kg, 10 mg/kg, 20 mg/Kg, p.o.) and positive control AZD6738 (20 mg/kg, p.o.) in subcutaneous transplantation tumor model of OCI-LY19 human B-cell lymphoma in mice.

DETAILED DESCRIPTION OF THE PREFERRED EMBODIMENT

The present disclosure is further illustrated below by means of examples, but the present disclosure is not thereby limited to the scope of the examples. For the experimental methods that do not specify specific conditions in the following examples, the experimental conditions are selected according to conventional methods and conditions, or according to the product instructions.

The meanings of the abbreviations used in the examples of the present disclosure are as follows:

The structures of all compounds of the present disclosure can be identified by nuclear magnetic resonance ($^1$H NMR) and/or mass spectrometry (MS).

$^1$H NMR chemical shifts (6) are reported in PPM ($10^{-6}$). NMR was performed on a Bruker AVANCE-400 spectrometer. Suitable solvents were deuterated chloroform ($CDCl_3$), deuterated methanol ($CD_3OD$), deuterated dimethylsulfoxide (DMSO-$d_6$), and tetramethylsilane was as internal standard (TMS).

Low resolution mass spectrum (MS) was determined by Ultimate 3000 HPLC-MSQ Plus MS mass spectrometer, using Kinetex 2.6u C18 100A (50×4.6 mm) LCMS-02-001, ESI source, gradient elution conditions: 95% solvent A and 5% solvent B (less than 1.5 minutes or more than 3 minutes), then 5% solvent A and 95% solvent B (1.5 minutes to 3 minutes), and the percentage is the volume percentage of a certain solvent to the total solvent volume.

Solvent A: 10 mM $NH_4HCO_3$(aq); solvent B: acetonitrile; the compounds and intermediates of the present disclosure can be purified using a conventional preparative silica gel plate or a flash separation machine, and the elution system can be EtOAc/PE system or DCM/MeOH system. Preparative HPLC can also be used for separation.

High-performance liquid chromatography (prep-HPLC) used SHIMADZU LC-20 HPLC, and the chromatographic column was: waters xbridge Pre C18, 10 m, 19×260 mm. Alkaline gradient elution, mobile phase B: 15-70% (v/v %), elution time: 20 minutes, mobile phase A: 10 mM $NH_4HCO_3$ (aq), mobile phase B: acetonitrile. Acidic gradient elution mobile phase B: 15%-55% (v/v %), elution time: 20 minutes, mobile phase A: 0.1% trifluoroacetic acid aqueous solution, mobile phase B: acetonitrile. Detection wavelength: 214 nm, and/or 254 nm, and/or 262 nm; flow rate: 10.0 mL/min.

The microwave reaction in the examples of the present disclosure used a Biotage® Initiator+Microwave System EU (356006) microwave reactor. Unless otherwise specified in the present disclosure, the reactions in all examples were carried out under a nitrogen atmosphere or an argon atmosphere.

The thin-layer silica gel plate (prep-TLC) was Yantai Huanghai HSGF254 or Qingdao GF254 silica gel plate.

The flash separation machine (flash column chromatography) (flash system/Cheetah™) used Agela Technologies MP200, and the supporting separation column was flash column Silica-CS (80 g), Cat No. CS140080-0.

The hydrogen atmosphere of the present disclosure can be achieved in the following ways: 1) The reaction system was connected to a hydrogen balloon with a volume of about 1 L; 2) under normal pressure, hydrogen was directly and continuously introduced into the reaction system; 3) sealing after hydrogen replacement with a sealed tube.

Unless otherwise specified in the present disclosure, the reactions in all examples were carried out under the protection of nitrogen or argon.

Example 1: Synthesis of (R)-3-methyl-4-(1-(methylsulfonyl)-6-(1H-pyrazol-3-yl)-1,6-dihydropyrazolo[3,4-b]pyrrolo[2,3-d]pyridin-4-yl)morpholine trifluoroacetate (Compound 1)

1

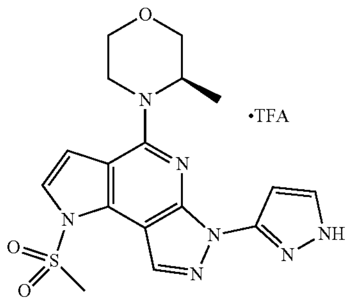

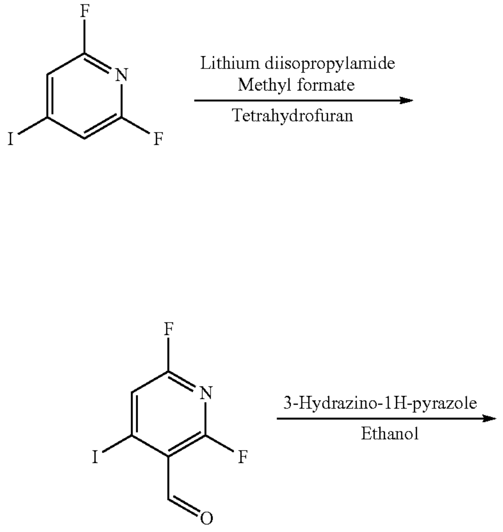

1-1

-continued

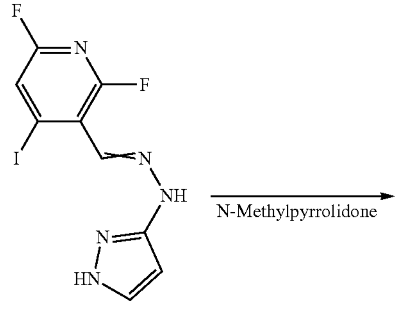

1.2

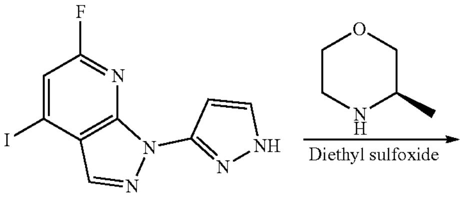

1.3

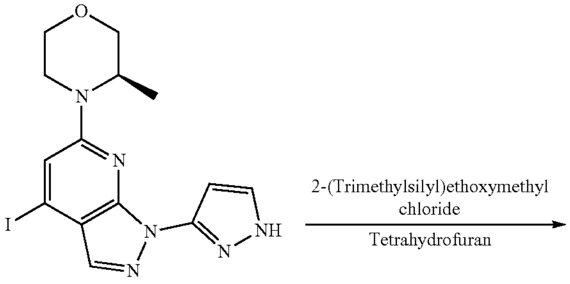

1.4

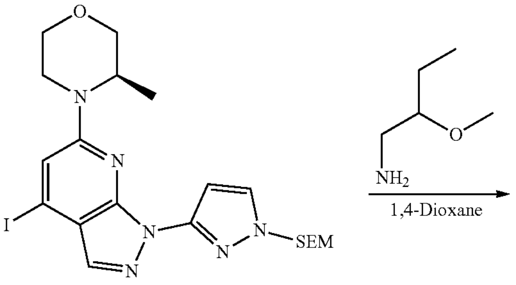

1.5

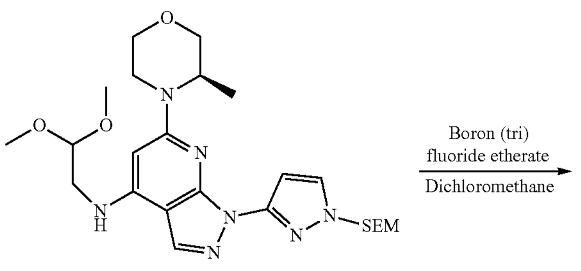

1.6

-continued

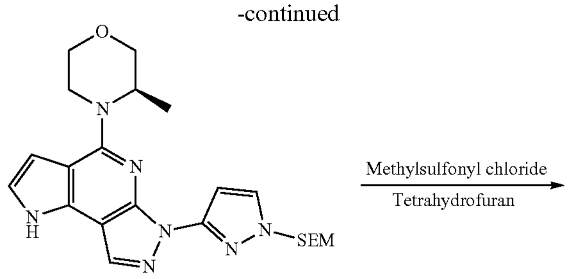

1.7

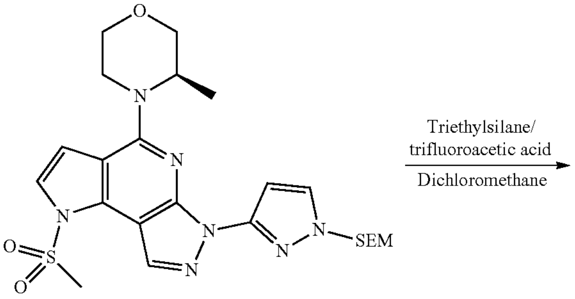

1.8

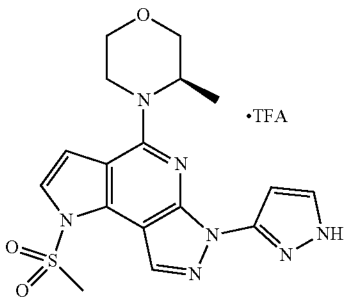

1

Step 1: At −70° C., a solution of lithium diisopropylamide in tetrahydrofuran (2.0 M, 2.2 mL, 4.46 mmol) was added dropwise to a solution of 2,6-difluoro-4-iodopyridine (1.0 g, 4.15 mmol) in tetrahydrofuran (10 mL), and the reaction system was stirred at this temperature for 30 minutes, then methyl formate (412 mg, 5.58 mmol) was added to the above reaction system and the stirring was continued for 1 hour. Water was added to quench the reaction, and the aqueous phase was extracted with ethyl acetate, then the organic phase was separated and concentrated under reduced pressure, and the residue was purified by flash column chromatography (ethyl acetate/petroleum ether=0-1/4) to obtain compound 1.1 (300 mg, yield: 27%) as a yellow solid.

Step 2: 3-Hydrazino-1H-pyrazole (91 mg, 0.93 mmol) was added to a solution of compound 1.1 (250 mg, 0.93 mmol) in ethanol (95%, 5 mL), and the reaction solution was stirred at room temperature for 2 hours. Under an ice-water bath, a saturated sodium bicarbonate aqueous solution was slowly added to the reaction system to quench the reaction, and the aqueous phase was extracted with ethyl acetate, then the organic phase was separated and concentrated under reduced pressure to obtain compound 1.2 (130 mg, yield: 40%) as a yellow solid.

Step 3: A solution of compound 1.2 (130 mg, 0.37 mmol) in N-methylpyrrolidone (2 mL) was reacted under microwave at 200° C. for 15 minutes. The reaction solution was directly poured into water and filtered. The filter cake was dried in vacuum to obtain compound 1.3 (150 mg, crude product) as a yellow solid. m/z: $[M+H]^+$ 330.0.

Step 4: (R)-3-Methylmorpholine (48 mg, 0.48 mmol) was added to a solution of compound 1.3 (80 mg, 0.24 mmol) in dimethyl sulfoxide (3 mL), and the reaction solution was stirred at 145° C. for 1 hour. Then the reaction solution was poured into water and filtered. The filter cake was dried to obtain compound 1.4 (70 mg, yield: 71%) as a yellow solid. m/z: $[M+H]^+$ 411.0.

Step 5: Under an ice bath, sodium hydride (60%, 14 mg, 0.35 mmol) was added to a solution of compound 1.4 (130 mg, 0.32 mmol) in tetrahydrofuran (3 mL), and the reaction solution was stirred at 0° C. for 30 minutes. 2-(Trimethylsilyl)ethoxymethyl chloride (73 mg, 0.44 mmol) was added to the above reaction solution and the reaction mixture was stirred at room temperature for 2 hours, then the reaction was quenched with water, and the aqueous phase was extracted with ethyl acetate. The organic phase was separated and concentrated under reduced pressure, and the residue was purified by flash column chromatography (ethyl acetate/petroleum ether=0-1/3) to obtain compound 1.5 (90 mg, yield: 52%) as a yellow oil. m/z: $[M+H]^+$ 541.3.

Step 6: Aminoacetaldehyde dimethyl acetal (26 mg, 0.25 mmol), tris(dibenzylideneacetone)dipalladium (9 mg, 0.01 mmol), (S)-(−)-2,2'-bis(diphenylphosphino)-1,1'-binaphthyl (6 mg, 0.01 mmol) and cesium carbonate (32.5 mg, 0.1 mmol) were added to a solution of compound 1.5 (26 mg, 0.05 mmol) in 1,4-dioxane (3 mL) in sequence. The reaction system was replaced with nitrogen and then stirred at 120° C. for 3 hours under nitrogen atmosphere. The reaction solution was directly concentrated under reduced pressure, and the residue was purified by flash column chromatography (ethyl acetate/petroleum ether=0-1/1) to obtain compound 1.6 (40 mg, yield: 78%) as a yellow oil. m/z: $[M+H]^+$ 518.2.

Step 7: Under an ice bath, boron (tri) fluoride etherate (62 mg, 0.44 mmol) was added to a solution of compound 1.6 (150 mg, 0.29 mmol) in dichloromethane (3 mL), and after the reaction solution was stirred at 0° C. for 30 minutes, the reaction was quenched with saturated sodium bicarbonate aqueous solution, and the aqueous phase was extracted with dichloromethane. The organic phases were combined and concentrated under reduced pressure. The residue was purified by flash column chromatography (ethyl acetate/petroleum ether=1/3) to obtain compound 1.7 (17 mg, yield: 13%) as a yellow oil. m/z: $[M+H]^+$ 454.2.

Step 8: Under an ice bath, sodium hydride (60%, 2.4 mg, 0.06 mmol) was added to a solution of compound 1.7 (17 mg, 0.04 mmol) in tetrahydrofuran (2 mL), and the reaction solution was stirred at 0° C. for 30 minutes, and methanesulfonyl chloride (6.8 mg, 0.06 mmol) was added to the above reaction solution and stirred at room temperature for 2 hours. The reaction was quenched with water, and the aqueous phase was extracted with ethyl acetate, and the organic phases were combined and concentrated under reduced pressure to obtain compound 1.8 (20 mg, crude product) as a yellow oil. m/z: $[M+H]^+$ 532.2.

Step 9: Under an ice bath, triethylsilane (33 mg, 0.29 mmol) and trifluoroacetic acid (0.5 mL) were added to a solution of compound 1.8 (20 mg, crude product) in dichloromethane (0.7 mL), and after the reaction solution was stirred at room temperature for 1 hour, the reaction solution was directly concentrated under reduced pressure. The residue was purified by prep-HPLC (acidic conditions) to obtain compound 1 (1.16 mg, two-step yield: 6%) as a gray solid. m/z: $[M+H]^+$ 402.1; $^1H$ NMR (400 MHz, $CDCl_3$): δ 8.32 (s, 1H), 7.86 (d, J=2.4 Hz, 1H), 7.56 (d, J=3.6 Hz, 1H), 7.12 (d, J=4.0 Hz, 1H), 6.86 (d, J=2.4 Hz, 1H), 4.56-4.54 (m, 1H), 3.98-3.95 (m, 2H), 3.81-3.53 (m, 7H), 1.26 (d, J=6.8 Hz, 3H).

Example 2: Synthesis of (R)-3-methyl-4-(1-(methylsulfonyl)-6-(1H-pyrazol-3-yl)-1,2,3,6-tetrahydropyrazolo[3,4-b]pyrrolo[2,3-d]pyridin-4-yl)morpholine trifluoroacetate (Compound 2)

2

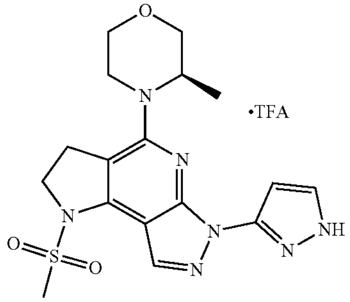

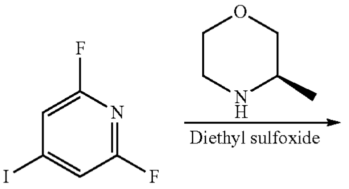

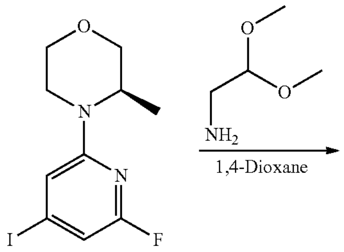

2.1

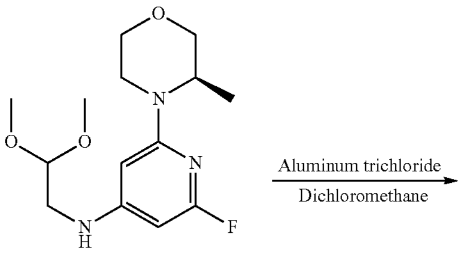

2.2

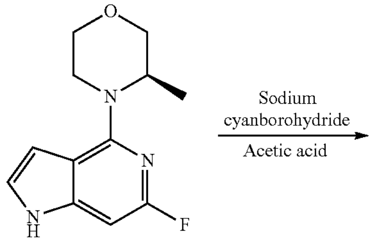

2.3

-continued

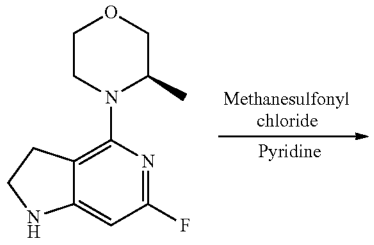

2.4

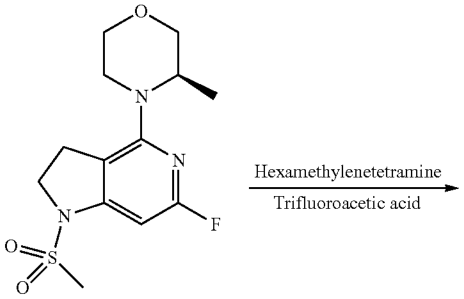

2.5

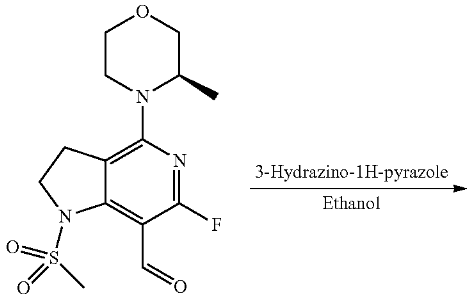

2.6

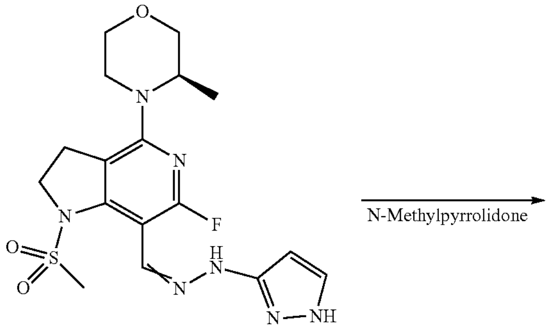

2.7

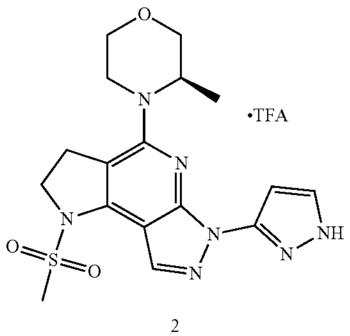

2

Step 1: A solution of 2,6-difluoro-4-iodopyridine (4.0 g, 16.6 mmol) and (R)-3-methylmorpholine (1.68 g, 16.6 mmol) in dimethyl sulfoxide (30 mL) was stirred at 100° C. for 5 hours. After cooling to room temperature, water was added to quench the reaction, and the aqueous phase was extracted with ethyl acetate. The organic phases were combined and washed with water and saturated brine in turn, then the organic phase was separated and dried over anhydrous sodium sulfate, filtered, and the filtrate was concentrated under reduced pressure, and the residue was purified by flash column chromatography (ethyl acetate/petroleum ether=0-3/2) to obtain compound 2.1 (4.4 g, yield: 82%) as a colorless oil. m/z: $[M+H]^+$ 323.0.

Step 2: A mixture of compound 2.1 (4.4 g, 13.6 mmol), aminoacetaldehyde dimethyl acetal (7.2 g, 68.0 mmol), tris(dibenzylideneacetone)dipalladium (576 mg, 0.68 mmol), (S)-(−)-2,2'-bis(diphenylphosphino)-1,1'-binaphthyl (396 mg, 0.63 mmol), cesium carbonate (5.9 g, 18.2 mmol) and 1,4-dioxane (30 mL) was purged with nitrogen for 3 times, and the reaction system was stirred at 100° C. for 5 hours under a nitrogen atmosphere. The reaction solution was cooled to room temperature, filtered, and the filtrate was concentrated under reduced pressure and the residue was purified by flash column chromatography (ethyl acetate/petroleum ether=0-1/1) to obtain compound 2.2 (3.0 g, yield: 74%) as a yellow oil. m/z: $[M+H]^+$ 300.2.

Step 3: At −10° C., a solution of compound 2.2 (3.0 g, 10.0 mmol) in dichloromethane (10 mL) was added to a suspension of aluminum trichloride (5.3 g, 40.0 mmol) in dichloromethane (40 mL), and the mixture was stirred at −10° C. for 20 minutes. Water was added to quench the reaction, and the aqueous phase was extracted with dichloromethane. The organic phases were combined and dried over anhydrous sodium sulfate, filtered, and the filtrate was concentrated under reduced pressure, and the residue was purified by flash column chromatography (ethyl acetate/petroleum ether=0-1/3) to obtain compound 2.3 (1.56 g, yield: 66%) as a yellow solid. m/z: $[M+H]^+$ 236.2.

Step 4: Sodium cyanoborohydride (1.49 g, 23.7 mmol) was added to a solution of compound 2.3 (2.8 g, 11.8 mmol) in acetic acid (25 mL), and the resulting mixture was stirred at room temperature for 9 hours, then the reaction solution was slowly poured into a saturated sodium bicarbonate aqueous solution, and the aqueous phase was extracted with ethyl acetate. The organic phases were combined and dried over anhydrous sodium sulfate, filtered, and the filtrate was concentrated under reduced pressure, and the residue was purified by flash column chromatography (ethyl acetate/petroleum ether=0-1/4) to obtain compound 2.4 (1.65 g, yield: 59%) as a yellow oil. m/z: $[M+H]^+$ 238.2.

Step 5: Under an ice bath, methanesulfonyl chloride (1.0 mL) was added to a solution of compound 2.4 (1.6 g, 6.72 mmol) in pyridine (5.0 mL), and the reaction solution was stirred at 0° C. for 1 hour. Water was added to quench the reaction, and the aqueous phase was extracted with ethyl acetate. The organic phases were combined and dried over anhydrous sodium sulfate, filtered, and the filtrate was concentrated under reduced pressure, and the residue was purified by flash column chromatography (ethyl acetate/petroleum ether=0-1/2) to obtain compound 2.5 (1.7 g, yield: 80%) as a yellow oil. m/z: $[M+H]^+$ 316.2.

Step 6: Hexamethylenetetramine (3.3 g, 23.5 mmol) was added to a solution of compound 2.5 (1.86 g, 5.9 mmol) in trifluoroacetic acid (20 mL), and the mixture was stirred at 70° C. for 1 hour. Water was added to quench the reaction, and the aqueous phase was extracted with ethyl acetate. The organic phases were combined and dried over anhydrous sodium sulfate, filtered, and the filtrate was concentrated under reduced pressure, and the residue was purified by flash column chromatography (ethyl acetate/petroleum ether=0-1/2) to obtain compound 2.6 (0.24 g, yield: 12%) as a yellow solid. m/z: $[M+H]^+$ 344.2.

Step 7: 3-Hydrazino-1H-pyrazole (0.34 g, 3.49 mmol) was added to a solution of compound 2.6 (0.24 g, 0.7 mmol) in ethanol (95%, 5 mL), and the reaction solution was stirred at room temperature for 20 minutes. Water was added to quench the reaction, and the aqueous phase was extracted with ethyl acetate. The combined organic phases were dried over anhydrous sodium sulfate, filtered, and the filtrate was concentrated under reduced pressure to obtain compound 2.7 (0.3 g, crude product) as a yellow solid. m/z: $[M+H]^+$ 424.2.

Step 8: A solution of compound 2.7 (0.3 g, crude product) in N-methylpyrrolidone (4 mL) was reacted under microwave at 180° C. for 20 minutes. Water was added to quench the reaction, and the aqueous phase was extracted with ethyl acetate. The combined organic phases were dried over anhydrous sodium sulfate, filtered, and the filtrate was concentrated under reduced pressure, and the residue was purified by prep-HPLC (acidic conditions) to obtain compound 2 (136 mg, two-step yield: 38%) as a yellow solid. m/z: $[M+H]^+$ 404.2; $^1$H NMR (400 MHz, DMSO-$d_6$): δ 8.24 (s, 1H), 7.84 (d, J=4.0 Hz, 1H), 6.83 (d, J=4.0 Hz, 1H), 4.20-4.02 (m, 3H), 3.94-3.88 (m, 1H), 3.76-3.66 (m, 3H), 3.41-3.28 (m, 2H), 3.24-3.10 (m, 5H), 1.18 (d, J=8.0 Hz, 3H).

Example 3: Synthesis of (R)—N,N-dimethyl-4-(3-methylmorpholino)-6-(1H-pyrazol-3-yl)pyrazolo[3,4-b]pyrrolo[2,3-d]pyridine-1(6H)-sulfonamide trifluoroacetate (Compound 3)

3

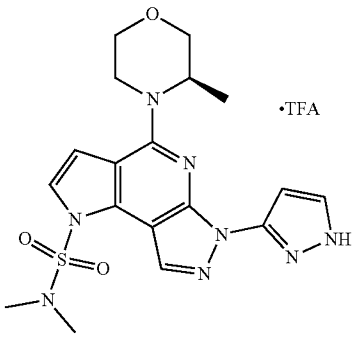

Using the synthesis method of compound 1, methanesulfonyl chloride in step 8 was replaced by dimethylaminosulfonyl chloride to obtain compound 3 as an off-white solid. m/z: $[M+H]^+$ 431.2; $^1$H NMR (400 MHz, $CDCl_3$): δ 8.55 (s, 1H), 7.81 (s, 1H), 7.60-7.56 (m, 1H), 7.04-7.02 (m, 2H), 4.65 (m, 1H), 4.05-4.03 (m, 2H), 3.95-3.91 (m, 1H), 3.81-3.78 (m, 4H), 2.89 (s, 6H), 1.41 (d, J=6.4 Hz, 3H).

Example 4: Synthesis of (R)—N,N-dimethyl-4-(3-methylmorpholino)-6-(1H-pyrazol-3-yl)-2,3-dihydropyrazolo[3,4-b]pyrrolo[2,3-d]pyridine-1(6H)-sulfonamide trifluoroacetate (Compound 4)

4

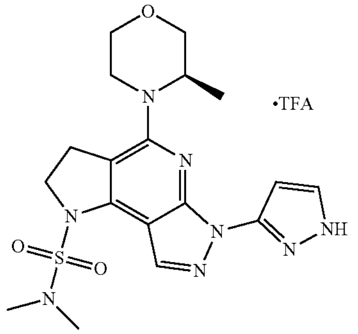

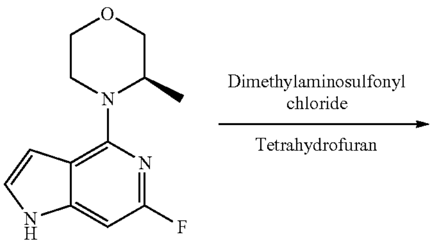

2.3

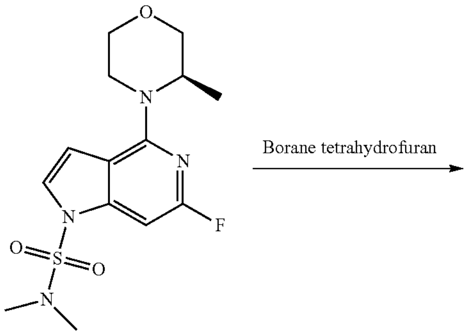

4.1

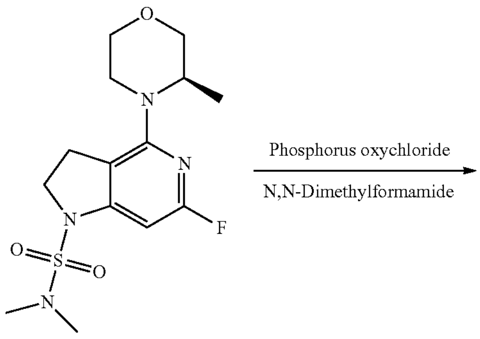

4.2

-continued

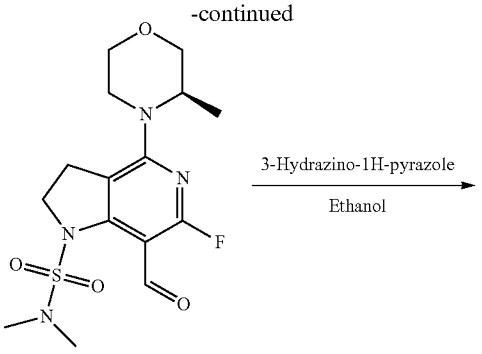

4.3

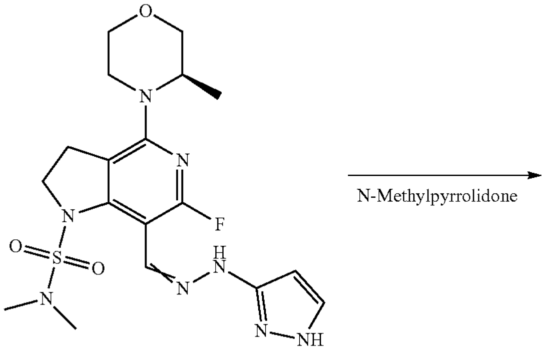

4.4

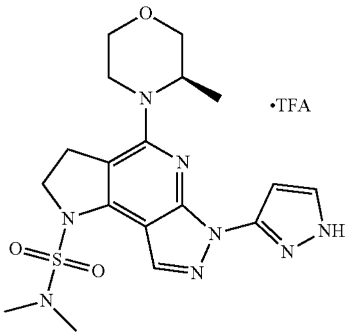

4

Step 1: Under an ice bath, sodium hydride (136 mg, 3.4 mmol) was added to a solution of compound 2.3 (0.4 g, 1.7 mmol) in tetrahydrofuran (2 mL), and the reaction solution was stirred at 0° C. for 1 hour. Then dimethylaminosulfonyl chloride (0.4 g, 3.4 mmol) was added to the above reaction solution, and the mixture was stirred at room temperature for 2 hours. Saturated ammonium chloride aqueous solution was added to quench the reaction, and the aqueous phase was extracted with ethyl acetate. The organic phases were combined and dried over anhydrous sodium sulfate, filtered, and the filtrate was concentrated under reduced pressure, and the residue was purified by flash column chromatography (ethyl acetate/petroleum ether=0-1/1) to obtain compound 4.1 (0.45 g, yield: 77%) as a yellow oil. m/z: $[M+H]^+$ 343.2.

Step 2: Compound 4.1 (0.45 g, 1.3 mmol) was added to borane tetrahydrofuran complex (5 mL, 5.0 mmol), and the mixture was stirred at 80° C. for 1 hour. After cooling to room temperature, methanol (5 mL) was added, and the reaction system was stirred at reflux for 48 hours. The reaction solution was concentrated under reduced pressure, and the residue was purified by flash column chromatography (ethyl acetate/petroleum ether=0-2/1) to obtain compound 4.2 (0.1 g, yield: 22%) as a yellow solid. m/z: $[M+H]^+$ 345.2.

Step 3: Under an ice bath, phosphorus oxychloride (0.5 mL) was slowly added dropwise to N,N-dimethylformamide (2.0 mL), and the reaction solution was stirred for 30 minutes, then compound 4.2 (80 mg, 0.23 mmol) was added to the above reaction solution, and the reaction system was stirred at 80° C. for 2 hours. Water was added to quench the reaction, and the aqueous phase was extracted with ethyl acetate. The combined organic phases were dried over anhydrous sodium sulfate, filtered, and the filtrate was concentrated under reduced pressure to obtain compound 4.3 (39 mg, yield: 44%) as a yellow solid. m/z: $[M+H]^+$ 373.2.

Step 4: 3-Hydrazino-1H-pyrazole (50 mg, 0.51 mmol) was added to a solution of compound 4.3 (38 mg, 0.1 mmol) in ethanol (95%, 3 mL), and the reaction solution was stirred at room temperature for 20 minutes. Water was added to quench the reaction, and the aqueous phase was extracted with ethyl acetate. The combined organic phases were dried over anhydrous sodium sulfate, filtered, and the filtrate was concentrated under reduced pressure to obtain compound 4.4 (38 mg, crude product) as a yellow solid. m/z: $[M+H]^+$ 453.2.

Step 5: A solution of compound 4.4 (38 mg, crude product) in N-methylpyrrolidone (2 mL) was reacted under microwave at 180° C. for 20 minutes. Water was added to quench the reaction, and the aqueous phase was extracted with ethyl acetate. The combined organic phases were dried over anhydrous sodium sulfate, filtered, and the filtrate was concentrated under reduced pressure, and the residue was purified by prep-HPLC (acidic conditions) to obtain compound 4 (5.2 mg, two-step yield: 9%) as a pale yellow solid. m/z: $[M+H]^+$ 433.2; $^1H$ NMR (400 MHz, DMSO-$d_6$): δ 8.39 (s, 1H), 7.69 (s, 1H), 6.89 (s, 1H), 4.25-3.97 (m, 4H), 3.75-3.55 (m, 5H), 3.32-3.12 (m, 2H), 2.96 (s, 6H), 1.26 (d, J=8.0 Hz, 3H).

Example 5: Synthesis of (R)-4-(3-methylmorpholine)-6-(1H-pyrazol-3-yl)-2,3-dihydropyrazolo[3,4-b]pyrrolo[2,3-d]pyridine-1(6H)-sulfonamide (Compound 5)

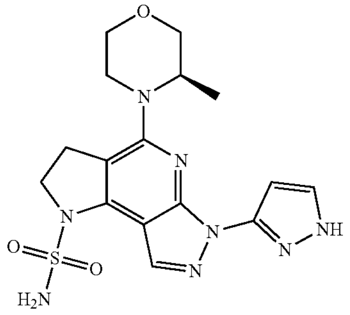

-continued

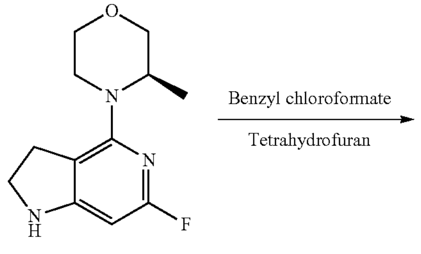

2.4

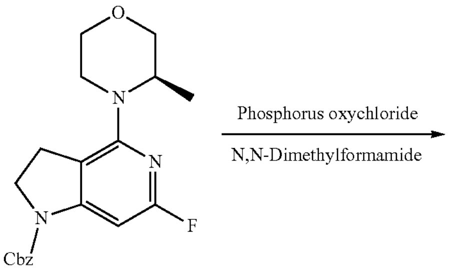

5.1

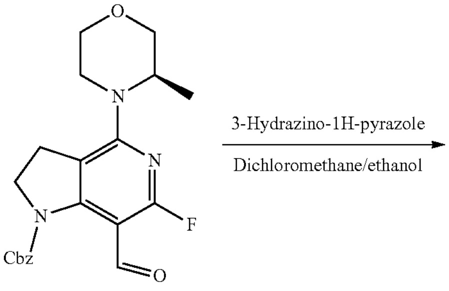

5.2

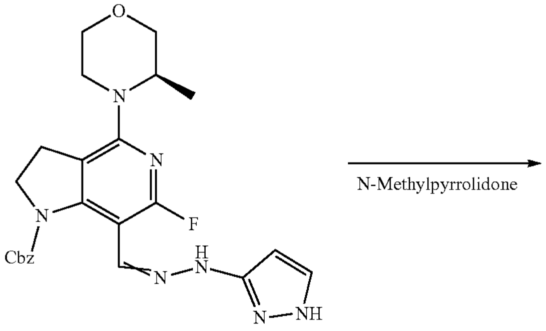

5.3

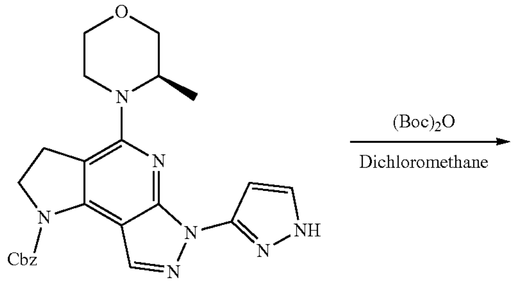

5.4

-continued

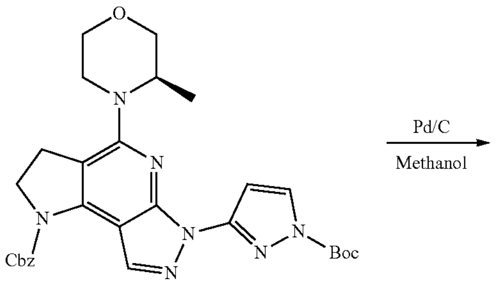

5.5

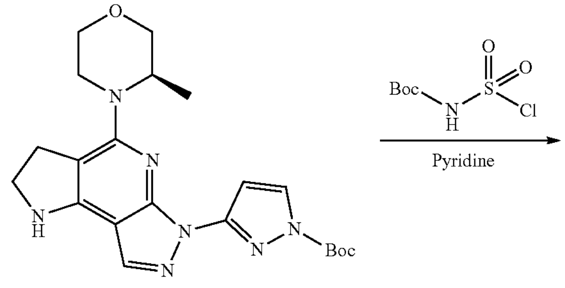

5.6

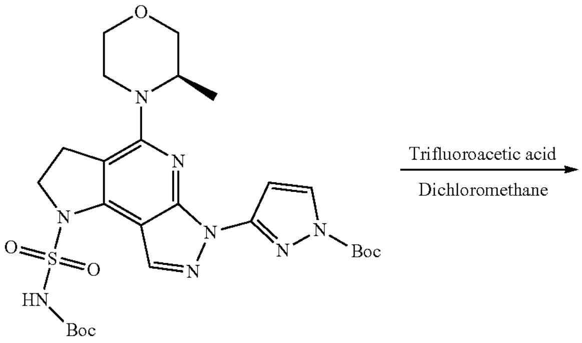

5.7

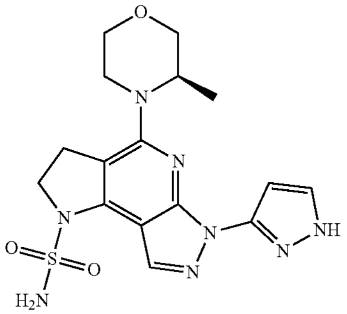

5

Step: 1: Under an ice bath, sodium hydride (80 mg, 2.0 mmol) was added to a solution of compound 2.4 (238 mg, 1.0 mmol) in tetrahydrofuran (10 mL), and the reaction system was stirred at this temperature for 0.5 hours, then benzyl chloroformate (340 mg, 2.0 mmol) was added thereto. The reaction solution was stirred overnight at room temperature, then water was added to quench the reaction, and the aqueous phase was extracted with ethyl acetate. The organic phases were combined and dried over anhydrous sodium sulfate, filtered, and the filtrate was concentrated under reduced pressure, and the residue was purified by flash column chromatography (ethyl acetate/petroleum ether=0-

1/2) to obtain compound 5.1 (250 mg, yield: 67%) as a yellow solid. m/z: $[M+H]^+$ 372.2.

Step 2: Phosphorus oxychloride (0.5 mL) was slowly added dropwise to a solution of compound 5.1 (150 mg, 0.4 mmol) in N,N-dimethylformamide (2 mL), and the reaction solution was stirred overnight at 80° C. Water was added to quench the reaction, and the aqueous phase was extracted with ethyl acetate. The organic phases were combined and dried over anhydrous sodium sulfate, filtered, and the filtrate was concentrated under reduced pressure, and the residue was purified by flash column chromatography (ethyl acetate/petroleum ether=0-1/2) to obtain compound 5.2 (100 mg, yield: 63%) as a yellow oil. m/z: $[M+H]^+$ 400.2.

Step 3: 3-Hydrazino-1H-pyrazole (75 mg, 0.75 mmol) was added to a mixed solution of compound 5.2 (100 mg, 0.25 mmol) in dichloromethane (1 mL) and ethanol (1 mL), and the reaction solution was stirred at room temperature for 1 hour. Saturated sodium bicarbonate aqueous solution was added to quench the reaction, and the aqueous phase was extracted with ethyl acetate. The organic phases were combined and dried over anhydrous sodium sulfate, filtered, and the filtrate was concentrated under reduced pressure to obtain compound 5.3 (167 mg, crude product) as a yellow solid. m/z: $[M+H]^+$ 480.2.

Step 4: A solution of compound 5.3 (167 mg, crude product) in N-methylpyrrolidone (3 mL) was reacted under microwave irradiation at 180° C. for 2 hours. Water was added to quench the reaction, and the aqueous phase was extracted with ethyl acetate. The organic phases were combined and dried over anhydrous sodium sulfate, filtered, and the filtrate was concentrated under reduced pressure, and the residue was purified by flash column chromatography (methanol/dichloromethane=0-3/100) to obtain compound 5.4 (60 mg, two-step yield: 52%) as a yellow oil. m/z: $[M+H]^+$ 460.2.

Step 5: N,N-Diisopropylethylamine (52 mg, 0.4 mmol), $(Boc)_2O$ (44 mg, 0.2 mmol) and 4-dimethylaminopyridine (3 mg) were added to a solution of compound 5.4 (60 mg, 0.13 mmol) in dichloromethane (10 mL), and the reaction solution was stirred at room temperature for 5 hours then directly concentrated under reduced pressure. The residue was purified by flash column chromatography (ethyl acetate/petroleum ether=0-1/2) to obtain compound 5.5 (40 mg, yield: 55%) as a yellow solid. m/z: $[M+H]^+$ 560.2.

Step 6: Pd/C (10%, 40 mg) was added to a solution of compound 5.5 (40 mg, 0.07 mmol) in methanol (4 mL), and the reaction system was purged with hydrogen then stirred at room temperature under a hydrogen atmosphere for 2 hours. The reaction solution was filtered, and the filtrate was concentrated under reduced pressure to obtain compound 5.6 (30 mg, yield: 100%) as a yellow solid. m/z: $[M+H]^+$ 426.2.

Step 7: N-(tert-Butoxycarbonyl)sulfonyl chloride (27 mg, 0.12 mmol) was added to a solution of compound 5.6 (60 mg, 0.14 mmol) in pyridine (10 mL), and the reaction solution was stirred at room temperature for 2 hours. The reaction was quenched by adding saturated sodium bicarbonate aqueous solution, and the aqueous phase was extracted with ethyl acetate.

The organic phases were combined and dried over anhydrous sodium sulfate, filtered, and the filtrate was concentrated under reduced pressure to obtain compound 5.7 (20 mg, yield: 24%) as a yellow oil. m/z: $[M+H]^+$ 605.2.

Step 8: Trifluoroacetic acid (0.5 mL) was added to a solution of compound 5.7 (20 mg, 0.03 mmol) in dichloromethane (0.5 mL). The reaction solution was stirred at room temperature for 3 hours and concentrated under reduced pressure. The residue was purified by prep-HPLC (alkaline conditions) to obtain compound 5 (2 mg, yield: 16%) as a gray solid. m/z: $[M+H]^+$ 405.2; $^1H$ NMR (400 MHz, DMSO-$d_6$): δ 13.18-12.44 (br. s, 1H), 8.28 (s, 1H), 7.82 (d, J=2.4 Hz, 1H), 6.82 (d, J=2.4 Hz, 1H), 4.10-3.85 (m, 5H), 3.74-3.70 (m, 1H), 3.63-3.54 (m, 4H), 3.22-3.07 (m, 3H), 1.15 (d, J=6.4 Hz, 3H).

Example 6: Synthesis of (R)-4-(6-(1H-pyrazol-3-yl)-1-((trifluoromethyl)sulfonyl)-1,2,3,6-tetrahydropyrazolo[3,4-b]pyrrolo[2,3-d]pyridin-4-yl)-3-methylmorpholine trifluoroacetate (Compound 6)

6

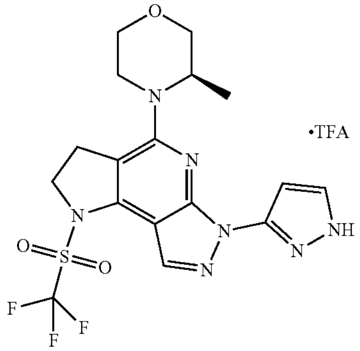

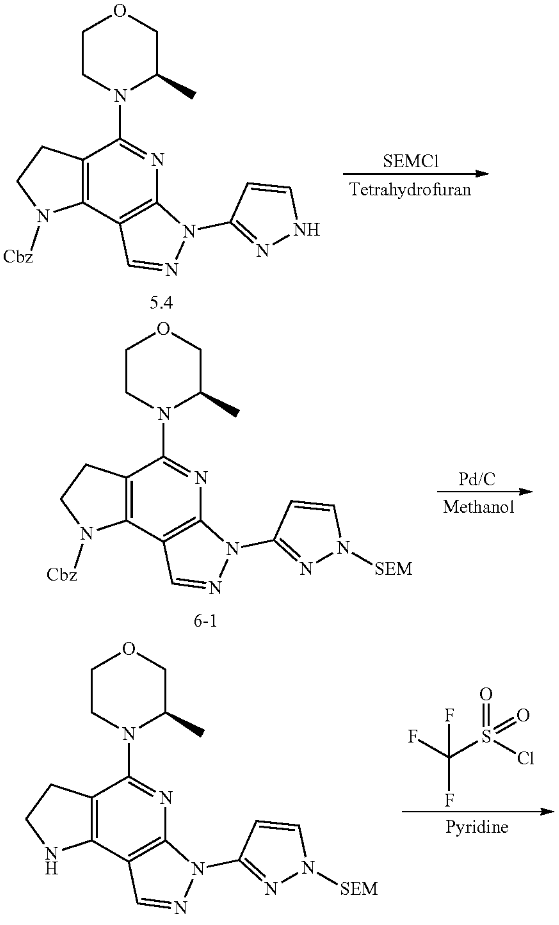

5.4

6-1

6-2

-continued

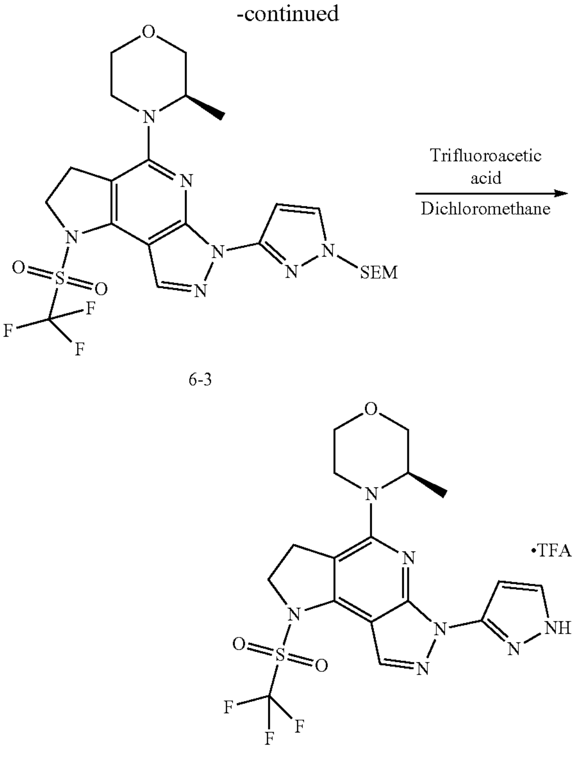

6-3

6

Step 1: Under an ice bath, sodium hydride (94 mg, 2.35 mmol) was added to a solution of compound 5.4 (0.54 g, 1.17 mmol) in tetrahydrofuran (6 mL), and the reaction mixture was stirred at 0° C. for 0.5 hours, and 2-(trimethylsilyl)ethoxymethyl chloride (0.39 g, 2.35 mmol) was added to the above reaction solution, and the resulting mixture was stirred at room temperature for 0.5 hours. Water was added to quench the reaction, and the aqueous phase was extracted with ethyl acetate. The organic phases were combined and dried over anhydrous sodium sulfate, filtered, and the filtrate was concentrated under reduced pressure, and the residue was purified by flash column chromatography (ethyl acetate/petroleum ether=0-1/1) to obtain compound 6.1 (360 mg, yield: 52%) as a yellow solid. m/z: $[M+H]^+$ 590.2.

Step 2: Pd/C (10%, 120 mg) was added to a solution of compound 6.1 (360 mg, 0.61 mmol) in methanol (5 mL), and the reaction system was purged with hydrogen and stirred at room temperature for 2 hours under a hydrogen atmosphere. The reaction solution was filtered, and the filtrate was concentrated under reduced pressure to obtain compound 6.2 (280 mg, yield: 100%) as a yellow oil. m/z: $[M+H]^+$ 456.2.

Step 3: Trifluoromethanesulfonyl chloride (25.2 mg, 0.15 mmol) was added to a solution of compound 6.2 (34 mg, 0.08 mmol) in pyridine (2 mL), and the reaction solution was stirred at room temperature for 1 hour. Water was added to quench the reaction, and the aqueous phase was extracted with ethyl acetate. The organic phases were combined and dried over anhydrous sodium sulfate, filtered, and the filtrate was concentrated under reduced pressure to obtain compound 6.3 (55 mg, crude product) as a yellow oil. m/z: $[M+H]^+$ 588.2.

Step 4: Triethylsilane (73.1 mg, 0.63 mmol) was added to a mixed solution of compound 6.3 (55 mg, crude product) in trifluoroacetic acid (1 mL) and dichloromethane (1 mL), and the resulting reaction solution was stirred at room temperature for 1 hour, then concentrated under reduced pressure, and the residue was purified by prep-HPLC (acidic conditions) to obtain compound 6 (12 mg, two-step yield: 26%) as a light yellow solid. m/z: $[M+H]^+$ 458.2; $^1H$ NMR (400 MHz, DMSO-$d_6$): δ 12.97 (s, 1H), 8.12 (s, 1H), 7.90 (s, 1H), 6.85 (s, 1H), 4.50-4.32 (m, 2H), 4.24-4.18 (m, 1H), 4.02-3.86 (m, 1H), 3.76-3.52 (m, 7H), 1.34 (d, J=8.0 Hz, 3H).

Example 7: Synthesis of (R)-4-(3-methylmorpholinyl)-1-(methylsulfonyl)-6-(1H-pyrazol-3-yl)-1,2,3,6-tetrahydropyrazolo[3,4-b]pyrrolo[2,3-d]pyridine-8-carbonitrile (Compound 7)

7

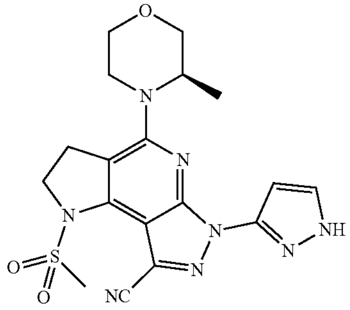

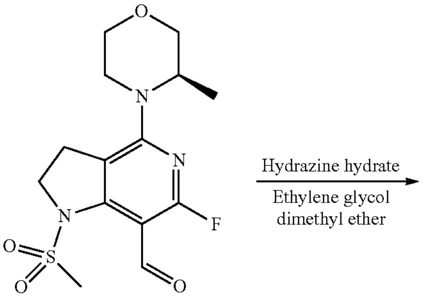

2.6

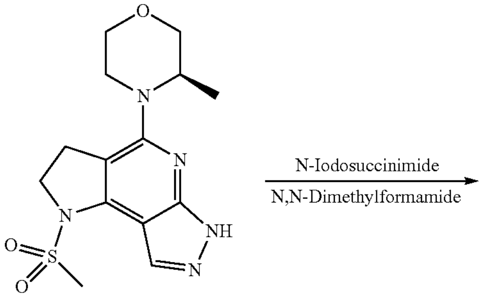

7.1

-continued

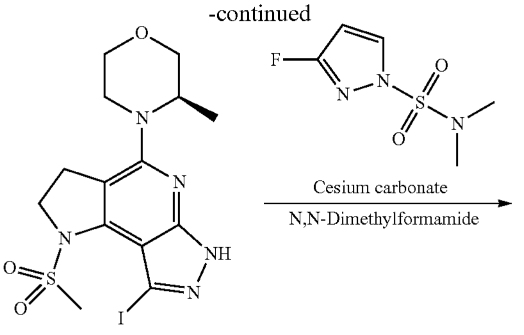

7.2

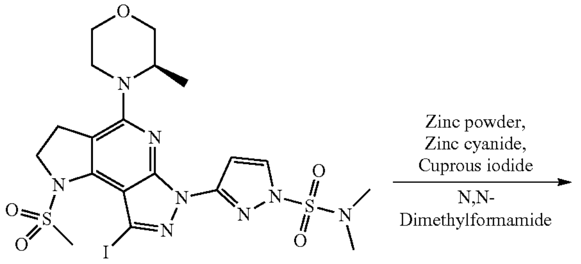

7.3

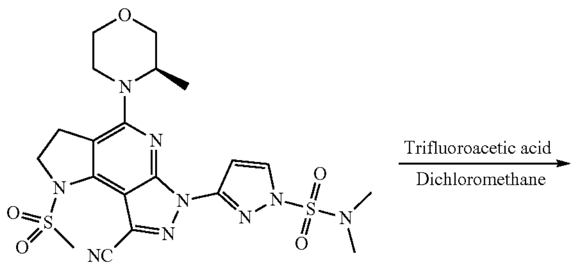

7.4

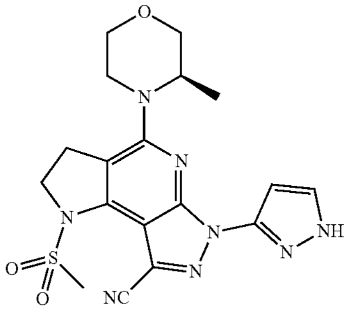

7

Step 1: A mixture of compound 2.6 (0.51 g, 1.48 mmol), hydrazine hydrate (3 mL) and ethylene glycol dimethyl ether (5 mL) was stirred at room temperature for 5 hours, and then the reaction solution was directly concentrated under reduced pressure. The residue was purified by flash column chromatography (ethyl acetate/petroleum ether=0-3/2) to obtain compound 7.1 (270 mg, yield: 54%) as a yellow solid. m/z: $[M+H]^+$ 338.2.

Step 2: Under a nitrogen atmosphere, N-iodosuccinimide (0.27 g, 1.2 mmol) was added to a solution of compound 7.1 (0.27 g, 0.8 mmol) in N,N-dimethylformamide (2.5 mL). The reaction solution was stirred at 40° C. for 16 hours. Water was added to quench the reaction, and the aqueous phase was extracted with ethyl acetate. The organic phases were combined and washed with water, then the organic phase was separated and dried over anhydrous sodium sulfate, filtered, and the filtrate was concentrated under reduced pressure. The residue was purified by flash column chromatography (ethyl acetate/petroleum ether=0-2/1) to obtain compound 7.2 (120 mg, yield: 32%) as a yellow solid. m/z: $[M+H]^+$ 464.2.

Step 3: A mixture of compound 7.2 (100 mg, 0.22 mmol), 3-fluoro-N,N-dimethyl-1H-pyrazole-1-sulfonamide (84 mg, 0.44 mmol), cesium carbonate (215 mg, 0.66 mmol) and N,N-dimethylformamide (5 mL) was stirred at 100° C. for 10 hours, then water was added to quench the reaction. The aqueous phase was extracted with ethyl acetate, and the organic phases were combined and washed with water, then the organic phase was separated and dried over sodium sulfate, filtered, and the filtrate was concentrated under reduced pressure. The residue was purified by flash column chromatography (ethyl acetate/petroleum ether=0-3/2) to obtain compound 7.3 (30 mg, yield: 21%) as a yellow solid. m/z: $[M+H]^+$ 637.2.

Step 4: Under a nitrogen atmosphere, a mixture of compound 7.3 (30 mg, 47 μmol), zinc powder (1.6 mg, 24 μmol), zinc cyanide (16.5 mg, 0.14 mmol), cuprous iodide (9 mg, 47 μmol) and a solution of [1,1'-bis(diphenylphosphino)ferrocene]dichloropalladium(II) (7 mg, 0.01 mmol) in N,N-dimethylformamide (2.5 mL) was purged with nitrogen, then reacted under microwave at 120° C. for 5 hours. The reaction solution was cooled to room temperature, then water was added to quench the reaction, and the aqueous phase was extracted with ethyl acetate.

The organic phases were combined and washed with water, then the organic phase was separated and dried over anhydrous sodium sulfate, filtered, and the filtrate was concentrated under reduced pressure, and the residue was purified by flash column chromatography (ethyl acetate/petroleum ether=0-3/2) to obtain compound 7.4 (15 mg, yield: 60%) as a yellow oil. m/z: $[M+H]^+$ 536.2.

Step 5: A mixed solution of compound 7.4 (15 mg, 28 μmol) in trifluoroacetic acid (0.2 mL) and dichloromethane (1 mL) was stirred at room temperature for 1 hour, then the reaction solution was concentrated under reduced pressure, and the residue was purified by prep-HPLC (alkaline conditions) to obtain compound 7 (1.55 mg, yield: 13%) as a pale yellow solid. m/z: $[M+H]^+$ 429.2.

Example 8: Synthesis of (R)-3-methyl-4-(1-(methylsulfonyl)-6-(1H-pyrazol-3-yl)-1H-pyrrolo[3,2-c][1,7]naphthyridin-4-yl)morpholine (Compound 8)

8

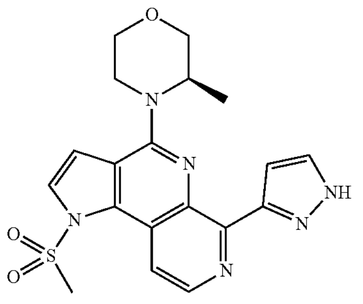

-continued

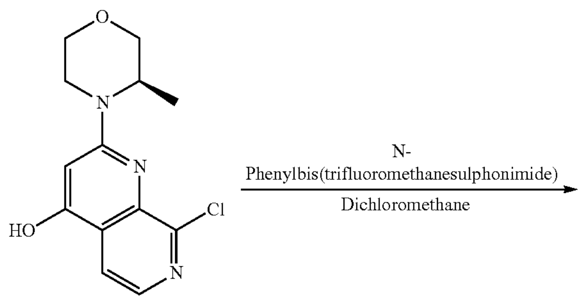

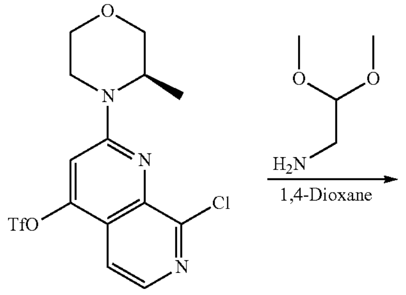

8.1

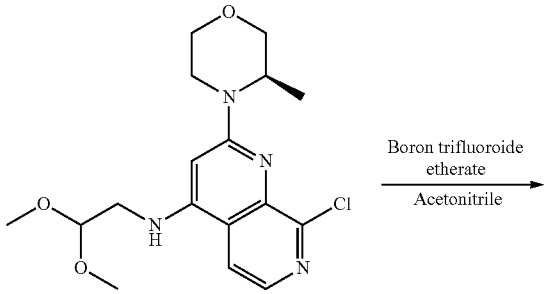

8-2

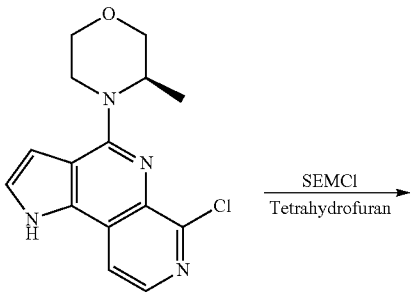

8.3

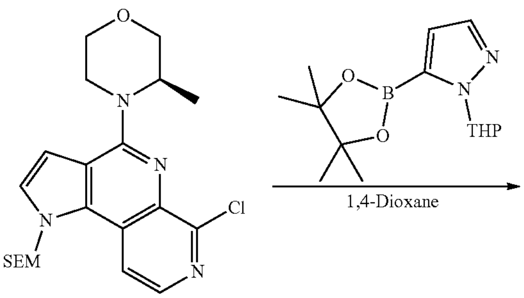

8-4

-continued

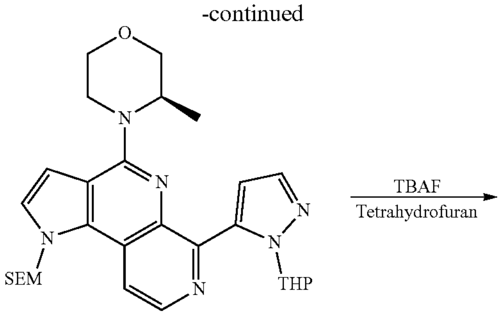

8.5

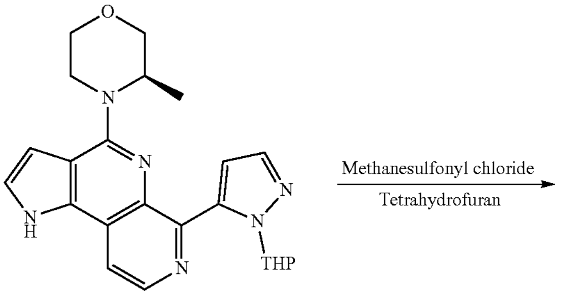

8.6

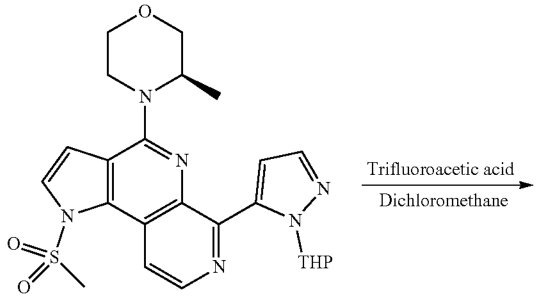

8.7

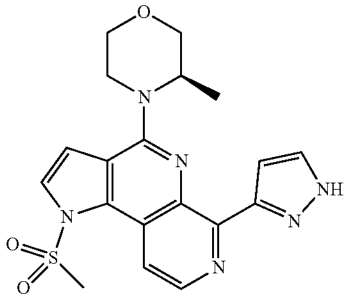

8

Step 1: N,N-Diisopropylethylamine (5.5 µg, 42.8 mmol) and N-phenylbis(trifluoromethanesulphonimide) (9.2 g, 25.7 mmol) were added to a solution of (R)-8-chloro-2-(3-methylmorpholinyl)-1,7-naphthyridin-4-ol (6 g, 21.4 mmol) in dichloromethane (200 mL). The reaction solution was stirred overnight at room temperature and concentrated under reduced pressure, and the residue was purified by flash column chromatography (ethyl acetate/petroleum ether=0-2/3) to obtain compound 8.1 (8 g, yield: 91%) as a yellow solid. m/z: $[M+H]^+$ 412.2.

Step 2: 2,2-Dimethoxyethylamine (1.2 µg, 10.3 mmol), tris(dibenzylideneacetone)dipalladium (394 mg, 0.43 mmol), Xantphos (249 mg, 0.43 mmol) and potassium phosphate (3.6 g, 17.2 mmol) were added to a solution of compound 8.1 (3.6 g, 8.6 mmol) in 1,4-dioxane (100 mL), and the reaction system was purged with nitrogen for 3 times, and then stirred under a nitrogen atmosphere at 110° C. for 2 hours. After cooling to room temperature, the reaction mixture was directly concentrated under reduced pressure, and the residue was purified by flash column chromatography (ethyl acetate/petroleum ether=0-2/3) to obtain compound 8.2 (2.2 g, yield: 70%) as a yellow solid. m/z: $[M+H]^+$ 367.2.

Step 3: Boron trifluoride etherate (2 g, 14.2 mmol) was added to a solution of compound 8.2 (2.1 g, 5.7 mmol) in acetonitrile (30 mL). The reaction solution was stirred at room temperature overnight. The reaction was quenched with saturated sodium bicarbonate aqueous solution, and the aqueous phase was extracted with dichloromethane. The organic phases were combined and dried over anhydrous sodium sulfate, filtered, then the filtrate was concentrated under reduced pressure, and the residue was purified by flash column chromatography (ethyl acetate/petroleum ether=0-7/10) to obtain compound 8.3 (1 g, yield: 58%) as a yellow solid. m/z: $[M+H]^+$ 303.2.

Step 4: Under an ice bath, sodium hydride (36 mg, 0.9 mmol) was added to a solution of compound 8.3 (100 mg, 0.3 mmol) in tetrahydrofuran (3 mL), and the reaction system was stirred at 0° C. for 0.5 hours. Then 2-(trimethylsilyl)ethoxymethyl chloride (140 mg, 0.9 mmol) was added thereto, the reaction solution was stirred overnight at room temperature and then quenched with saturated sodium bicarbonate aqueous solution. The aqueous phase was extracted with ethyl acetate, and the organic phases were combined and dried over anhydrous sodium sulfate, filtered, then the filtrate was concentrated under reduced pressure, and the residue was purified by flash column chromatography (ethyl acetate/petroleum ether=0-2/3) to obtain compound 8.4 (120 mg, yield: 92%) as a yellow solid. m/z: $[M+H]^+$ 433.2.

Step 5: 1-(2-Tetrahydropyranyl)-1H-pyrazole-5-boronic acid pinacol ester (68 mg, 0.34 mmol), [1,1'-bis(diphenylphosphino)ferrocene]dichloropalladium(II) (16 mg, 0.02 mmol) and cesium carbonate (79 mg, 0.24 mmol) were sequentially added to a mixed solution of compound 8.4 (100 mg, 0.24 mmol) in 1,4-dioxane (4 mL) and water (1 mL), after the reaction system was purged with nitrogen, the reaction solution was reacted under microwave at 120° C. for 0.5 hours. The reaction system was cooled down to room temperature and concentrated under reduced pressure, and the residue was purified by flash column chromatography (methanol/dichloromethane=0-3/100) to obtain compound 8.5 (60 mg, yield: 46%) as a yellow oil. m/z: $[M+H]^+$ 549.2.

Step 6: A solution of tetrabutylammonium fluoride in tetrahydrofuran (1 M, 0.8 mL) was added to a solution of compound 8.5 (60 mg, 0.1 mmol) in tetrahydrofuran (2 mL), and the reaction solution was stirred at 50° C. for 6 hours. Water was added to quench the reaction, then the aqueous phase was extracted with dichloromethane, and the organic phases were combined and dried over anhydrous sodium sulfate, filtered, and the filtrate was concentrated under reduced pressure, and the residue was purified by flash column chromatography (dichloromethane/methanol=0-3/100) to obtain compound 8.6 (40 mg, yield: 95%) as a yellow oil. m/z: $[M+H]^+$ 419.2.

Step 7: Under an ice bath, sodium hydride (12 mg, 0.3 mmol) was added to a solution of compound 8.6 (40 mg, 0.1 mmol) in tetrahydrofuran (6 mL), and the reaction system was stirred at 0° C. for 0.5 hours. Then methanesulfonyl chloride (34 mg, 0.3 mmol) was added thereto, and the reaction solution was stirred at room temperature for 3 hours, and saturated sodium bicarbonate aqueous solution was added to quench the reaction. The aqueous phase was extracted with dichloromethane, and the organic phases were combined and dried over anhydrous sodium sulfate, filtered, and the filtrate was concentrated under reduced pressure to obtain compound 8.7 (30 mg, yield: 60%) as a yellow oil. m/z: $[M+H]^+$ 497.2.

Step 8: Trifluoroacetic acid (1 ml) was added to a solution of compound 8.7 (30 mg, 0.06 mmol) in dichloromethane (2 mL). After the reaction mixture was stirred at room temperature for 1 hour, the reaction was quenched with saturated sodium bicarbonate aqueous solution. The aqueous phase was extracted with dichloromethane, and the organic phases were combined and dried over anhydrous sodium sulfate, filtered, then the filtrate was concentrated under reduced pressure, and the residue was purified by prep-HPLC (alkaline conditions) to obtain compound 8 (17 mg, yield: 68%) as a yellow solid. m/z: $[M+H]^+$ 413.2; $^1H$ NMR (400 MHz, DMSO-$d_6$): δ 13.41 (s, 1H), 8.56-8.51 (m, 2H), 7.96 (d, J=3.6 Hz, 1H), 7.63 (s, 1H), 7.41 (s, 1H), 7.21 (d, J=3.6 Hz, 1H), 4.63-4.55 (m, 1H), 4.06-4.03 (m, 1H), 3.95-3.86 (m, 2H), 3.81 (s, 3H), 3.76-3.62 (m, 3H), 1.27 (d, J=6.8 Hz, 3H).

Example 9: Synthesis of (R)-3-methyl-4-(1-(methylsulfonyl)-7-(1H-pyrazol-3-yl)-2,3,4,7-tetrahydro-1H-pyrazolo[3,4-h][1,6]naphthyridin-5-yl)morpholine trifluoroacetate (Compound 9)

9

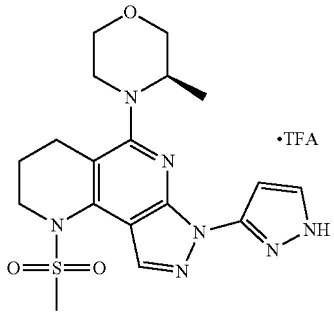

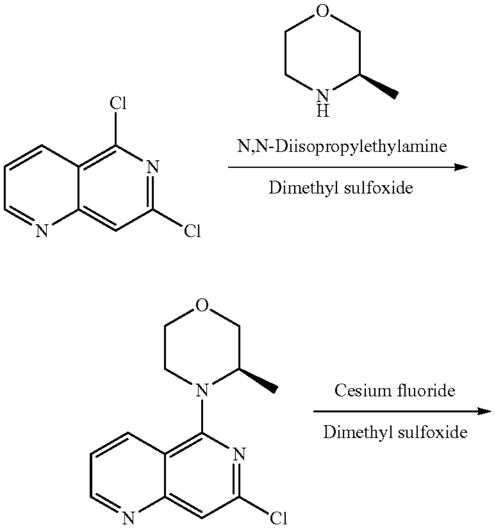

9.1

-continued

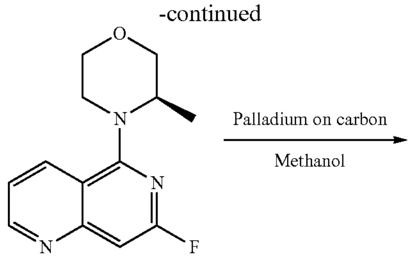

9.2

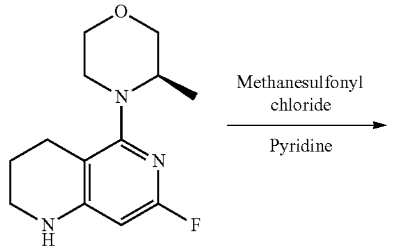

9.3

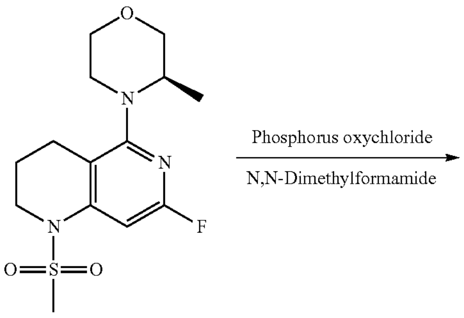

9.4

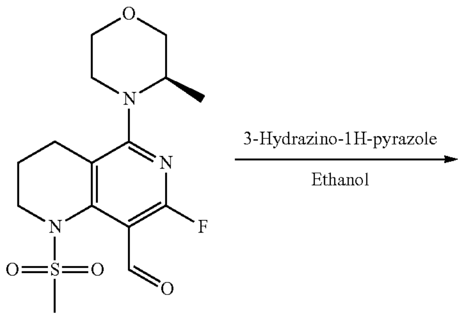

9.5

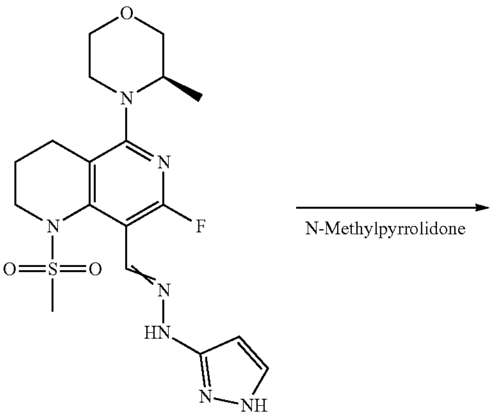

9.6

-continued

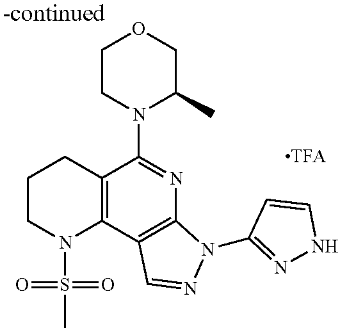

9

Step 1: N,N-Diisopropylethylamine (8.57 g, 66.3 mmol) and (R)-3-methylmorpholine (2.46 g, 24.3 mmol) were added to a solution of 5,7-dichloro-1,6-naphthyridine (4.4 g, 22.1 mmol) in dimethyl sulfoxide (73 mL), and the reaction system was stirred overnight at 110° C. Then the reaction mixture was cooled to room temperature, quenched with ice water, and the aqueous phase was extracted with ethyl acetate, and the combined organic phases were washed with saturated brine, dried over anhydrous sodium sulfate, filtered, then the filtrate was concentrated under reduced pressure, and the residue was purified by flash column chromatography (ethyl acetate/petroleum ether=0-1/1) to obtain compound 9.1 (5.1 g, yield: 87%) as a yellow solid. m/z: $[M+H]^+$ 264.2.

Step 2: Compound 9.1 (1.5 g, 5.69 mmol), dimethyl sulfoxide (20 mL) and cesium fluoride (1.73 g, 11.4 mmol) were sequentially added to a sealed tube, and the reaction system was stirred at 145° C. for 3 days. Then the reaction mixture was cooled to room temperature, quenched with ice water, and the aqueous phase was extracted with ethyl acetate, and the combined organic phases were washed with saturated brine, dried over anhydrous sodium sulfate, filtered, then the filtrate was concentrated under reduced pressure, and the residue was purified by flash column chromatography (ethyl acetate/petroleum ether=0-1/1) to obtain compound 9.2 (0.9 g, yield: 64%) as a yellow solid. m/z: $[M+H]^+$ 248.2.

Step 3: Palladium on carbon (10%, 0.85 g) was added to a solution of compound 9.2 (0.85 g, 3.44 mmol) in methanol (50 mL). The reaction system was purged with hydrogen and stirred overnight at room temperature under a hydrogen atmosphere. Then the reaction mixture was filtered with diatomite, and the filter cake was washed with methanol. The filtrates were combined and concentrated under reduced pressure, and the residue was purified by flash column chromatography (ethyl acetate/petroleum ether=0-1/1) to obtain compound 9.3 (0.64 g, yield: 74%) as a colorless oil. m/z: $[M+H]^+$ 252.2.

Step 4: Under an ice bath, methanesulfonyl chloride (2.8 mL) was added to a solution of compound 9.3 (0.53 g, 2.11 mmol) in anhydrous pyridine (7 mL), and the reaction solution was stirred in a sealed tube at 40° C. for 2 hours, then directly concentrated under reduced pressure. The residue was poured into water, and the aqueous phase was extracted with ethyl acetate. The combined organic phases were washed with saturated brine, dried over anhydrous sodium sulfate, filtered, and the filtrate was concentrated under reduced pressure, and the residue was purified by flash column chromatography (ethyl acetate/petroleum ether=0-1/1) to obtain compound 9.4 (0.33 g, yield: 48%) as a yellow oil. m/z: $[M+H]^+$ 330.2.

Step 5: Under a nitrogen atmosphere, phosphorus oxychloride (0.38 g, 2.5 mmol) was added dropwise to a solution of compound 9.4 (0.33 g, 1 mmol) in N,N-dimethylformamide (5 mL), and the reaction system was stirred at 80° C. for 4 hours. Then water was added to quench the reaction and the reaction mixture was stirred for 1 hour. The aqueous phase was adjusted to pH=7-8 with saturated sodium bicarbonate aqueous solution, then the aqueous phase was extracted with ethyl acetate, and the organic phases were combined and washed with saturated brine, then the organic phase was separated and dried over anhydrous sodium sulfate, filtered. The filtrate was concentrated under reduced pressure, and the residue was purified by flash column chromatography (ethyl acetate/petroleum ether=0-2/1) to obtain compound 9.5 (221 mg, yield: 62%) as a yellow solid. m/z: $[M+H]^+$ 358.2.

Step 6: 3-Hydrazino-1H-pyrazole (0.27 g, 2.8 mmol) was added to a solution of compound 9.5 (0.25 g, 0.7 mmol) in ethanol (95%, 5 mL), and the reaction system was stirred at room temperature for 20 minutes. Then the reaction mixture was concentrated under reduced pressure, and water (5 mL) was added to the residue. The aqueous phase was adjusted to pH=7-8 with saturated sodium bicarbonate aqueous solution, then the aqueous phase was extracted with ethyl acetate, and the organic phases were combined and washed with saturated brine, then the organic phase was separated and dried over anhydrous sodium sulfate, filtered, and the filtrate was concentrated under reduced pressure to obtain compound 9.6 (0.3 g, yield: 98%) as a yellow solid. m/z: $[M+H]^+$ 438.2.

Step 7: Compound 9.6 (0.3 g, 0.69 mmol) was dissolved in N-methylpyrrolidone (3 mL), and the reaction system was purged with nitrogen for 3 times, and reacted under microwave at 180° C. for 20 minutes. Then the reaction mixture was cooled to room temperature, quenched with water, and the aqueous phase was extracted with ethyl acetate. The combined organic phases were concentrated under reduced pressure, and the residue was purified by prep-HPLC (acidic conditions) to obtain compound 9 (103 mg, yield: 28%) as an off-white solid. m/z: $[M+H]^+$ 418.2; $^1H$ NMR (400 MHz, DMSO-$d_6$): δ 8.13 (s, 1H), 7.86 (d, J=2.4 Hz, 1H), 6.81 (d, J=2.4 Hz, 1H), 3.84-3.70 (m, 6H), 3.68-3.62 (m, 1H), 3.49-3.42 (m, 1H), 3.34-3.27 (m, 1H), 3.26 (s, 3H), 3.03-2.93 (m, 1H), 2.88-2.77 (m, 1H), 2.71-2.61 (m, 1H), 2.12-2.00 (m, 1H), 1.88-1.75 (m, 1H), 1.02 (d, J=6.4 Hz, 3H).

Example 10: Synthesis of (R)-3-methyl-4-(9-(methylsulfonyl)-3-(1H-pyrazol-3-yl)-3H-pyrazolo[3,4-c]isoquinolin-5-yl)morpholine trifluoroacetate (Compound 10)

10

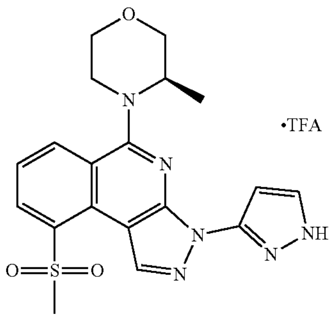

-continued

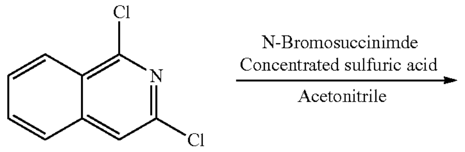

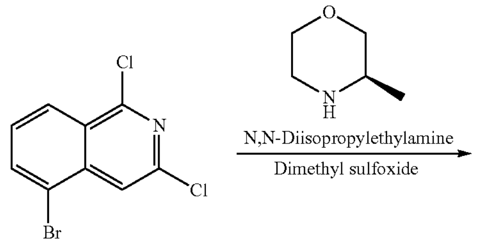

10.1

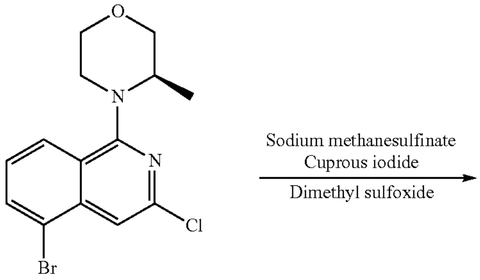

10.2

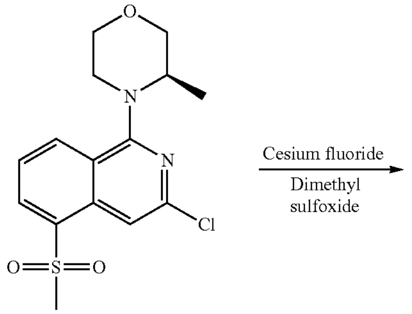

10.3

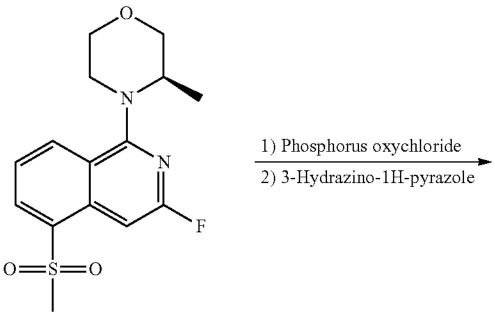

10.4

-continued

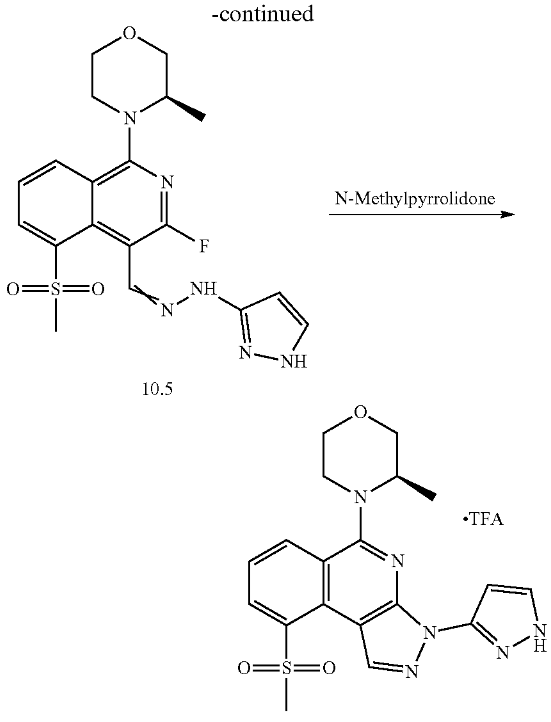

10.5

10

Step 1: Concentrated sulfuric acid (10 mL) and N-bromosuccinimide (10.8 g, 60.6 mmol) were added to a solution of 1,3-dichloroisoquinoline (10 g, 50.5 mmol) in acetonitrile (250 mL) respectively, and the reaction system was stirred at room temperature for 3 days. The reaction mixture was filtered and the filter cake was dried under vacuum to obtain compound 10.1 (7.4 g, yield: 53%) as a white solid. m/z: $[M+H]^+$ 275.8.

Step 2: N,N-Diisopropylethylamine (8.95 g, 69.2 mmol) and (R)-3-methylmorpholine (3.27 g, 32.3 mmol) were added to a solution of compound 10.1 (6.39 g, 23.1 mmol) in dimethyl sulfoxide (96 mL), and the reaction system was stirred at 110° C. overnight. Then the reaction mixture was cooled to room temperature, quenched with ice water, and the aqueous phase was extracted with ethyl acetate. The combined organic phases were washed with saturated brine, and the organic phase was separated and dried over anhydrous sodium sulfate, filtered, and the filtrate was concentrated under reduced pressure, and the residue was purified by flash column chromatography (petroleum ether/ethyl acetate=4/1) to obtain compound 10.2 (6.13 g, yield: 78%) as a yellow solid. m/z: $[M+H]^+$ 341.0.

Step 3: Sodium methanesulfinate (3.59 g, 35.1 mmol) and cuprous iodide (6.69 g, 35.1 mmol) were added to a solution of compound 10.2 (3 g, 8.78 mmol) in dimethyl sulfoxide (75 mL), and the reaction system was stirred at 120° C. for 6 hours under a nitrogen atmosphere. Then the reaction mixture was cooled to room temperature, poured into saturated ammonium chloride aqueous solution, then the aqueous phase was extracted with ethyl acetate. The organic phases were combined and washed with saturated brine, then the organic phase was separated and dried over anhydrous sodium sulfate, filtered, and the filtrate was concentrated under reduced pressure, the residue was purified by flash column chromatography (petroleum ether/ethyl acetate=1/2) to obtain compound 10.3 (1.8 g, yield: 60%) as a yellow solid. m/z: $[M+H]^+$ 341.0.

Step 4: Compound 10.3 (1.8 g, 5.29 mmol), dimethyl sulfoxide (25 mL) and cesium fluoride (2.41 g, 15.9 mmol) were sequentially added to a sealed tube, and the reaction system was stirred at 150° C. for 5 hours. Then the reaction mixture was cooled to room temperature, quenched with ice water, and the aqueous phase was extracted with ethyl acetate. The organic phases were combined and washed with saturated brine, then the organic phase was separated and dried over anhydrous sodium sulfate, filtered, and the filtrate was concentrated under reduced pressure, and the residue was purified by flash column chromatography (petroleum ether/ethyl acetate=0-1/2) to obtain compound 10.4 (1.03 g, yield: 60%) as a yellow solid. m/z: $[M+H]^+$ 325.0.

Step 5: A solution of phosphorus oxychloride (0.5 mL) in N,N-dimethylformamide (5 mL) was stirred at room temperature for 10 minutes, then compound 10.4 (100 mg, 0.31 mmol) was added to the above reaction solution, and the reaction system was stirred at 80° C. for 3 hours, cooled to room temperature, then the reaction solution was poured into ice water (20 mL), and stirred for 1 hour. Ethyl acetate (10 mL) was added thereto and the reaction mixture was adjusted to pH=8 with saturated sodium carbonate aqueous solution. 3-Hydrazino-1H-pyrazole (100 mg, 1.02 mmol) was added thereto. The resulting mixture was stirred overnight at room temperature, then water (10 mL) was added thereto, and the aqueous phase was extracted with ethyl acetate. The organic phases were combined and dried over anhydrous sodium sulfate, filtered, and the filtrate was concentrated under reduced pressure, and the residue was purified by prep-TLC (dichloromethane/methanol=10/1) to obtain compound 10.5 (70 mg, yield: 52%) as a yellow oil. m/z: $[M+H]^+$ 433.2.

Step 6: A solution of compound 10.5 (70 mg, 0.16 mmol) in N-methylpyrrolidone (2.1 mL) was reacted under microwave at 180° C. for 20 minutes in a sealed tube. The reaction solution was cooled to room temperature, and water (10 mL) was added to quench the reaction. The aqueous phase was extracted with ethyl acetate, and the combined organic phases were dried over anhydrous sodium sulfate, filtered, and the filtrate was concentrated under reduced pressure, and the residue was purified by prep-HPLC (acidic conditions) to obtain compound 10 (10 mg, yield: 15%) as a yellow solid. m/z: $[M+H]^+$ 413.2; $^1H$ NMR (400 MHz, $CDCl_3$) δ 9.05-9.07 (m, 1H), 8.61-8.68 (m, 2H), 7.76-7.78 (m, 1H), 7.67-7.71 (m, 1H), 7.10-7.12 (m, 1H), 4.05-4.08 (m, 3H), 3.91-3.95 (m, 1H), 3.68-3.72 (m, 2H), 3.35-3.38 (m, 1H), 3.31 (s, 3H), 1.22-1.24 (m, 3H).

Example 11: Synthesis of (R)-4-(1-cyclopropyl-6-(1H-pyrazol-3-yl)-1,2,3,6-tetrahydropyrazolo[3,4-b]pyrrolo[2,3-d]pyridin-4-yl)-3-methylmorpholine (Compound 11)

11

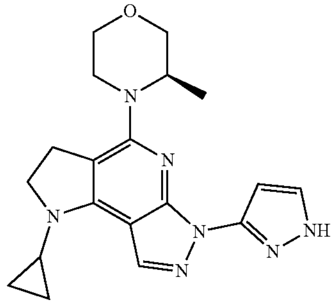

-continued

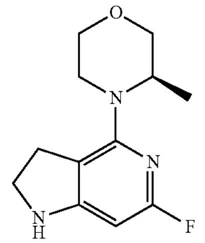

2.4

Cyclopropylboronic acid
Copper acetate
Acetonitrile

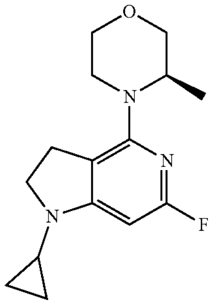

11.1

Phosphorus oxychloride
N,N-Dimethylformamide

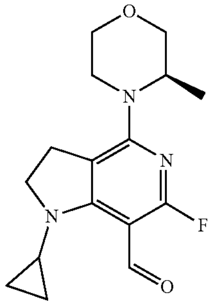

11.2

3-Hydrazino-1H-pyrazole
Ethanol

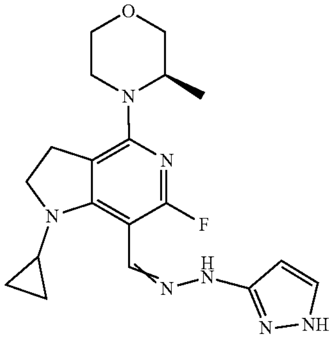

11.3

N-Methylpyrrolidone

-continued

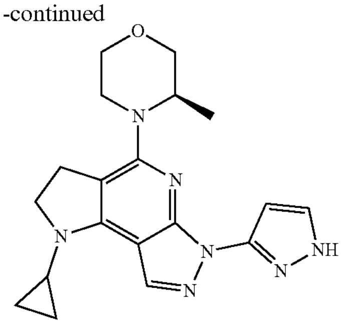

11

Step 1: Under a nitrogen atmosphere, cyclopropylboronic acid (180 mg, 2.1 mmol), copper acetate (191 mg, 1.05 mmol) and sodium carbonate (223 mg, 2.1 mmol) were added sequentially to a solution of compound 2.4 (250 mg, 1.05 mmol) in acetonitrile (6 mL), and the reaction system was stirred at 70° C. for 5 hours. After the reaction solution was cooled to room temperature, water was added to quench the reaction, and the aqueous phase was extracted with ethyl acetate. The organic phases were combined and dried over anhydrous sodium sulfate, filtered, and the filtrate was concentrated under reduced pressure, and the residue was purified by flash column chromatography (ethyl acetate/petroleum ether=0-1/2) to obtain compound 11.1 (220 mg, yield: 75%) as a pale yellow solid. m/z: $[M+H]^+$ 278.2.

Step 2: Under a nitrogen atmosphere, phosphorus oxychloride (0.3 g, 2.01 mmol) was added to the solution of compound 11.1 (220 mg, 0.8 mmol) in N,N-dimethylformamide (4 mL), and the reaction system was stirred at 80° C. for 4 hours, then after the reaction system was cooled to room temperature, ice water was added to quench the reaction and the stirring was continued for 2 hours. The aqueous phase was extracted with ethyl acetate, and the organic phases were combined and washed with water, then the organic phase was separated, dried over anhydrous sodium sulfate, filtered. The filtrate was concentrated under reduced pressure, and the residue was purified by flash column chromatography (ethyl acetate/petroleum ether=0-1/1) to obtain compound 11.2 (230 mg, yield: 94%) as a pale yellow solid. m/z: $[M+H]^+$ 306.2.

Step 3: 3-Hydrazino-1H-pyrazole (0.2 g, 2.0 mmol) was added to a solution of compound 11.2 (0.15 g, 0.49 mmol) in ethanol (95%, 6 mL), and the reaction system was stirred at room temperature for 0.5 hours. Water was added to quench the reaction, and the aqueous phase was adjusted to pH=7-8 with saturated sodium bicarbonate aqueous solution, then the aqueous phase was extracted with ethyl acetate. The organic phases were combined and washed with saturated brine, and the organic phase was separated, dried over anhydrous sodium sulfate, filtered, and the filtrate was concentrated under reduced pressure to obtain compound 11.3 (0.18 g, crude product) as a yellow solid.

Step 4: A solution of compound 11.3 (0.18 g, crude product) in N-methylpyrrolidone (3 mL) was purged with nitrogen for 3 times, and reacted under microwave at 180°

C. for 1 hour. Then the reaction mixture was cooled to room temperature, quenched with water, and the aqueous phase was extracted with ethyl acetate. The combined organic phases were concentrated under reduced pressure, and the residue was purified by prep-HPLC (alkaline conditions) to obtain compound 11 (22.3 mg, yield: 12%) as a light yellow solid. m/z: $[M+H]^+$ 366.2; $^1H$ NMR (400 MHz, $CDCl_3$): δ 8.19 (s, 1H), 7.60 (d, J=4.0 Hz, 1H), 6.71 (s, 1H), 4.20-3.98 (m, 2H), 3.80-3.76 (m, 1H), 3.70-3.48 (m, 6H), 3.16-2.98 (m, 2H), 2.68-2.60 (m, 1H), 1.34 (d, J=8.0 Hz, 3H), 0.92-0.80 (m, 4H).

Example 12: Synthesis of (R)-3-methyl-4-(1-methyl-6-(1H-pyrazol-3-yl)-tetrahydropyrazolo[3,4-b]pyrrolo[2,3-d]pyridin-4-yl)morpholine (Compound 12)

12

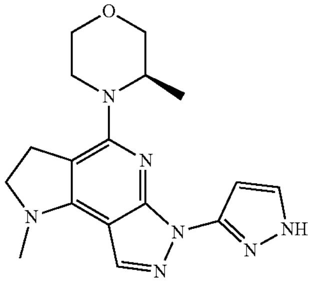

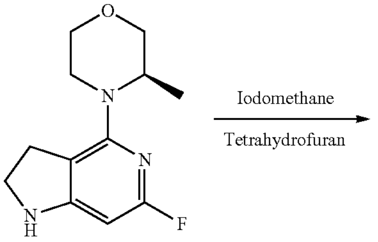

2.4

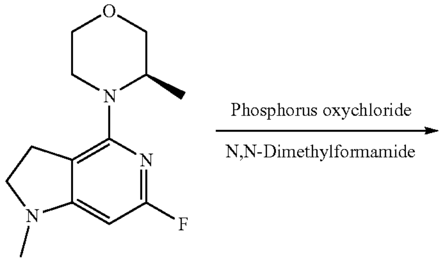

12.1

-continued

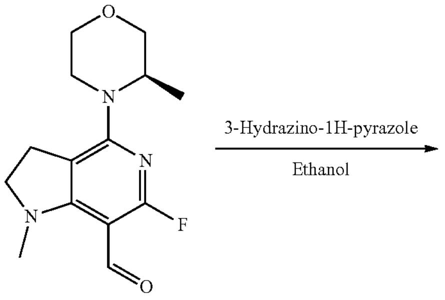

12.2

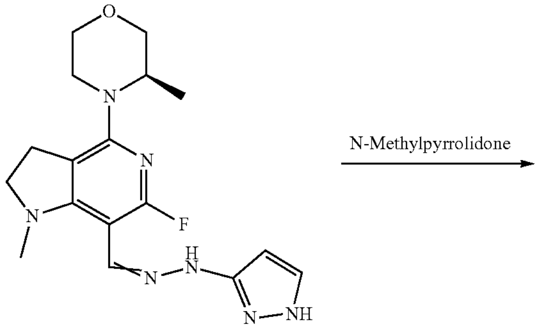

12.3

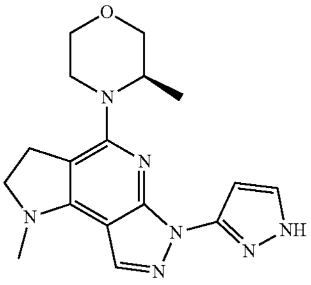

12

Step 1: Under an ice bath, sodium hydride (67.4 mg, 1.7 mmol) was added to a solution of compound 2.4 (200 mg, 0.84 mmol) in tetrahydrofuran (3 mL), and after the reaction system was stirred at 0° C. for 0.5 hours, iodomethane (470 mg, 3.4 mmol) was added thereto. The reaction solution was stirred at room temperature for 0.5 hours, quenched with water, and the aqueous phase was extracted with ethyl acetate, then the organic phases were combined and dried over anhydrous sodium sulfate, filtered. The filtrate was concentrated under reduced pressure, and the residue was purified by flash column chromatography (ethyl acetate/petroleum ether=0-1/2) to obtain compound 12.1 (170 mg, yield: 81%) as a pale yellow solid. m/z: $[M+H]^+$ 252.2.

Steps 2-4: Referring to the synthesis method of compound 11 in steps 2-4, compound 12 was obtained from compound 12.1 as a light yellow solid. m/z: $[M+H]^+$ 340.2; $^1H$ NMR (400 MHz, $CDCl_3$): δ 8.02 (s, 1H), 7.60 (d, J=4.0 Hz, 1H), 6.72 (s, 1H), 4.14-3.98 (m, 2H), 3.80-3.76 (m, 1H), 3.70-3.48 (m, 6H), 3.16-2.98 (m, 5H), 1.34 (d, J=8.0 Hz, 3H).

Example 13: Synthesis of (R)-4-(6-(1H-pyrazol-3-yl)-1-(pyridin-3-yl)-1,2,3,6-tetrahydropyrazolo[3,4-b]pyrrolo[2,3-d]pyridin-4-yl)-3-methylmorpholine trifluoroacetate (Compound 13)

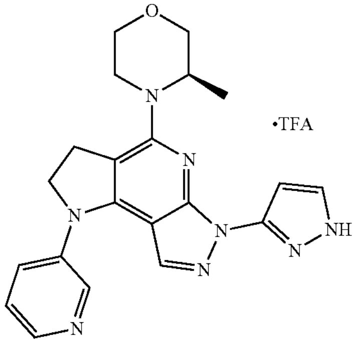

13

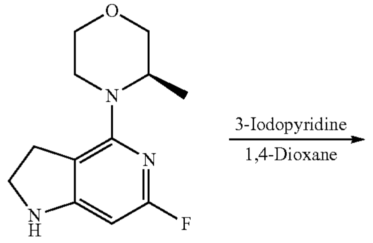

2.4

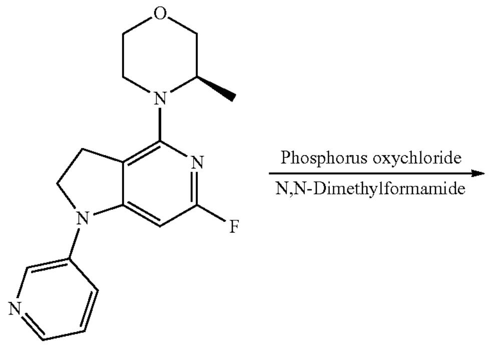

13.1

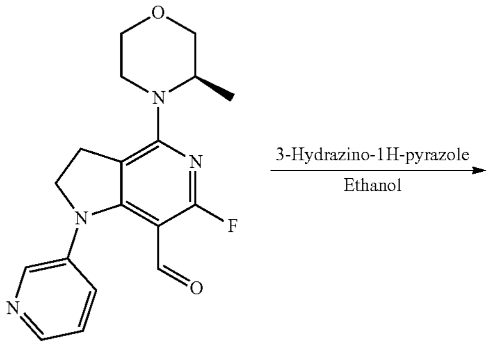

13.2

-continued

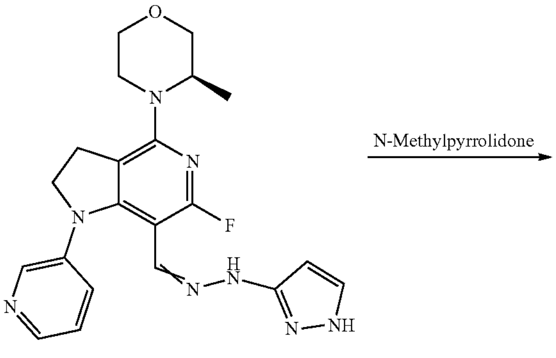

13.3

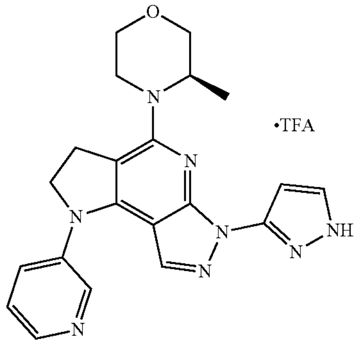

13

Step 1: 3-Iodopyridine (310 mg, 1.51 mmol), methanesulfonato(2-dicyclohexylphosphino-2',6'-di-i-propoxy-1,1'-biphenyl)(2'-amino-1,1'-biphenyl-2-yl)palladium(II) (158 mg, 0.19 mmol) and cesium carbonate (820 mg, 2.52 mmol) were sequentially added to a solution of compound 2.4 (300 mg, 1.26 mmol) in 1,4-dioxane (5 mL), and the reaction system was purged with nitrogen for 3 times, and then stirred at 110° C. for 16 hours under a nitrogen atmosphere. After the reaction system was cooled to room temperature, the reaction mixture was directly concentrated under reduced pressure, and the residue was purified by flash column chromatography (ethyl acetate/petroleum ether=0-2/3) to obtain compound 13.1 (190 mg, yield: 48%) as a yellow solid. m/z: $[M+H]^+$ 314.8.

Steps 2-4: Referring to the synthesis method of compound 11 in steps 2-4, compound 13 was obtained from compound 13.1 as a light yellow solid. m/z: $[M+H]^+$ 402.8; $^1H$ NMR (400 MHz, DMSO-$d_6$): δ 8.81 (d, J=2.4 Hz, 1H), 8.58-8.54 (m, 1H), 8.10-8.05 (m, 1H), 7.92-7.88 (m, 1H), 7.78-7.72 (m, 1H), 7.51 (s, 1H), 6.91 (d, J=2.4 Hz, 1H), 4.35-4.15 (m, 4H), 4.01-3.94 (m, 1H), 3.82-3.78 (m, 2H), 3.74-3.63 (m, 4H), 1.26 (d, J=6.4 Hz, 3H).

Example 14: Synthesis of (R)-2-(4-(3-methylmorpholinyl)-6-(1H-pyrazol-3-yl)-2,3-dihydropyrazolo[3,4-b]pyrrolo[2,3-d]pyridin-1(6H)-yl)ethanol trifluoroacetate (Compound 14)

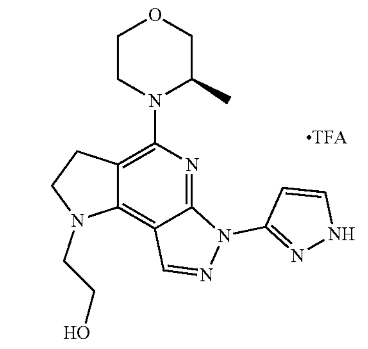

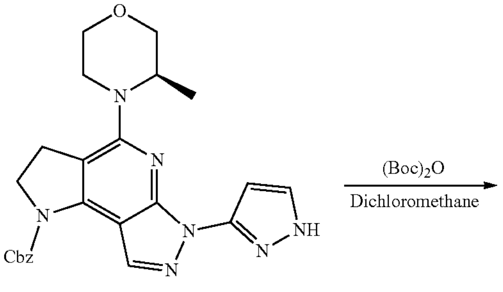

5.4

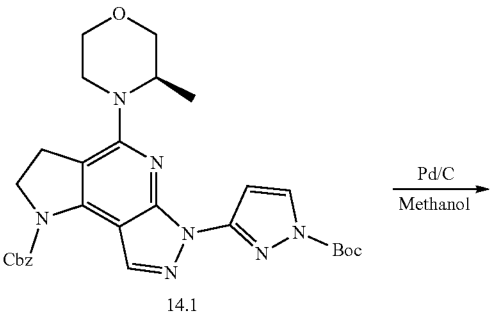

14.1

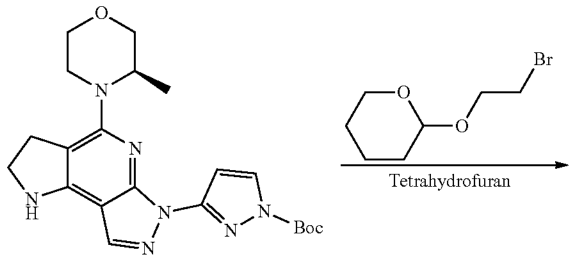

14.2

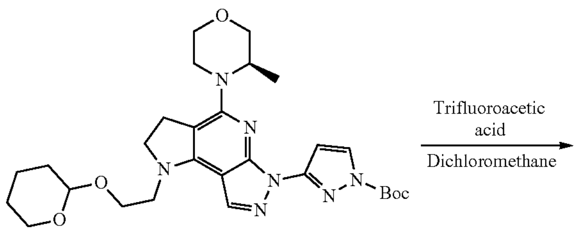

14.3

-continued

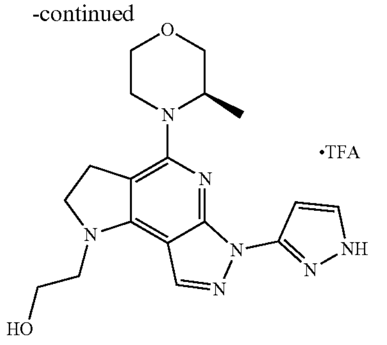

14

Step 1: Triethylamine (66 mg, 0.65 mmol), $(Boc)_2O$ (95.2 mg, 0.44 mmol) and 4-dimethylaminopyridine (2.4 mg, 0.02 mmol) were sequentially added to a solution of compound 5.4 (0.20 g, 0.44 mmol) in dichloromethane (2 mL), and the reaction mixture was stirred at room temperature for 2 hours. Water was added to quench the reaction, and the aqueous phase was extracted with ethyl acetate. The organic phases were combined and dried over anhydrous sodium sulfate, filtered, and the filtrate was concentrated under reduced pressure, and the residue was purified by flash column chromatography (ethyl acetate/petroleum ether-1/2) to obtain compound 14.1 (150 mg, yield: 61%) as a yellow solid.

Step 2: Pd/C (10%, 120 mg) was added to a solution of compound 14.1 (400 mg, 0.94 mmol) in methanol (5 mL), and the reaction system was purged with hydrogen and stirred at room temperature for 4 hours under a hydrogen atmosphere. The reaction solution was filtered, and the filtrate was concentrated under reduced pressure to obtain compound 14.2 (300 mg, yield: 71%) as a pale yellow foamy solid.

Step 3: Sodium hydride (56.4 mg, 1.4 mmol, 60%) was added to a solution of compound 14.2 (300 mg, 0.71 mmol) in tetrahydrofuran (3 mL), and the reaction solution was stirred at room temperature for 0.5 hours. 2-(2-Bromoethoxy)tetrahydro-2H-pyran (295 mg, 1.4 mmol) was added to the above reaction system, and the resulting mixture was stirred at room temperature for 6 hours, and water was added to quench the reaction, then the aqueous phase was extracted with ethyl acetate. The organic phases were combined and dried over anhydrous sodium sulfate, filtered, and the filtrate was concentrated under reduced pressure to obtain compound 14.3 (200 mg, yield: 51%) as a yellow oil.

Step 4: A mixed solution of compound 14.3 (50 mg, 0.09 mmol) in trifluoroacetic acid (1 mL) and dichloromethane (2 mL) was stirred at room temperature for 1 hour, then concentrated under reduced pressure, and the residue was purified by prep-HPLC (acidic conditions) to obtain compound 14 (1.7 mg, yield: 4%) as a light yellow solid. m/z: $[M+H]^+$ 370.2; $^1H$ NMR (400 MHz, $CD_3OD$): δ 8.07 (s, 1H), 7.81 (s, 1H), 6.69 (s, 1H), 4.32 (t, J=4.0 Hz, 2H), 3.95-4.00 (m, 6H), 3.76 (d, J=12.0 Hz, 1H), 3.34-3.74 (m, 4H), 3.26-3.30 (m, 1H), 1.28-1.38 (m, 3H).

Biological Example

Example 1: ATR Enzyme Assay

In this experiment, the phosphorylation level of substrate protein P53 (Eurofins, 14-952) was detected by HTRF technology to measure the activity of ATR/ATRIP (Eurofins, 14-953) kinase. Reaction buffer (25 mM HEPES pH 8.0, 0.01% Brij-35, 1% Glycerol, 5 mM DTT, 1 mg/mL BSA), termination buffer (12.5 mM HEPES pH 8.0, 0.005% Brij-35, 0.5% Glycerol, 250 mM EDTA) and assay buffer (50 mM HEPES pH 7.0, 150 mM NaCl, 267 mM KF, 0.1% sodium cholate, 0.01% Tween 20) were prepared in advance. ATR/ATRIP was diluted with reaction buffer to a working solution of 2 ng/μL, and the substrate protein P53 was diluted with reaction buffer to a working solution of 80 nM, and 4 nM of ATP (Sigma, A2383) working solution (containing 40 mM $MnCl_2$) was prepared with reaction buffer. The compound was 3-fold diluted with DMSO, then diluted with reaction buffer into a working solution, then added to a 384-well plate at 2.5 μL/well, and centrifuged at 1500 rpm for 40 s. Then 2.5 μL of ATR/ATRIP working solution, P53 working solution and ATP working solution were added into the 384-well plate, centrifuged at 1500 rpm for 40 s and reacted at room temperature for 30 minutes. After the reaction was completed, 5 μL of termination buffer was added to each well, and centrifuged at 1500 rpm for 40 s. Antibody working solution containing 0.083 μg/mL anti-phospho-p53 (Ser15)-K (CisBio, cat. 61P08KAE) and 5 μg/mL anti-GST-d2 (CisBio, cat. 61GSTDLA) was prepared with assay buffer and added to the 384-well plate at 5 μL/well, then centrifuged at 1500 rpm for 40 s and reacted overnight at room temperature. Microplate reader (Tecan, Infinite M1000 Pro) was used to detect TR-FRET, and the data were analyzed with Graphpad software, and the four-parameter equation was used to fit the curve and calculate the $IC_{50}$ value of the inhibitor (Table 1).

TABLE 1

| Compound number | $IC_{50}$ (nM) |
|---|---|
| 1 | 1.2 |
| 2 | 0.69 |
| 3 | 0.51 |
| 4 | 1.8 |
| 5 | 6.5 |
| 6 | 4.8 |
| 7 | 46 |
| 8 | 40 |
| 11 | 5.9 |
| 12 | 14 |
| 13 | 7.5 |

Example 2: Cell Proliferation Assay

In the present disclosure, cell assays were used to evaluate the biological activity of compounds. LOVO (Nanjing Cobioer), a human colon cancer cell line, was cultured in a Dulbecco's Modified Eagle's medium 96-well plate, supplemented with 10% fetal bovine serum and 1% P/S, and the culture environment was 37° C. and 5% $CO_2$. Compound concentrations were ranged from 4.5 nM to 30 μM. The stock solution of the test compound was dissolved in DMSO and added to the medium at the indicated concentration, and incubated for 72 hours. Negative control cells were treated with vehicle only. In some experiments, known ATR inhibitors were added as positive controls. Cell viability was evaluated using the Cell titer glo kit (CTG, Promega) under the instructions of the product specification. The data were analyzed using Graphpad software, and $IC_{50}$ values and compound fitting curves were obtained (Table 2).

TABLE 2

| Compound number | $IC_{50}$ (nM) |
|---|---|
| 1 | 29.62 |
| 2 | 37.34 |
| 5 | 261.7 |
| 6 | 79.57 |
| 7 | 405.8 |
| 8 | 32.28 |
| 11 | 71.95 |
| 12 | 93.65 |

Example 3: Cytochrome Oxidase P450 Inhibition Study

LC-MS/MS methods were used to evaluate the inhibitory effects of compounds on CYP2C19, 2D6 and 3A4 subtypes. In this method, the test compound was mixed with a solution of human liver microsomes containing CYP model substrates, and incubated together under the addition of NADPH, then the inhibitory $IC_{50}$ of the compound on CYP2C19, 2D6 and 3A4 was calculated by measuring the amount of metabolites of the model substrate in the reaction solution. The specific experimental method is as follows:

Compounds to be tested were prepared as stock solutions at 10 mM concentration with DMSO and then diluted to 4 mM with acetonitrile solution. At the same time, the corresponding reference inhibitor solutions for CYP subtypes were prepared, for example, the reference inhibitor was Ketoconazole, then these two compounds were prepared separately (8 mL of inhibitor DMSO stock solution+12 mL of acetonitrile), and the samples prepared under the above conditions were at 400× concentration. Then, the above solution was 3-fold diluted with DMSO/acetonitrile mixture (v/v: 40/60) to prepare the final test solution, and seven concentration points were set for each test compound, and the initial test final concentration was 10 μM. NADPH, CYP enzyme model substrate and human liver microsome solution were diluted to appropriate concentrations with pre-warmed potassium phosphate buffer (0.1 M, pH 7.4), respectively. The human liver microsome solution was purchased from BD Gentest (20 mg/mL, Corning, article number #452161).

400 mL of human liver microsome solution (0.2 mg/mL) was added to each well containing the test compound in the 96-well plate, and then 2 mL of the final test sample of test compounds prepared by serial dilution as described above was added thereto; for each well corresponding to the reference inhibitors, 200 mL of human liver microsome solution (0.2 mg/mL) and 1 mL of the final test sample were added. 15 mL of the prepared corresponding model substrate was dispensed into a 96-well plate, and the microsome solution was mixed evenly, then 30 mL of the test compound/reference inhibitor-human liver microsome mixture was taken and transferred to the 96-well plate containing the substrate, and the mixture was mixed well and preheated at 37° C. for 5 minutes, then 15 mL of 8 mM NADPH solution preheated at 37° C. was added thereto to start the reaction. A duplicate well control and a blank control without the addition of test substances were set at the same time. The 96-well plate containing a total volume of 60 mL of reaction solution was incubated at 37° C. After the incubation, 120 μL of cold acetonitrile solution containing internal standard was added to each well to terminate the reaction, and then the 96-well plate was shaked on a microplate shaker for 5 minutes (600 rpm/min), and put into a centrifuge and centrifuged for 20 minutes at 6000 rpm, 4° C. Then 40 μL of supernatant from each well was transferred to another 96-well plate, and 80 μL of ultrapure water was added to each well, put into a shaker and mixed for 5 minutes (600 rpm/min), and centrifuged at 6000 rpm, 4° C., for 20 minutes. Then LC-MS/MS detection was performed. The inhibition rate was determined by comparing the amount of model substrate metabolites at each test concentration without test substance addition, in the GraphPad Prism 5.0 software, the logarithm of the test concentration was used as the abscissa and the inhibition rate was used as the ordinate to perform a linear regression (Sigmoidal (non-linear) dose-response model) analysis to obtain the $IC_{50}$ value of the test compound. The results are shown in Table 3 below:

TABLE 3

| Compound | $IC_{50}$ (μM) | | | |
|---|---|---|---|---|
| number | 2C19 | 2D6 | 3A4 (Midazolam) | 3A4 (Testosterone) |
| 1 | >10 | >10 | >10 | >10 |
| 2 | >10 | >10 | >10 | >10 |
| 3 | >10 | >10 | >10 | >10 |

Example 4: Cardiac Safety Evaluation-hERG Study

In this experiment, a CHO cell line stably transfected with hERG cDNA and expressing p15 hERG channel was used. Cells were incubated at 37° C. in a humidified incubator containing 5% $CO_2$ in medium (Ham's F12, 10% v/v FBS, 100 μg/mL hygromycin B, 100 μg/mL geneticin) (from Invitrogen). Cells were grown under the above conditions and reached approximately 80-90% of the confluency. Cells were treated with Detachin (Genlantis) for 3 to 5 minutes. The medium was titrated 15 to 20 times at 37° C., and then the cells were resuspended in CHO-S-SFM II medium (serum-free medium, Invitrogen) buffered with HEPES (25 mM). Cells used for QPatch studies must meet the following criteria: Most suspension cells should be single and isolated under microscopy; viability should be greater than 95%; cell density in the final suspension should be in the range of 3 to $8\times10^6$ cells/mL before application to the QPatch stir chamber. Cells meeting the above conditions can be used for recordings within 4 hours of harvest.

Test compounds were made into 10 mM DMSO stock solutions. Six doses (30, 10, 3, 1, 0.3 and 0.1 μM) were selected to obtain the fitted curves and $IC_{50}$. The final DMSO concentration was 0.1% or less. The $IC_{50}$ of the positive control cisapride was assessed at doses of 3, 1, 0.3, 0.1, 0.03 and 0.01 μM, respectively. Composition of internal solution for electrophysiological recordings: $CaCl_2$ 2 mM, $MgCl_2$ 1 mM, KCl 4 mM, NaCl 145 mM, Glucose 10 mM, HEPES 10 mM, pH 7.4 (NaOH), composition of external solution: $CaCl_2$ 374 mM, $MgCl_2$ 1.75 mM, KCl 120 mM, HEPES 10 mM, EGTA 5 mM, Na-ATP 4 mM, pH 7.25 (KOH) (all reagents used were from sigma).

Whole-cell recordings were performed using automated QPatch (Sophion Biosciences, Denmark). Cells were recorded for 120 s to assess current stability. The above voltages were then applied to the cells every 15 s throughout the procedure. Only stable cells with recording parameters above the threshold were allowed for the drug testing procedure. All experiments were performed at about 25° C. An external solution containing 0.1% DMSO (vehicle) was applied to the cells to establish a baseline. After the current was stabilized for 3 minutes, the test compounds were tested. Compounds solutions were added and cells were maintained in the test solution until the effect of the compound reached a steady state, a maximum of 4 minutes. For dose-effect determination, compounds were applied to cells cumulatively from low to high concentrations. Compounds were rinsed with external solution after test.

The data were analyzed with Sophion Assay software (determination software V5.0), Microsoft Excel and Graphpad Prism 5.0 to obtain $IC_{50}$ of compounds. The results are shown in Table 4 below:

TABLE 4

| Compound number | $IC_{50}$ (μM) |
|---|---|
| 1 | >30 |
| 2 | >30 |
| 3 | >30 |

Example 5: In Vivo Drug Efficacy Experiment of OCI-LY19 Human B-Cell Lymphoma Mouse Subcutaneous Xenograft Tumor Model Cell culture: Human B-cell lymphoma OCI-LY19 cells were maintained as a monolayer in MEM-α medium containing 10% fetal bovine serum in a constant temperature incubator at 37° C. with 5% $CO_2$. Tumor cells were subcultured twice a week. Cells in exponential growth phase were harvested and counted for inoculation.

Experimental animals: BALB/c nude mice, 6-8 weeks old, 19-22 g, purchased from Beijing Vital River Laboratory Animal Technology Co., Ltd.

For Vehicle, positive control (AZD6738, CAS number: 1352226-88-0) and compound 2, a total of 6 experimental groups were set up, as shown in Table 5 below:

TABLE 5

| Group | Number of mice | Test compound | Dose | Method of adminis-tration | Administration plan |
|---|---|---|---|---|---|
| 1 | 6 | Vehicle | — | p.o. | Once a day |
| 2 | 6 | AZD6738 | 20 mg/kg | p.o. | Once a day |
| 3 | 6 | Compound 2 | 5 mg/kg | p.o. | Once a day |
| 4 | 6 | Compound 2 | 10 mg/kg | p.o. | Once a day |
| 5 | 6 | Compound 2 | 10 mg/kg | p.o. | Once a day × 4 days on, 3 days off |
| 6 | 6 | Compound 2 | 20 mg/kg | p.o. | Once a day × 4 days on, 3 days off |

Note:
p.o.: oral

Experimental method: The OCI-LY19 cell line ($3.0\times10^6$ cells/mouse) was inoculated subcutaneously on the right back of the experimental mouse, and the inoculation volume of each mouse was 0.1 mL, and the growth of tumors was observed regularly, and until the tumor grew to about 100 $mm^3$, the mice were randomly divided into groups according to the tumor size and body weight, and administered according to the administration plan shown in Table 5, and the mouse body weight and tumor size were measured twice a week during the whole experiment.

tumor volume ($mm^3$)=0.5×(tumor long diameter×tumor short diameter$^2$). Tumor size calculation formula:

The experimental results are shown in Table 6 and FIG. 1:

TABLE 6

| Group | Tumor volume (10 days, $mm^3$) | Tumor volume (24 days, $mm^3$) | TGI (%) | T/C (%) | P value |
|---|---|---|---|---|---|
| 1 | 109.44 ± 5.31 | 2367.10 ± 538.09 | N/A | N/A | N/A |
| 2 | 108.23 ± 4.67 | 738.65 ± 257.29 | 72.1 | 31.2 | 0.0212 |
| 3 | 109.41 ± 4.35 | 424.51 ± 77.26 | 86.0 | 17.9 | 0.0051 |
| 4 | 109.00 ± 4.19 | 202.09 ± 44.85 | 95.9 | 8.5 | 0.0025 |
| 5 | 109.20 ± 3.96 | 375.56 ± 92.96 | 88.2 | 15.9 | 0.0045 |
| 6 | 109.24 ± 4.22 | 187.91 ± 27.01 | 96.5 | 7.9 | 0.0023 |

The results show that: Compared with the positive control AZD6738, the compounds of the present disclosure can show better drug efficacy on the OCI-LY19 human B-cell lymphoma mouse subcutaneous xenograft tumor model.

The invention claimed is:

1. A compound of formula (II) or a compound of formula (III), a stereoisomer or a pharmaceutically acceptable salt thereof;

(II)

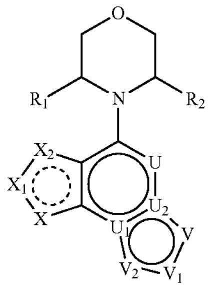

or (III)

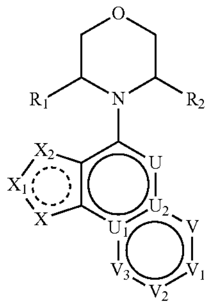

in the compound of formula (II), any one of the following conditions (1)-(3) is satisfied:

(1) $U_1$ and $U_2$ are C respectively: V is $NR_6$: $V_1$ is N or $CR_{7a}$; and $V_2$ is N or $CR_{7b}$;

(2) $U_1$ is C: $U_2$ is N: V is $CR_7$; $V_1$ is N or $CR_{7a}$; and $V_2$ is N or $CR_{7b}$; and (3) $U_1$ is N: $U_2$ is C: V is $CR_7$; $V_1$ is N or $CR_{7a}$; and $V_2$ is N or $CR_{7b}$;

in the compound of formula (III): $U_1$ and $U_2$ are each independently C; V is $CR_7$; $V_1$ is N or $CR_{7a}$; $V_2$ is N or $CR_{7b}$; and $V_3$ is N or $CR_{7c}$;

in each of the compound of formula (II) and the compound of formula (III):

X is $CR_3$ or $NR_5$; $X_1$ is $CR_{3a}$, $CR_{3a}R_{4a}$ or $NR_{5a}$; $X_2$ is $CR_{3b}$, $CR_{3b}R_{4b}$ or $NR_{5b}$;

U is N or CH;

$R_1$ is hydrogen or $C_{1-6}$ alkyl;

$R_2$ is methyl;

$R_3$, $R_{3a}$ and $R_{3b}$ are each independently hydrogen, halogen, cyano, nitro, $C_{1-6}$ alkyl, $C_{2-6}$ alkynyl, $C_{2-6}$ alkenyl, $C_{6-10}$ aryl, $C_{3-8}$ cycloalkyl, 3- to 8-membered heterocycloalkyl, 5- to 6-membered heteroaryl, $C_{6-10}$ aryl-$C_{1-6}$ alkyl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, —$SR_a$, —$OR_a$, —$OC(O)R_a$, —$OC(O)OR_a$, —$OC(O)NR_aR_b$, —$C(O)OR_a$, —$C(O)R_a$, —$C(O)NR_aR_b$, —$C(O)N(R_b)OR_a$, —$C(O)NR_bS(O)_2R_a$, —$C(=NH)R_a$, —$NR_aR_b$, —$NR_bC(O)R_a$, —$N(R_b)C(O)OR_a$, —$N(R_b)C(O)NR_aR_b$, —$NR_bS(O)_2R_a$, —$NR_bC(=NH)R_a$, —$NR_bC(=NH)NR_bR_a$, —$S(O)_{1-2}R_a$, —$S(O)_2NR_aR_b$, —$S(O)(=NCN)R_a$, —$S(O)(=NR_b)R_a$ or —$NR_bS(O)_2NR_aR_b$; wherein, the $C_{1-6}$ alkyl, $C_{2-6}$ alkynyl, $C_{2-6}$ alkenyl, $C_{6-10}$ aryl, $C_{3-8}$ cycloalkyl, 3- to 8-membered heterocycloalkyl, 5- to 6-membered heteroaryl, $C_{6-10}$ aryl-$C_{1-6}$ alkyl, $C_{3-8}$ cycloalkyl-$C_{1-6}$ alkyl, 3- to 8-membered heterocycloalkyl-$C_{1-6}$ alkyl, or 5- to 6-membered heteroaryl-$C_{1-6}$ alkyl is unsubstituted or optionally substituted at any position by 1 to 3 of the following substituents selected from halogen, cyano, nitro, —$SR_a$, —$OR_a$, —$OC(O)R_a$, —$OC(O)OR_a$, —$OC(O)NR_aR_b$, —$C(O)OR_a$, —$C(O)R_a$, —$C(O)NR_aR_b$, —$C(O)NR_bS(O)_2R_a$, —$NR_aR_b$, —$NR_bC(O)R_a$, —$N(R_b)C(O)OR_a$, —$N(R_b)C(O)NR_aR_b$, —$NR_bC(=NH)R_a$, —$NR_bC(=NH)NR_aR_a$, —$NR_bS(O)_2R_a$, —$NR_bS(O)_2NR_aR_b$, —$S(O)_{1-2}R_a$, —$S(O)_2NR_aR_b$, —$S(O)(=NCN)R_a$ and —$S(O)(=NR_b)R_a$;

$R_{4a}$ and $R_{4b}$ are each independently hydrogen, halogen, $C_{1-6}$ alkyl, $C_{1-6}$ alkoxy, halo $C_{1-6}$ alkyl or halo $C_{1-6}$ alkoxy;

$R_5$, $R_{5a}$ and $R_{5b}$ are each independently hydrogen, $C_{1-6}$ alkyl, $C_{2-6}$ alkynyl, $C_{2-6}$ alkenyl, $C_{6-10}$ aryl, $C_{3-8}$ cycloalkyl, 3- to 8-membered heterocycloalkyl, 5- to 6-membered heteroaryl, $C_{6-10}$ aryl-$C_{1-6}$ alkyl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, —$SR_a$, —$OR_a$, —$C(O)OR_a$, —$C(O)R_a$, —$C(O)NR_aR_b$, —$C(O)N(R_b)OR_a$, —$C(O)NR_bS(O)_2R_a$, —$C(=NH)R_a$, —$S(O)_{1-2}R_a$, —$S(O)_2NR_aR_b$, —$S(O)(=NCN)R_a$ or —$S(O)(=NR_b)R_a$; wherein, the $C_{1-6}$ alkyl, $C_{2-6}$ alkynyl, $C_{2-6}$ alkenyl, $C_{6-10}$ aryl, $C_{3-8}$ cycloalkyl, 3- to 8-membered heterocycloalkyl, 5- to 6-membered heteroaryl, $C_{6-10}$ aryl-$C_{1-6}$ alkyl, $C_{3-8}$ cycloalkyl-$C_{1-6}$ alkyl, 3- to 8-membered heterocycloalkyl-$C_{1-6}$ alkyl, or 5- to 6-membered heteroaryl-$C_{1-6}$ alkyl is unsubstituted or optionally substituted at any position by 1 to 3 of the following substituents selected from halogen, cyano, nitro, —$SR_a$, —$OR_a$, —$OC(O)R_a$, —$OC(O)OR_a$, —$OC(O)NR_aR_b$, —$C(O)OR_a$, —$C(O)R_a$, —$C(O)NR_aR_b$, —$C(O)NR_bS(O)_2R_a$, —$NR_aR_b$, —$NR_bC(O)R_a$, —$N(R_b)C(O)OR_a$, —$N(R_b)C(O)NR_aR_b$, —$NR_bC(=NH)R_a$, —$NR_bC(=NH)NR_aR_b$, —$NR_bS(O)_2R_a$, —$NR_bS(O)_2NR_aR_b$, —$S(O)_{1-2}R_a$, —$S(O)_2NR_aR_b$, —$S(O)(=NCN)R_a$ and —$S(O)(=NR_b)R_a$;

$R_6$ is hydrogen, $C_{1-6}$ alkyl, $C_{1-6}$ alkoxy, halo $C_{1-6}$ alkyl, halo $C_{1-6}$ alkoxy, $C_{3-8}$ cycloalkyl, 3- to 8-membered heterocycloalkyl, $C_{6-10}$ aryl, 5- to 10-membered heteroaryl, $C_{3-8}$ cycloalkyl-$C_{1-6}$ alkyl, or 3- to 8-membered heterocycloalkyl-$C_{1-6}$ alkyl, wherein, the $C_{6-10}$ aryl or 5- to 10-membered heteroaryl is unsubstituted or optionally substituted at any position by 1 to 3 of the following substituents selected from halogen, cyano, —$R_c$, —$OR_c$, —$NR_cR_d$, —$N(CN)R_c$, —$N(OR_d)R_c$, —$S(O)_{0-2}R_c$, —$C(O)R_c$, —$C(O)OR_c$, —$C(O)NR_cR_d$, —$C(NH)NR_cR_d$, —$NR_dC(O)R_c$, —$NR_dC(O)NR_cR_d$, —$NR_dS(O)_2R_c$ and —$OC(O)R_c$;

$R_7$, $R_{7a}$, $R_{7b}$ and $R_{7c}$ are each independently hydrogen, halogen, cyano, $C_{1-6}$ alkyl, $C_{1-6}$ alkoxy, halo $C_{1-6}$ alkyl, halo $C_{1-6}$ alkoxy, $C_{3-8}$ cycloalkyl, 3- to 8-member heterocycloalkyl, $C_{6-10}$ aryl, 5- to 10-membered heteroaryl, $C_{3-8}$ cycloalkyl-$C_{1-6}$ alkyl or 3- to 8-membered heterocycloalkyl-$C_{1-6}$ alkyl, wherein, the $C_{6-10}$ aryl or 5- to 10-membered heteroaryl is unsubstituted or optionally substituted at any position by 1 to 3 of the following substituents selected from halogen, cyano, —$R_c$, —$OR_c$, —$NR_cR_d$, —$N(CN)R_c$, —$N(OR_d)R_c$, —$S(O)_{0-2}R_c$, —$C(O)R_c$, —$C(O)OR_c$, —$C(O)NR_cR_d$, —$C(NH)NR_cR_d$, —$NR_dC(O)R_c$, —$NR_dC(O)NR_cR_d$, —$NR_dS(O)_2R_c$ and —$OC(O)R_c$;

each of $R_a$, $R_b$, $R_c$ and $R_d$ is independently hydrogen, $C_{1-6}$ alkyl, $C_{2-6}$ alkenyl, $C_{2-6}$ alkynyl, $C_{3-8}$ cycloalkyl, 3- to 8-membered heterocycloalkyl, $C_{6-10}$ aryl, 5- to 6-membered heteroaryl, $C_{3-8}$ cycloalkyl-$C_{1-6}$ alkyl, 3- to 8-membered heterocycloalkyl-$C_{1-6}$ alkyl, phenyl-$C_{1-6}$ alkyl, or 5- to 6-membered heteroaryl-$C_{1-6}$ alkyl; the $R_a$, $R_b$, $R_c$ and $R_d$ are unsubstituted or optionally substituted at any position by 1 to 3 of the following substituents selected from halogen, hydroxyl, amino, carboxyl, $C_{1-6}$ alkyl, $C_{1-6}$ alkoxy, $C_{1-6}$ alkylamino, halo $C_{1-6}$ alkyl, halo $C_{1-6}$ alkoxy, $C_{2-6}$ alkenyl and $C_{2-6}$ alkynyl.

2. The compound, the stereoisomer or the pharmaceutically acceptable salt thereof of claim 1, wherein, the compound satisfies any one of the following conditions:

(1) U is N; and (2) $R_1$ is hydrogen.

3. The compound, the stereoisomer or the pharmaceutically acceptable salt thereof of claim 1, wherein, the compound satisfies any one of the following conditions:

(1) $R_3$ is $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, —$NR_bS(O)_2R_a$, —$S(O)_{1-2}R_a$, —$S(O)_2NR_aR_b$, —$S(O)(=NCN)R_a$ or —$S(O)(=NR_b)R_a$; wherein, the $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, or 3- to 8-membered heterocycloalkyl-$C_{1-6}$ alkyl is unsubstituted or optionally substituted at any position by 1 to 3 of the following substituents selected from halogen, —CN, —$SR_a$, —$OR_a$, —$C(O)OR_a$, —$C(O)R_a$, —$C(O)NR_aR_b$, —$NR_aR_b$, —$NR_bC(O)R_a$, —$NR_bS(O)_2R_a$, —$S(O)_{1-2}R_a$, —$S(O)_2NR_aR_b$, —$S(O)(=NCN)R_a$ and —$S(O)(=NR_b)R_a$;

(2) $R_{3a}$ and $R_{3b}$ are each independently hydrogen, halogen, cyano, $C_{1-6}$ alkyl, halo $C_{1-6}$ alkyl or halo $C_{1-6}$ alkoxy;

(3) $R_{4a}$ and $R_{4b}$ are each independently hydrogen or $C_{1-6}$ alkyl;

(4)$R_5$ is $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, 3- to 8-membered heterocycloalkyl-$C_{1-6}$ alkyl, 5- to 6-membered heteroaryl-$C_{1-6}$ alkyl, —$S(O)_{1-2}R_a$, —$S(O)_2NR_aR_b$, —$S(O)(=NCN)R_a$ or —$S(O)(=NR_b)R_a$; wherein, the $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, or 3- to 8-membered heterocycloalkyl-$C_{1-6}$ alkyl is unsubstituted or optionally substituted at any position by 1 to 3 of the following substituents selected from halogen, —CN, —$SR_a$, —$OR_a$, —$C(O)OR_a$, —$C(O)R_a$, —$C(O)NR_aR_b$, —$NR_aR_b$, —$NR_bC(O)R_a$, —$NR_bS(O)_2R_a$, —$S(O)_{1-2}R_a$, —$S(O)_2NR_aR_b$, —$S(O)(=NCN)R_a$ and —$S(O)(=NR_b)R_a$;

(5) $R_{5a}$ and $R_{5b}$ are each independently hydrogen, $C_{1-6}$ alkyl, halo $C_{1-6}$ alkyl or $C_{3-8}$ cycloalkyl;

(6)$R_6$ and $R_7$ are each independently 5- to 6-membered heteroaryl; the 5- to 6-membered heteroaryl is unsubstituted or optionally substituted at any position by 1 to 3 of the following substituents selected from halogen, cyano, —$R_c$, —$OR_c$, —$NR_cR_d$, —$N(CN)R_c$, —$N(OR_d)R_c$, —$S(O)_{0-2}R_c$, —$C(O)R_c$, —$C(O)OR_c$, —$C(O)NR_cR_d$, —$C(NH)NR_cR_d$, —$NR_dC(O)R_c$, —$NR_dC(O)NR_cR_d$, —$NR_dS(O)_2R_c$ and —$OC(O)R_c$;

(7) $R_{7a}$, $R_{7b}$ and $R_{7c}$ are each independently hydrogen, halogen, cyano, $C_{1-6}$ alkyl, $C_{1-6}$ alkoxy, halo $C_{1-6}$ alkyl or halo $C_{1-6}$ alkoxy;

(8)each $R_a$ is independently hydrogen, $C_{1-6}$ alkyl, $C_{3-8}$ cycloalkyl or 3- to 8-membered heterocycloalkyl; the $R_a$ is unsubstituted or optionally substituted at any position by 1 to 3 of the following substituents selected from halogen, hydroxyl, amino, $C_{1-6}$ alkoxy, $C_{1-6}$ alkylamino, halo $C_{1-6}$ alkyl and halo $C_{1-6}$ alkoxy;

(9) each $R_b$ is independently hydrogen or $C_{1-6}$ alkyl;

(10)each $R_c$ is independently hydrogen or $C_{1-6}$ alkyl; the $C_{1-6}$ alkyl is unsubstituted or optionally substituted at any position by 1 to 3 of the following substituents selected from halogen, hydroxyl, amino, $C_{1-6}$ alkoxy, $C_{1-6}$ alkylamino, halo $C_{1-6}$ alkyl and halo $C_{1-6}$ alkoxy; and

(11) each $R_d$ is independently hydrogen or $C_{1-6}$ alkyl.

4. The compound, the stereoisomer or the pharmaceutically acceptable salt thereof of claim 1, wherein $R_6$ and $R_7$ are each independently pyrrolyl, pyrazolyl or isoxazolyl; the pyrrolyl, pyrazolyl or isoxazolyl is unsubstituted or optionally substituted at any position by 1 to 3 of the following substituents selected from halogen, cyano, —$R_c$, —$OR_c$, —$NR_cR_d$, —$N(CN)R_c$, —$N(OR_d)R_c$, —$S(O)_{0-2}R_c$, —$C(O)R_c$, —$C(O)OR_c$, —$C(O)NR_cR_d$, —$C(NH)NR_cR_d$, —$NR_dC(O)R_c$, —$NR_dC(O)NR_cR_d$, —$NR_dS(O)_2R_c$ and —$OC(O)R_c$.

5. The compound, the stereoisomer or the pharmaceutically acceptable salt thereof of claim 1, wherein, the compound satisfies any one of the following conditions:

(1) in the compound of formula (II), the group

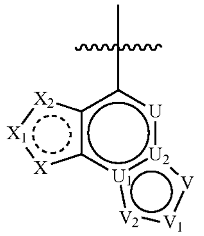

is

-continued

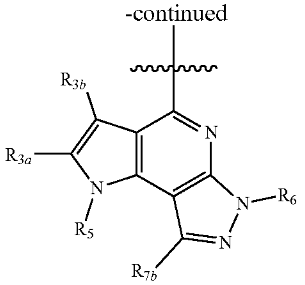

or

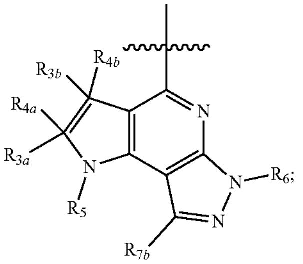

and (2) in the compound of formula (III), the group

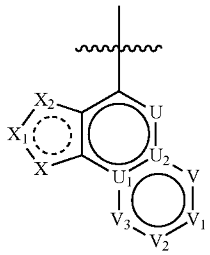

is

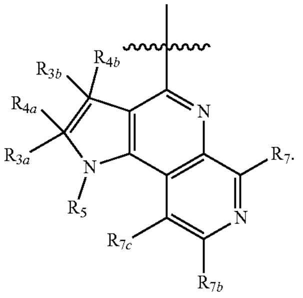

6. The compound, the stereoisomer or the pharmaceutically acceptable salt thereof of claim 5, wherein, the compound satisfies any one of the following conditions:

1) $R_{3a}$, $R_{3b}$, $R_{4a}$ and $R_{4b}$ are each independently hydrogen;

(2) $R_{7a}$ and $R_{7b}$ are each independently hydrogen; and (3) $R_6$ and $R_7$ are each independently pyrrolyl, pyrazolyl or isoxazolyl.

7. The compound, the stereoisomer or the pharmaceutically acceptable salt thereof of claim 1, wherein, in the compound of formula (II): $U_1$ and $U_2$ are C respectively; V is $NR_6$; $V_1$ is N or $CR_{7a}$; $V_2$ is N or $CR_{7b}$;

U is N; $R_6$ is pyrrolyl, pyrazolyl or isoxazolyl; the pyrrolyl, pyrazolyl or isoxazolyl is unsubstituted or optionally substituted at any position by 1 to 3 of the following substituents selected from halogen, cyano, —$R_c$, —$OR_c$, —$NR_cR_d$, —$N(CN)R_c$, —$N(OR_d)R_c$, —$S(O)_{0\text{-}2}R_c$, —$C(O)R_c$, —$C(O)OR_c$, —$C(O)NR_cR_d$, —$C(NH)NR_cR_d$, —$NR_dC(O)R_c$, —$NR_dC(O)NR_cR_d$, —$NR_dS(O)_2R_c$ and —$OC(O)R_c$;

$R_{7a}$ and $R_{7b}$ are each independently hydrogen;

$R_c$ and $R_d$ are each independently hydrogen or $C_{1\text{-}6}$ alkyl;

in the compound of formula (III): U is N; $R_7$ is pyrrolyl, pyrazolyl or isoxazolyl; the pyrrolyl, pyrazolyl or isoxazolyl is unsubstituted or optionally substituted at any position by 1 to 3 of the following substituents selected from halogen, cyano, —$R_c$, —$OR_c$, —$NR_cR_d$, —$N(CN)R_c$, —$N(OR_d)R_c$, —$S(O)_{0\text{-}2}R_c$, —$C(O)R_c$, —$C(O)OR_c$, —$C(O)NR_cR_d$, —$C(NH)NR_cR_d$, —$NR_dC(O)R_c$, —$NR_dC(O)NR_cR_d$, —$NR_dS(O)_2R_c$ and —$OC(O)R_c$;

$R_{7a}$, $R_{7b}$ and $R_{7c}$ are each independently hydrogen;

$R_c$ and $R_d$ are each independently hydrogen or $C_{1\text{-}6}$ alkyl.

8. The compound, the stereoisomer or the pharmaceutically acceptable salt thereof of claim 1, wherein, the compound of formula (II) is a compound of formula (IIA), (IIA)

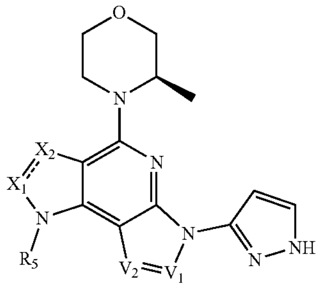

wherein, ---- is a double bond or a single bond;

the compound of formula (III) is a compound of formula (IIIA), (IIIA)

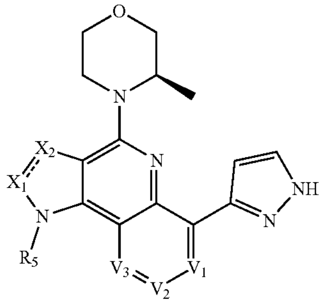

wherein, ---- is a double bond or a single bond.

9. The compound, the stereoisomer or the pharmaceutically acceptable salt thereof of claim 8, wherein, the compound satisfies any one of the following conditions:

(1) $X_1$ and $X_2$ are each independently N or CH; and (2) $X_1$ and $X_2$ are each independently $CH_2$.

10. The compound, the stereoisomer or the pharmaceutically acceptable salt thereof of claim 8, wherein, $R_5$ is $C_{1\text{-}6}$ alkyl, phenyl, $C_{3\text{-}8}$ cycloalkyl, 3- to 8-membered heterocycloalkyl, 5- to 6-membered heteroaryl, $C_{3\text{-}8}$ cycloalkyl-$C_{1\text{-}6}$ alkyl, 3- to 8-membered heterocycloalkyl-$C_{1\text{-}6}$ alkyl, 5- to 6-membered heteroaryl-$C_{1\text{-}6}$ alkyl, —$S(O)_{1\text{-}2}R_a$, —$S(O)_2NR_aR_b$, —$S(O)(=NCN)R_a$ or —$S(O)(=NR_b)R_a$;

wherein, the $C_{1-6}$ alkyl, phenyl, $C_{3-8}$ cycloalkyl, 3- to 8-membered heterocycloalkyl, 5- to 6-membered heteroaryl, $C_{3-8}$ cycloalkyl-$C_{1-6}$ alkyl, or 3- to 8-membered heterocycloalkyl-$C_{1-6}$ alkyl is unsubstituted or optionally substituted at any position by 1 to 3 of the following substituents selected from halogen, —CN, —$SR_a$, —$OR_a$, —$C(O)OR_a$, —$C(O)R_a$, —$C(O)NR_aR_b$, —$NR_aR_b$, —$NR_bC(O)R_a$, —$NR_bS(O)_2R_a$, —$S(O)_{1-2}R_a$, —$S(O)_2NR_aR_b$, —S(O)(═NCN)$R_a$ and —S(O)(═$NR_b$)$R_a$;

each $R_a$ is independently hydrogen or $C_{1-6}$ alkyl; the $C_{1-6}$ alkyl is unsubstituted or optionally substituted at any position by 1 to 3 of the following substituents selected from halogen, hydroxyl, amino, $C_{1-6}$ alkoxy, $C_{1-6}$ alkylamino, halo $C_{1-6}$ alkyl and halo $C_{1-6}$ alkoxy;

each $R_b$ is independently hydrogen or $C_{1-6}$ alkyl.

11. The compound, the stereoisomer or the pharmaceutically acceptable salt thereof of claim 8, wherein, in the compound of formula (IIA): $V_1$ and $V_2$ are each independently N or CH.

12. The compound, the stereoisomer or the pharmaceutically acceptable salt thereof of claim 8, wherein, in the compound of formula (IIIA): $V_1$, $V_2$ and $V_3$ are each independently N or CH.

13. The compound, the stereoisomer or the pharmaceutically acceptable salt thereof of claim 1, which is any one of the following structures:

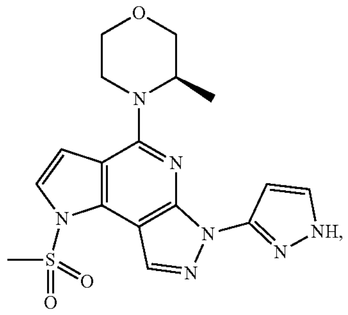

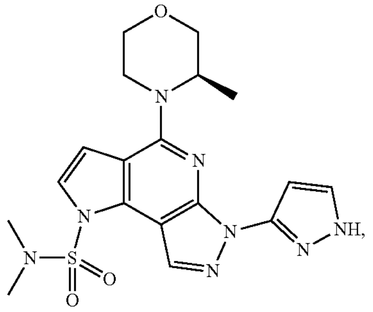

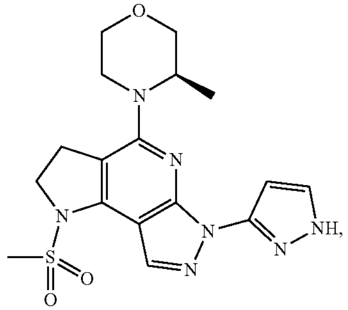

-continued

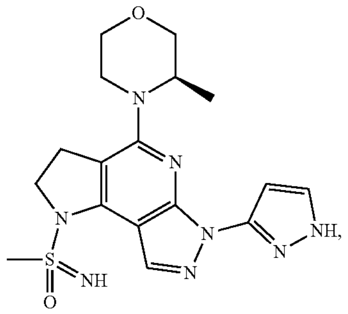

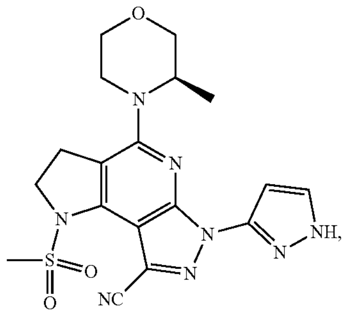

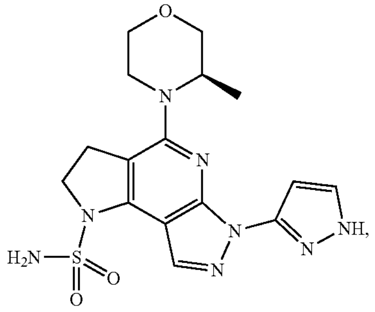

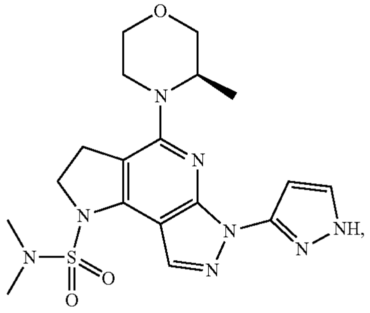

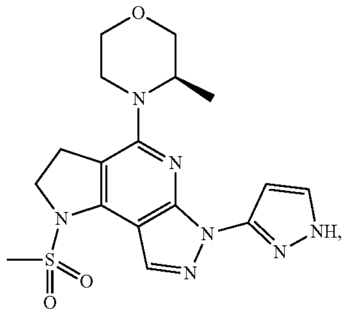

-continued
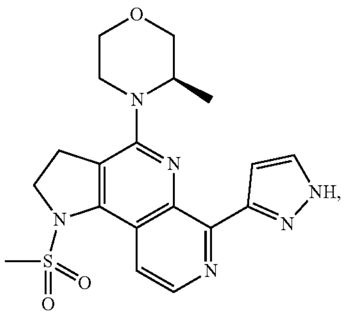
,
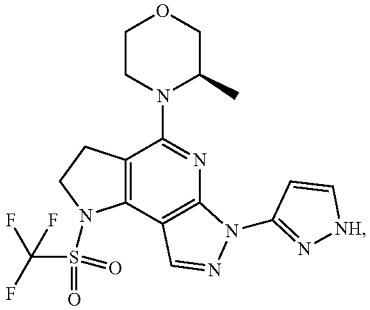
,
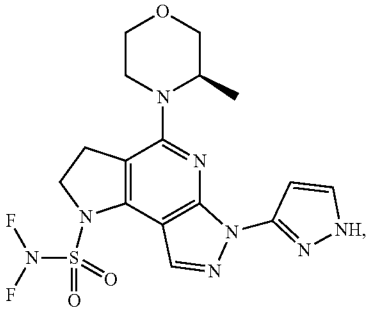
,
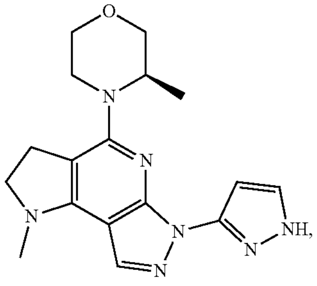
,
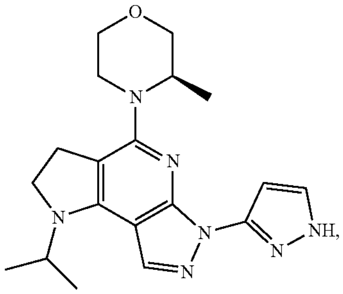
,
-continued
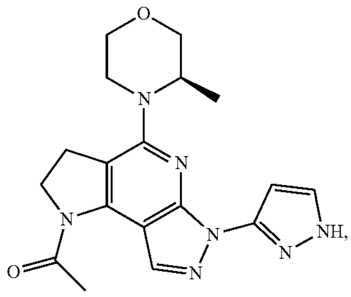
,
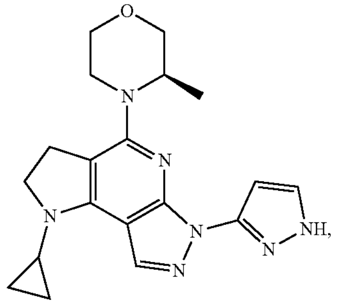
,
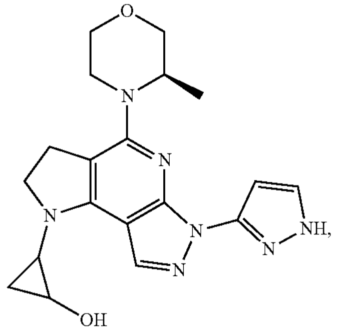
,
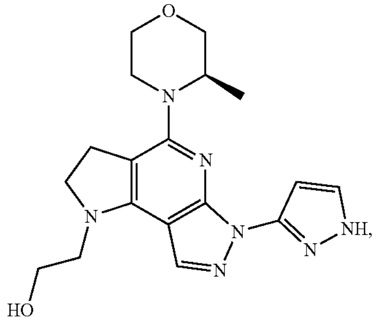
,
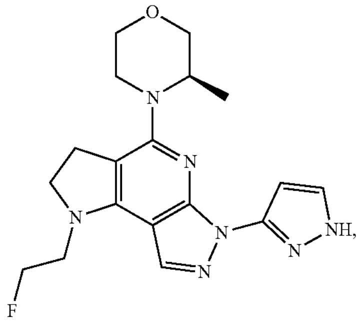
, -continued
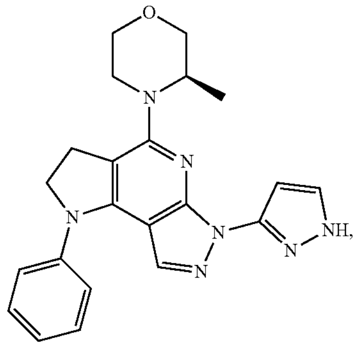
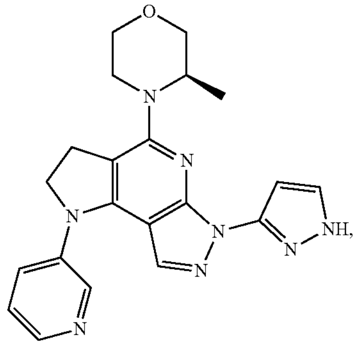
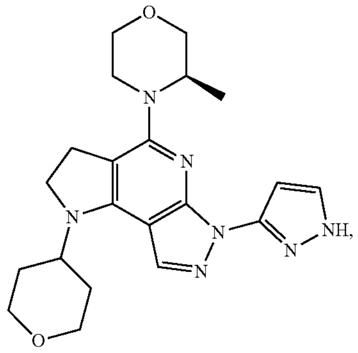
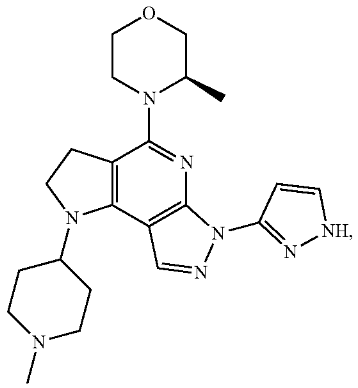
-continued
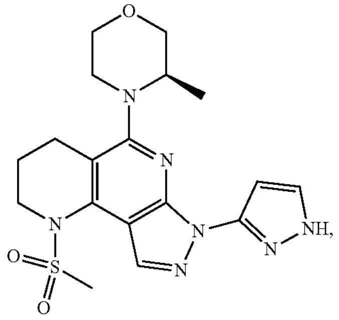
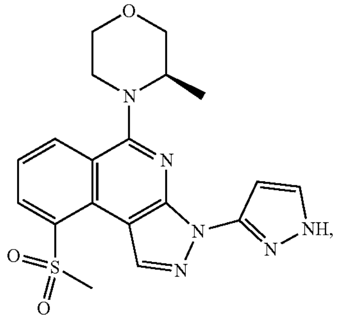
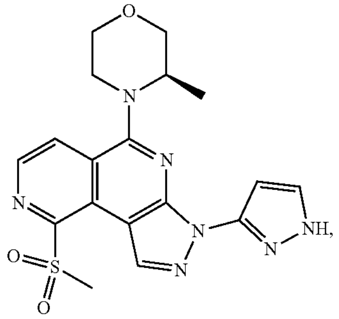
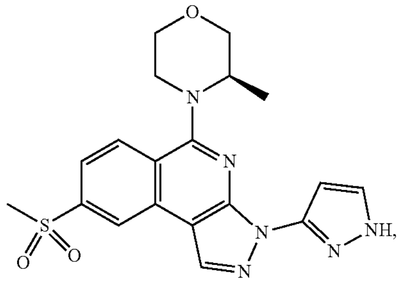
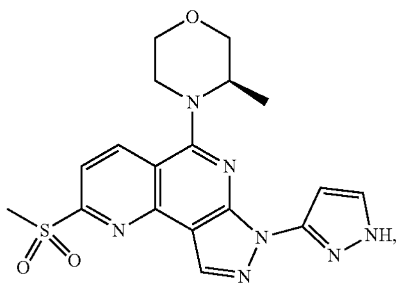

-continued

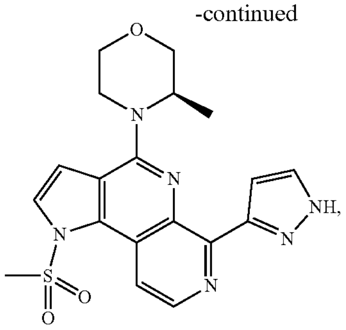

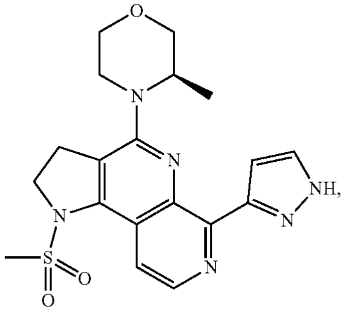

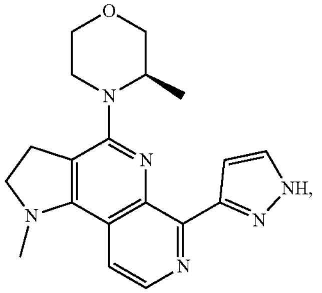

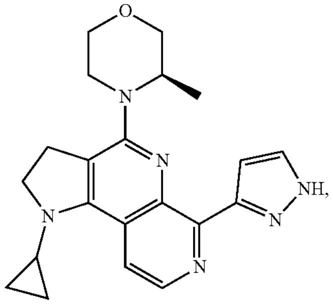

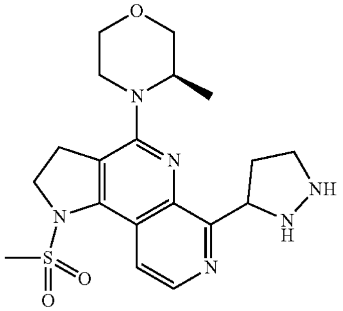

or

-continued

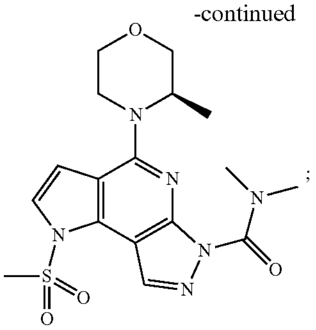

or a pharmaceutically acceptable salt thereof.

14. A pharmaceutical composition, comprising a therapeutically effective amount of an active component and a pharmaceutically acceptable excipient; the active component comprises the compound, the stereoisomer or the pharmaceutically acceptable salt thereof of claim 1.

15. A method for inhibiting ATR in a subject in need thereof, comprising: administering the compound, the stereoisomer thereof or the pharmaceutically acceptable salt thereof of claim 1 to the subject.

16. A method for treating cancer in a subject in need thereof, comprising: administering the compound, the stereoisomer thereof or the pharmaceutically acceptable salt thereof of claim 1 to the subject; wherein the cancer is selected from colon cancer, ovarian cancer, lung cancer, prostate cancer, lymphoblastic leukemia and non-Hodgkin's lymphoma.

17. A method for treating cancer in a subject in need thereof, comprising: administering the pharmaceutical composition of claim 14 to the subject; wherein the cancer is selected from colon cancer, ovarian cancer, lung cancer, prostate cancer, lymphoblastic leukemia and non-Hodgkin's lymphoma.

18. A method for treating cancer in a subject in need thereof, comprising: administering the compound, the stereoisomer thereof or the pharmaceutically acceptable salt thereof of claim 1 to the subject in combination with one or more other kinds of therapeutic agents or treatment methods for treating cancer; wherein the cancer is selected from colon cancer, ovarian cancer, lung cancer, prostate cancer, lymphoblastic leukemia and non-Hodgkin's lymphoma.

19. A method for treating cancer in a subject in need thereof, comprising: administering the compound, the stereoisomer thereof or the pharmaceutically acceptable salt thereof of claim 1 to the subject; wherein the cancer is selected from colon cancer and diffuse large B-Cell lymphoma.

20. A method for treating cancer in a subject in need thereof, comprising: administering the compound, the stereoisomer thereof or the pharmaceutically acceptable salt thereof of claim 1 to the subject in combination with one or more other kinds of therapeutic agents or treatment methods for treating cancer; wherein the cancer is selected from colon cancer and diffuse large B-Cell lymphoma.

* * * * *